United States Patent
Rock et al.

(10) Patent No.: US 10,378,022 B2
(45) Date of Patent: Aug. 13, 2019

(54) TRANSCRIPTION FACTORS AND METHOD FOR INCREASED FIBER LENGTH OF COTTON

(71) Applicants: Christopher Dale Rock, Lubbock, TX (US); Amandeep Mittal, Abohar Punjab (IN)

(72) Inventors: Christopher Dale Rock, Lubbock, TX (US); Amandeep Mittal, Abohar Punjab (IN)

( * ) Notice: Subject to any disclaimer, the term of this patent is extended or adjusted under 35 U.S.C. 154(b) by 0 days.

(21) Appl. No.: 15/534,881

(22) PCT Filed: Dec. 9, 2015

(86) PCT No.: PCT/US2015/064775
§ 371 (c)(1),
(2) Date: Jun. 9, 2017

(87) PCT Pub. No.: WO2016/094547
PCT Pub. Date: Jun. 16, 2016

(65) Prior Publication Data
US 2017/0369897 A1    Dec. 28, 2017

Related U.S. Application Data

(60) Provisional application No. 62/089,567, filed on Dec. 9, 2014.

(51) Int. Cl.
*C12N 15/82*   (2006.01)
*C07K 14/415*  (2006.01)

(52) U.S. Cl.
CPC ........ *C12N 15/8273* (2013.01); *C07K 14/415* (2013.01); *C12N 15/827* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| 7,446,241 | B2 | 11/2008 | Rock et al. |
| 8,283,519 | B2 | 10/2012 | Creelman et al. |
| 8,492,618 | B2 * | 7/2013 | Bourland ............... A01H 5/10 435/427 |
| 8,541,665 | B2 | 9/2013 | Jiang et al. |
| 2009/0083877 | A1 | 3/2009 | Rock et al. |
| 2011/0277190 | A1 | 11/2011 | Abad |

OTHER PUBLICATIONS

Mittal, A, Doctor of Philosophy Dissertation, Texas Tech University, 2012, online https://ttu-ir.tdl.org/handle/2346/73879?show=full (Year: 2012).*
Mittal, A., Dissertation, Availability date Jun. 4, 2018 (Year: 2018).*
Zhao L., et al., "A RAV-like transcription factor controls photosynthesis and senescence in soybean." Planta (2008), 227:1389-1399.
Abdurakhmonov I.Y., et al., "Phytochrome RNA interference enhances major fibre quality and agronomic traits of the cotton (*Gossypium hirsutum* L.)" Nature Communications (2014), 5, e3062.
Ando E., et al., "Twin Sister of FT, Gigantea, and Constans have a positive but indirect effect on blue light-induced stomatal opening in *Arabidopsis*." Plant Physiology (2013), 162:1529-1538.
*Arabidopsis* Interactome Mapping Consortium "Evidence for network evolution in an *Arabidopsis* interactome map." Science (2011), 333:601-607.
Arpat A., et al., "Functional genomics of cell elongation in developing cotton fibers." Plant Molecular Biology (2004), 54:911-929.
Bai W.-Q., et al., "Gibberellin overproduction promotes sucrose synthase expression and secondary cell wall deposition in cotton fibers." PLoS ONE (2014), 9:e96537.
Basra A.S., et al., "Growth regulation of cotton fibers." Cotton Fibers: Developmental Biology, Quality Improvement, and Textile Processing (ed A.S. Basra), (1999), pp. 47-58. Haworth Press, New York.
Bassel G.W., et al., "Systems analysis of plant functional, transcriptional, physical interaction, and metabolic networks." Plant Cell (2012), 24:3859-3875.
Bayley C., et al., "Engineering 2,4-D resistance into cotton." Theoretical and Applied Genetics (1992), 83:645-649.
Bedon F., et al., "Members of the MYBMIXTA-like transcription factors may orchestrate the initiation of fibre development in cotton seeds." Frontiers in Plant Science (2014), 5:e179.
Belda-Palazón B., et al., "Biochemical quantitation of the eIF5A hypusination in *Arabidopsis thaliana* uncovers ABA-dependent regulation." Frontiers in Plant Science (2014), 5:e202.
Bourland F.M., et al., "Registration of Arkot 8712 germplasm line of cotton." Crop Science (2005), 45:1173-1174.
Bourland F.M., et al., "Registration of 'UA48' cotton cultivar." Journal of Plant Registrations (2012), 6:15-18.
Boyer J.S. "Plant productivity and environment." Science (1982), 218:443-448.
Brandt R., et al., "Homeodomain leucine-zipper proteins and their role in synchronizing growth and development with the environment" Journal of Integrative Plant Biology (2014), 56:518-526.
Brocard I.M., et al., "Regulation and role of the *Arabidopsis* Abscisic Acid-Insensitive 5 gene in abscisic acid, sugar, and stress response." Plant Physiology (2002), 129:1533-1543.
Cai Z., et al., "GSK3-like kinases positively modulate abscisic acid signaling through phosphorylating subgroup III SnRK2s in *Arabidopsis*." Proceedings of the National Academy of Sciences, U.S.A. (2014), 111:9651-9656.
Castillejo C., et al., "The balance between Constans and Tempranillo activities determines FT expression to trigger flowering." Current Biology (2008), 18:1338-1343.
Causier B., et al., The TOPLESS interactome: a framework for gene repression in *Arabidopsis*. Plant Physiology (2012), 158:423-438.

(Continued)

*Primary Examiner* — Eileen B O Hara
(74) *Attorney, Agent, or Firm* — Edwin S. Flores; Daniel J. Chalker; Chalker Flores, LLP

(57) ABSTRACT

The present invention includes a seed, a plant, a protoplast, a hybrid and methods of making the same of a cotton cultivar recombinantly modified overexpresses at least one of AtRAV1, AtRAV2 to confer longer fibers to transgenic cotton plants under drought conditions without an effect on yield.

23 Claims, 14 Drawing Sheets
Specification includes a Sequence Listing.

(56) References Cited

OTHER PUBLICATIONS

Cedroni M.L., et al., "Evolution and expression of MYB genes in diploid and polyploid cotton." Plant Molecular Biology (2003), 51:313-325.
Chen L., et al., "Identification of *Arabidopsis* MYB56 as a novel substrate for CRL3BPM E3 ligases." Molecular Plant (2015), 8:242-250.
Chen X., et al., "Isolation and characterization of GoRAV, a novel gene encoding a RAV-type protein in Galegae orientalis." Genes and Genetic Systems (2009), 84:101-109.
Choi D., et al., "iNID: an analytical framework for identifying network models for interplays among developmental signaling in *Arabidopsis*." Molecular Plant (2013), 7:792-813.
Culp T.W., et al., "Influence of lint percentage, boll size, and seed size on lint yield of upland cotton with high fiber strength" Crop Science (1975), 15:741-746.
Deng F., et al., "GbPDF1 is involved in cotton fiber initiation via the core cis-element HDZIP2ATATHB2." Plant Physiology (2012), 158:890-904.
Deng W., et al., "Flowering Locus C (FLC) regulates development pathways throughout the life cycle of *Arabidopsis*." Proceedings of the National Academy of Sciences, U.S.A. (2011), 108:6680-6685.
Ding M., et al., "Gene expression profile analysis of Ligon lintless-1 (Li1) mutant reveals important genes and pathways in cotton leaf and fiber development" (2014), Gene 535, 273-285.
Endres M.W., et al., "Two plant viral suppressors of silencing require the ethylene-inducible host transcription factor RAV2 to block RNA silencing." PLoS Pathogens (2010), 6:e1000729.
Fang L., et al., "Cotton fiber elongation network revealed by expression profiling of longer fiber lines introgressed with different Gossypium barbadense chromosome segments." BMC Genomics (2014), 15:838.
Feng C.-Z., et al., "*Arabidopsis* RAV1 transcription factor, phosphorylated by SnRK2 kinases, regulates the expression of ABI3, ABI4, and ABI5 during seed germination and early seedling development." Plant Journal (2014), 80:654-668.
Finkelstein R., et al., "Redundant and distinct functions of the ABA response loci ABA-Insensitive(ABI)5 and ABRE-Binding Factor (ABF)3." Plant Molecular Biology (2005), 59:253-267.
Fu M., et al., "A subset of RAV transcription factors modulates drought and salt stress responses ABA-independently in *Arabidopsis*." Plant and Cell Physiology (2014), 55:1892-1904.
Geisler-Lee J., et al., "A predicted interactome for *Arabidopsis*." Plant Physiology (2007), 145:317-329.
Gilbert M.K., et al., "A transcript profiling approach reveals an abscisic acid-specific glycosyltransferase (UGT73C14) induced in developing fiber of Ligon lintless-2 mutant of cotton (*Gossypium hirsutum* L.)." PLoS ONE (2013), 8:e75268.
Gilbert M.K., et al., "Comparative transcriptome analysis of short fiber mutants Ligon-Lintless 1 And 2 reveals common mechanisms pertinent to fiber elongation in cotton (*Gossypium hirsutum* L.)." PLoS ONE (2014), 9:e95554.
Giraudat J., et al., "Isolation of the *Arabidopsis* ABI3 gene by positional cloning." Plant Cell (1992), 4:1251-1261.
Gregory K., et al., "Fiber and yarn performance of upland cotton with improved fiber bundle strength." Crop Science (2012), 52:1061-1067.
Gu X., et al., "Photoperiodic regulation of flowering time through periodic histone deacetylation of the florigen gene FT." PLoS Biology (2013), 11:e1001649.
Guan X., et al., "miR828 and miR858 regulate homoeologous MYB2 gene functions in *Arabidopsis trichome* and cotton fibre development." Nature Communications (2014), 5:3050.
Guo H., et al., "Plant responses to ethylene gas are mediated by SCFEBF1/EBF2-dependent proteolysis of EIN3 transcription factor." Cell (2003), 115:667-677.
Han J., et al., "A peptide hormone gene, GhPSK promotes fibre elongation and contributes to longer and finer cotton fibre." Plant Biotechnology Journal (2014), 12:861-871.

Han L.-B., et al., "The dual functions of WLIM1a in cell elongation and secondary wall formation in developing cotton fibers." Plant Cell (2013), 25:4421-4438.
Hao J., et al., "GbTCP, a cotton TCP transcription factor, confers fibre elongation and root hair development by a complex regulating system." Journal of Experimental Botany (2012), 63:6267-6281.
Hobo T., et al., "A bZIP factor, TRAB1, interacts with VP1 and mediates abscisic acid-induced transcription." Proceedings of the National Academy of Sciences, U.S.A. (1999), 96:15348-15353.
Hu J.-Y., et al., "miR824-regulated AGAMOUS-LIKE16 contributes to flowering time repression in *Arabidopsis*." Plant Hell (2014), 26:2024-2037.
Hu Y.X., et al., "*Arabidopsis* RAV1 is down-regulated by brassinosteroid and may act as a negative regulator during plant development." Cell Research (2004), 14:8-15.
Huang G.-Q., et al., "A fasciclin-like arabinogalactan protein, GhFLA1, is involved in fiber initiation and elongation of cotton." Plant Physiology (2013), 161:1278-1290.
Huang Y., et al., "Functional analysis of the seed coat-specific gene GbMYB2 from cotton." Plant Physiology and Biochemistry (2013), 73:16-22.
Ikeda M., et al., "A novel group of transcriptional repressors in *Arabidopsis*." Plant and Cell Physiology (2009), 60:970-975.
International Search Report and Written Opinion for PCT/US2015/064775 dated Mar. 18, 2016.
Ito S., et al., "Flowering BHLH transcriptional activators control expression of the photoperiodic flowering regulator CONSTANS in *Arabidopsis*." Proceedings of the National Academy of Sciences, U.S.A. (2012), 109:3582-3587.
Je B.I., et al., "RAV-Like1 maintains brassinosteroid homeostasis via the coordinated activation of BRI1 and biosynthetic genes in rice." Plant Cell (2010), 22:1777-1791.
Jeong J.-H., et al., "Repression of Flowering Locus T chromatin by functionally redundant histone H3 lysine 4 demethylases in *Arabidopsis*." PLoS ONE (2009), 4:e8033.
Jia F., et al., "Cre-lox univector acceptor vectors for functional screening in protoplasts: analysis of *Arabidopsis* donor cDNAs encoding Abscisic Acid INSENSITIVE1-like protein phosphatases." Plant Molecular Biology (2009), 70:693-708.
Jia F., et al., "Jacalin lectin At5g28520 is regulated by ABA and miR846." Plant Signaling & Behavior (2013), 8:e24563.
Jia X., et al., "Differential and dynamic regulation of miR398 in response to ABA and salt stress in Populus tremula and *Arabidopsis thaliana*." Plant Molecular Biology (2009), 71:51-59.
Jiang Y., et al., "Overexpression of GhSusA1 increases plant biomass and improves cotton fiber yield and quality." Plant Biotechnology Journal (2012), 10:301-312.
Kagaya Y., et al., "*Arabidopsis* transcription factors, RAV1 and RAV2, are regulated by touch-related stimuli in a dose-dependent and biphasic manner." Genes and Genetic Systems (2009), 84:95-99.
Kagaya Y., et al., "RAV1, a novel DNA-binding protein, binds to bipartite recognition sequence through two distinct DNA-binding domains uniquely found in higher plants." Nucleic Acids Research (1999), 27:470-478.
Källman T., et al., "A significant fraction of 21 nt sRNA originates from phased degradation of resistance genes in several perennial species." Plant Physiology (2013), 162:741-754.
Kim H., et al., "Functional analyses of cotton (*Gossypium hirsutum* L.) immature fiber (im) mutant infer that fiber cell wall development is associated with stress responses." BMC Genomics (2013), 14:889.
Kim H.J., et al., "Cotton fiber growth in planta and in vitro. Models for plant cell elongation and cell wall biogenesis." Plant Physiology (2001), 127:1361-1366.
Kim W., et al., "MicroRNA-target interactions: important signaling modules regulating flowering time in diverse plant species." Critical Reviews in Plant Sciences (2014), 33:470-485.
Kinoshita T., et al., "Flowering Locus T regulates stomatal opening." Current Biology (2011), 21:1232-1238.
Laurie R.E., et al., "The Medicago Flowering Locus T homolog, MtFTa1, is a key regulator of flowering time." Plant Physiology (2011), 156:2207-2224.

(56) References Cited

OTHER PUBLICATIONS

Lee S., et al., "The pepper oxidoreductase CaOXR1 interacts with the transcription factor CaRAV1 and is required for salt and osmotic stress tolerance." Plant Molecular Biology (2010), 73:409-424.

Lee T., et al., "AraNet v2: an improved database of co-functional gene networks for the study of *Arabidopsis thaliana* and 27 other nonmodel plant species." Nucleic Acids Research (2014), 43:D996-D1002.

Li C.-W., et al., "Tomato RAV transcription factor is a pivotal modulator involved in the AP2/EREBP-mediated defense pathway." Plant Physiology (2011), 156:213-227.

Li F., et al., "Genome sequence of the cultivated cotton *Gossypium arboreum*." Nature Genetics (2014), 46:567-572.

Li W.-X., et al., "The *Arabidopsis* NFYA5 transcription factor is regulated transcriptionally and posttranscriptionally to promote drought resistance." Plant Cell (2008), 20:2238-2251.

Li X., et al., "Genetic mapping and characteristics of genes specifically or preferentially expressed during fiber development in cotton." PLoS ONE (2013), 8:e54444.

Little J.B. "Saving the Ogallala Aquifer." Scientific American (2009), 19:32-39.

Liu K., et al., "Transcriptome analysis reveals critical genes and key pathways for early cotton fiber elongation in Ligon intless-1 mutant." Genomics (2012), 100:42-50.

Liu L., et al., "Induced and natural variation of promoter length modulates the photoperiodic response of Flowering Locus T." Nature Communications (2014), 5:e4558.

Liu L., et al., "Elevated levels of MYB30 in the phloem accelerate flowering in *Arabidopsis* through the regulation of Flowering Locus T." PLoS ONE (2014), 9:e89799.

Liu N., et al., "Small RNA and degradome profiling reveals a role for miRNAs and their targets in the developing fibers of Gossypium barbadense." Plant Journal (2014), 80:331-344.

Loguerico L.L., et al., "Differential regulation of six novel MYB-domain genes defines two distinct expression patterns in allotetraploid cotton (*Gossypium hirsutum* L) ." Molecular and General Genetics (1999), 261:660-671.

Lu Q., et al., "A GmRAV ortholog is involved in photoperiod and sucrose control of flowering time in soybean." PLoS ONE (2014), 9:e89145.

Lumba S., et al., "A mesoscale abscisic acid hormone interactome reveals a dynamic signaling landscape in *Arabidopsis*." Developmental Cell (2014), 29:360-372.

Luo J., et al., "A cotton mitogen-activated protein kinase (GhMPK6) is involved in ABA-induced CAT1 expression and H2O2 production." Journal of Genetics and Genomics (2011), 38:557-565.

Luo M., et al., "GhDET2, a steroid 5α-reductase, plays an important role in cotton fiber cell initiation and elongation." Plant Journal (2007), 51:419-430.

Luo Q.-J., et al., "An autoregulatory feedback loop involving PAP1 and TAS4 in response to sugars in *Arabidopsis*." Plant Molecular Biology (2012), 80:117-129.

Machado A., et al., "The MYB transcription factor GhMYB25 regulates early fibre and trichome development." Plant Journal (2009), 59:52-62.

Matías-Hernández L., et al., "RAV genes: regulation of floral induction and beyond." Annals of Botany (2014), 114:1459-1470.

Matsoukas I.G., et al., "Florigenic and antiflorigenic signaling in plants." Plant and Cell Physiology (2012), 53:1827-1842.

McCarty D.R., et al., "The Viviparous-1 developmental gene of maize encodes a novel transcriptional activator." Cell (1991), 66:895-905.

McGarry R.C., et al., "Geminivirus-mediated delivery of florigen promotes determinate growth in aerial organs and uncouples flowering from photoperiod in cotton." PLoS ONE (2012), 7:e36746.

McGarry R.C., et al., "Overexpression of FT in cotton affects architecture but not floral organogenesis." Plant Signaling & Behavior (2013), 8:e23602.

Min H., et al., "Maize ZmRAV1 contributes to salt and osmotic stress tolerance in transgenic *Arabidopsis*." Journal of Plant Biology (2014), 57:28-42.

Mittal A., et al., "Related to ABA-Insensitive3(ABI3)/Viviparous1 and AtABI5 transcription factor coexpression in cotton enhances drought stress adaptation." Plant Biotechnology Journal (2014), 12:578-589.

Mittal, A. et al., "Production and testing of transgenic cotton that expresses transcription factors for enhanced seed and fiber traits and productivity under drought stress." Beltwide Cotton Conferences, Atlanta Georgia, (Jan. 4-7, 2011). Abstract 12321.

Mittal, A. et al., "AtRAV1 and AtRAV2 overexpression in cotton increases fiber length differentially under drought stress and delays flowering." Plant Science. (2015), 241:78-95.

Moreno-Cortés A., et al., "CsRAV1 induces sylleptic branching in hybrid poplar." New Phytologist (2012), 194:83-90.

Mutasa-Gottgens E., et al., "A new RNASeq-based reference transcriptome for sugar beet and its application in transcriptome-scale analysis of vernalization and gibberellin responses." BMC Genomics (2012), 13:99.

Naoumkina M., et al., "The Li2 mutation results in reduced subgenome expression bias in elongating fibers of allotetraploid cotton (*Gossypium hirsutum* L.) ." PLoS ONE (2014), 9:e90830.

Nigam D., et al., "Transcriptome dynamics during fibre development in contrasting genotypes of Gossypium hirsutum L." Plant Biotechnology Journal (2014), 12:204-218.

Osnato M., et al., "Tempranillo genes link photoperiod and gibberellin pathways to control flowering in *Arabidopsis*." Nature Communications (2012), 3:808.

Padmalatha K., et al., "Genome-wide transcriptomic analysis of cotton under drought stress reveal significant down-regulation of genes and pathways involved in fibre elongation and up-regulation of defense responsive genes." Plant Molecular Biology (2012), 78:223-246.

Parkash J., et al., "Translation initiation factor 5A in Picrorhiza is up-regulated during leaf senescence and in response to abscisic acid." Gene (2014), 542:1-7.

Pettigrew W.T. "Moisture deficit effects on cotton lint yield, yield components, and boll distribution." Agronomy Journal (2004), 96:377-383.

Potikha T.S., et al., "The involvement of hydrogen peroxide in the differentiation of secondary walls in cotton fibers." Plant Physiology (1999), 119:849-858.

Pu L., Li Q., et al., "The R2R3 MYB transcription factor GhMYB109 is required for cotton fiber development." Genetics (2008), 180:811-820.

Qu J., et al., "Dissecting functions of Katanin and Wrinkled1 in cotton fiber development by virus-induced gene silencing." Plant Physiology (2012), 160, 738-748.

Reyes J.L., et al., "ABA induction of miR159 controls transcript levels of two MYB factors during *Arabidopsis* seed germination." Plant Journal (2007), 49:592-606.

Riboni M., et al., "Gigantea enables drought escape response via abscisic acid-dependent activation of the Florigens and Suppressor of Overexpression of Constans." Plant Physiology (2013), 162:1706-1719.

Rock C.D. "Trans-acting small interfering RNA4: key to nutraceutical synthesis in grape development?" Trends in Plant Science (2013), 18:601-610.

Rock, C.D. et al., "Production and field testing of transgenic cotton that expresses transcription factors for enhanced seed traits and productivity under drought stress." Ogallala Aquifer Program Workshop, Slide Presentation, Mar. 5, 2013.

Ryu H., et al., "Control of early seedling development by BES1/TPL/HDA19-mediated epigenetic regulation of ABI3." Nature Communications (2014), 5:e4138.

Sawa M., et al., "Gigantea directly activates Flowering Locus T in *Arabidopsis thaliana*." Proceedings of the National Academy of Sciences, U.S.A. (2011), 108:11698-11703.

Seo E., et al., "Werewolf, a regulator of root hair pattern formation, controls flowering time through the regulation of FT mRNA stability." Plant Physiology (2011), 156:1867-1877.

(56) References Cited

OTHER PUBLICATIONS

Sgamma T., et al., "Tempranillo is a regulator of juvenility in plants." Scientific Reports (2014), 4:e3704.
Shi Y.-H., et al., "Transcriptome profiling, molecular biological, and physiological studies reveal a major role for ethylene in cotton fiber cell elongation." Plant Cell (2006), 18:651-664.
Spanudakis E., et al., "The role of microRNAs in the control of flowering time." Journal of Experimental Botany (2014), 65:365-380.
Sun F., et al., "A conserved RNA recognition motif (RRM) domain of Brassica napus FCA improves cotton fiber quality and yield by regulating cell size." Molecular Breeding (2012), 30:93-101.
Sunilkumar G., et al., "Developmental and tissue-specific expression of CaMV 35S promoter in cotton as revealed by GFP." Plant Molecular Biology (2002), 50:463-479.
Szklarczyk D., et al., "The String database in 2011: functional interaction networks of proteins, globally integrated and scored." Nucleic Acids Research (2011), 39:D561-D568.
Takahashi Y., et al., (2013) bHLH transcription factors that facilitate K+ uptake during stomatal opening are repressed by abscisic acid through phosphorylation. Science Signaling 6:ra48.
Tan J., et al., "A genetic and metabolic analysis revealed that cotton fiber cell development was retarded by flavonoid naringenin." Plant Physiology (2013), 162:86-95.
Tang W., et al., "The calcium sensor GhCaM7 promotes cotton fiber elongation by modulating reactive oxygen species (ROS) production." New Phytologist (2014), 202:509-520.
Thyssen G.N., et al., "Independent replication of mitochondrial genes supports the transcriptional program in developing fiber cells of cotton (Gossypium hirsutum L.)." Gene (2014), 544:41-48.
Unruh B.L., et al., "Planting and irrigation termination timing effects on the yield of upland and pima cotton." Journal of Production Agriculture (1997), 10:74-79.
Van Landeghem S., et al., "The potential of text mining in data integration and network biology for plant research: a case study on Arabidopsis." Plant Cell (2013), 25:794-807.
Velten J., et al., "Transgene silencing and transgene-derived siRNA production in tobacco plants homozygous for an introduced AtMYB90 construct." PLoS ONE (2012), 7:e30141.
Walford S.-A., et al., "GhMYB25-like: a key factor in early cotton fibre development." Plant Journal (2011), 65:785-797.
Walford S.-A., et al., "Epidermal cell differentiation in cotton mediated by the homeodomain leucine zipper gene, GhHD-1." Plant Journal (2012), 71:464-478.
Wan Q., et al., "Genome-wide transcriptome profiling revealed cotton fuzz fiber development having a similar molecular model as Arabidopsis trichome." PLoS ONE (2014), 9:e97313.
Wang C., et al., "Aberrant phenotype and transcriptome expression during fiber cell wall thickening caused by the mutation of the Im gene in immature fiber (im) mutant in Gossypium hirsutum L." BMC Genomics (2014), 15:94.
Wang G., et al., "Transcript profiling during salt stress of young cotton (Gossypium hirsutum) seedlings via Solexa sequencing." Acta Physiologiae Plantarum (2012), 34:107-115.
Wang K., et al., "The draft genome of a diploid cotton Gossypium raimondii." Nature Genetics (2012), 44:1098-1103.
Wang L., et al., "Characterization of a eukaryotic translation initiation factor 5A homolog from Tamarix androssowii involved in plant abiotic stress tolerance." BMC Plant Biology (2012), 12:118.
Wang L., et al., "Silencing the vacuolar invertase gene GhVIN1 blocks cotton fiber initiation from the ovule epidermis, probably by suppressing a cohort of regulatory genes via sugar signaling." Plant Journal (2014), 78:686-696.
Wang M.-Y., et al., "The cotton transcription factor TCP14 functions in auxin-mediated epidermal cell differentiation and elongation." Plant Physiology (2013), 162:1669-1680.
Wang P., et al., "Quantitative phosphoproteomics identifies SnRK2 protein kinase substrates and reveals the effectors of abscisic acid action." Proceedings of the National Academy of Sciences, U.S.A. (2013), 110:11205-11210.
Wang S., et al., "Control of plant trichome development by a cotton fiber MYB gene." Plant Cell (2004), 16:2323-2334.
Wang Y., et al., "Systematic analysis of plant-specific B3 domain-containing proteins based on the genome resources of 11 sequenced species." Molecular Biology Reports (2012), 39:6267-6282.
Wang Z.-M., et al., "A comparative miRNAome analysis reveals seven fiber initiation-related and 36 novel miRNAs in developing cotton ovules." Molecular Plant (2012), 5:889-900.
Wingler A., et al., "Metabolic regulation of leaf senescence: interactions of sugar signaling with biotic and abiotic stress responses." Plant Biology (2008), 10:50-62.
Woo H.R., et al., "The RAV1 transcription factor positively regulates leaf senescence in Arabidopsis." Journal of Experimental Botany (2010), 61:3947-3957.
Wu L., et al., "Regulation of Flowering Locus T by a microRNA in Brachypodium distachyon." Plant Cell (2013), 25:4363-4377.
Wu Y., et al., "Expression profiling identifies genes expressed early during lint fibre initiation in cotton." Plant and Cell Physiology (2006), 47:107-127.
Xu B., et al., "A cotton BURP domain protein interacts with α-expansin and their co-expression promotes plant growth and fruit production." Molecular Plant (2013), 6:945-958.
Xu S.-M., et al., "Overexpression of a potato sucrose synthase gene in cotton accelerates leaf expansion, reduces seed abortion, and enhances fiber production." Molecular Plant (2012), 5:430-441.
Yamaguchi A., et al., "Twin Sister of FT (TSF) acts as a floral pathway integrator redundantly with FT." Plant and Cell Physiology (2005), 46:1175-1189.
Yang W., et al., "A plant-specific histone H3 lysine 4 demethylase represses the floral transition in Arabidopsis." Plant Journal (2010), 62:663-673.
Yang Z., et al., PAG1, a cotton brassinosteroid catabolism gene, modulates fiber elongation. New Phytologist (2014), 203, 437-448.
Yoo M.-J., et al., "Comparative evolutionary and developmental dynamics of the cotton (Gossypium hirsutum) fiber transcriptome." PLoS Genetics (2014), 10:e1004073.
Yoshida T., et al., "Four Arabidopsis AREB/ABF transcription factors function predominantly in gene expression downstream of SnRK2 kinases in abscisic acid signalling in response to osmotic stress." Plant, Cell & Environment, (2015), 38:35-49.
Zhang D., et al., "Effect of H2O2 on fiber initiation using fiber retardation initiation mutants in cotton (Gossypium hirsutum)." Journal of Plant Physiology (2010), 167:393-399.
Zhang F., et al., "An L1 box binding protein, GbML1, interacts with GbMYB25 to control cotton fibre development." Journal of Experimental Botany (2010), 61:3599-3613.
Zhang M., et al., "Spatiotemporal manipulation of auxin biosynthesis in cotton ovule epidermal cells enhances fiber yield and quality," Nature Biotechnology (2011), 29:453-458.

* cited by examiner

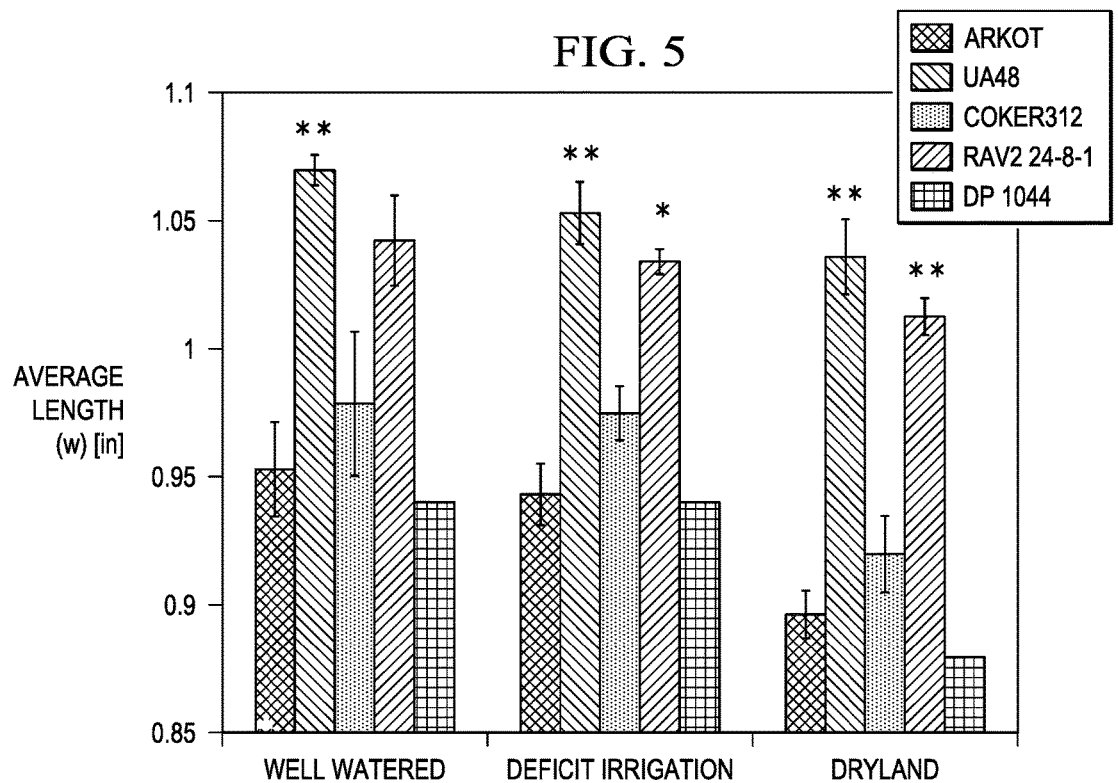
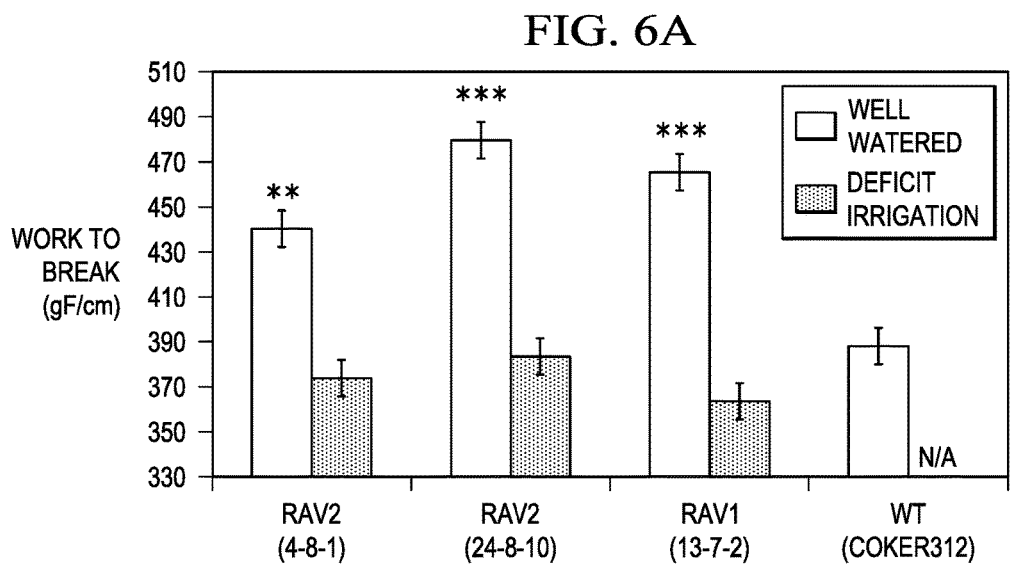

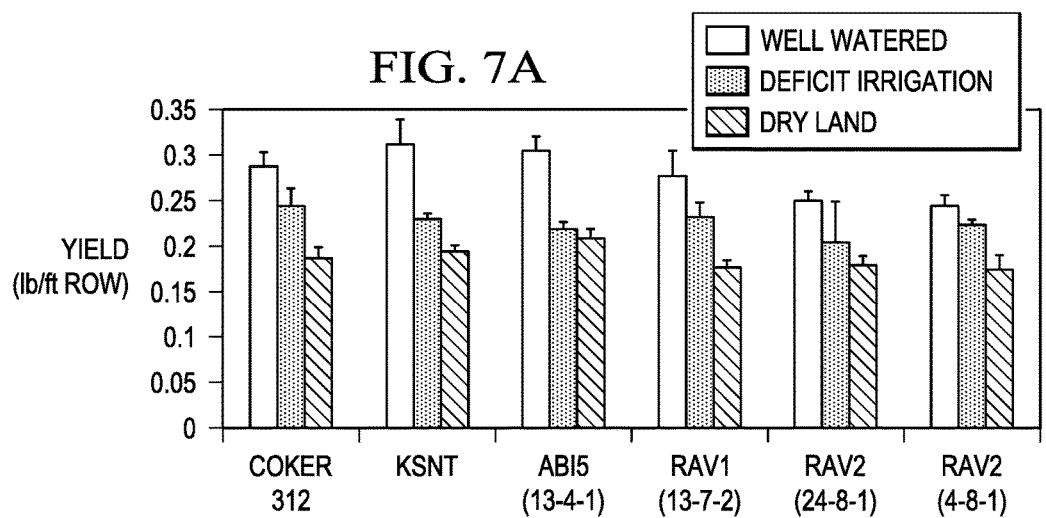
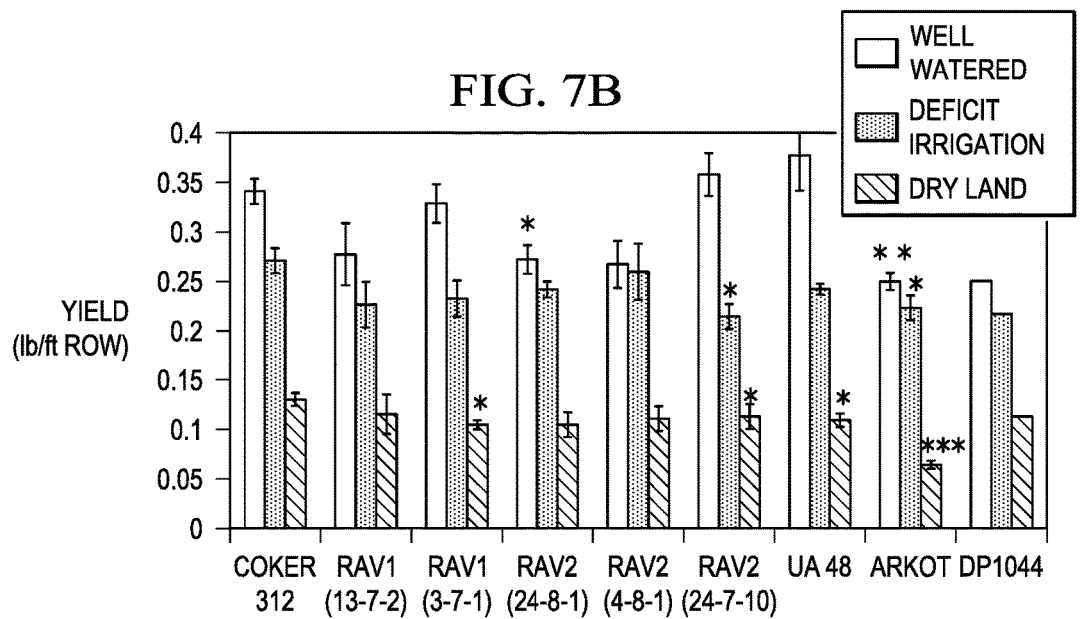

FIG. 11
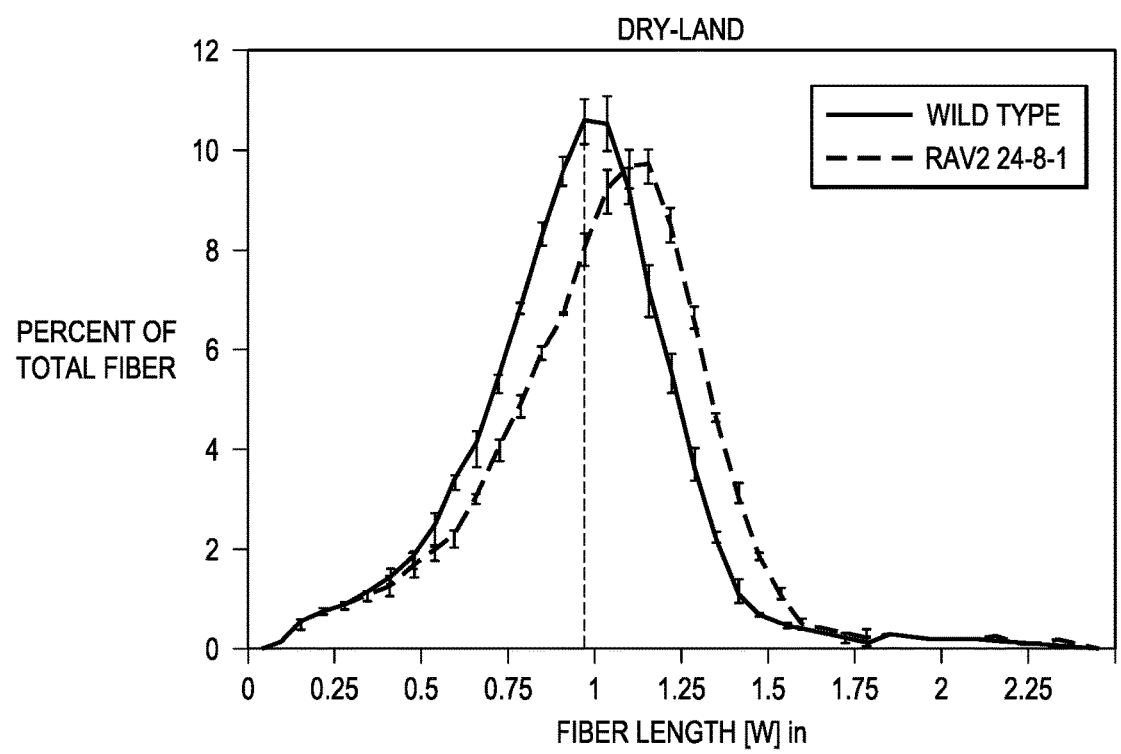
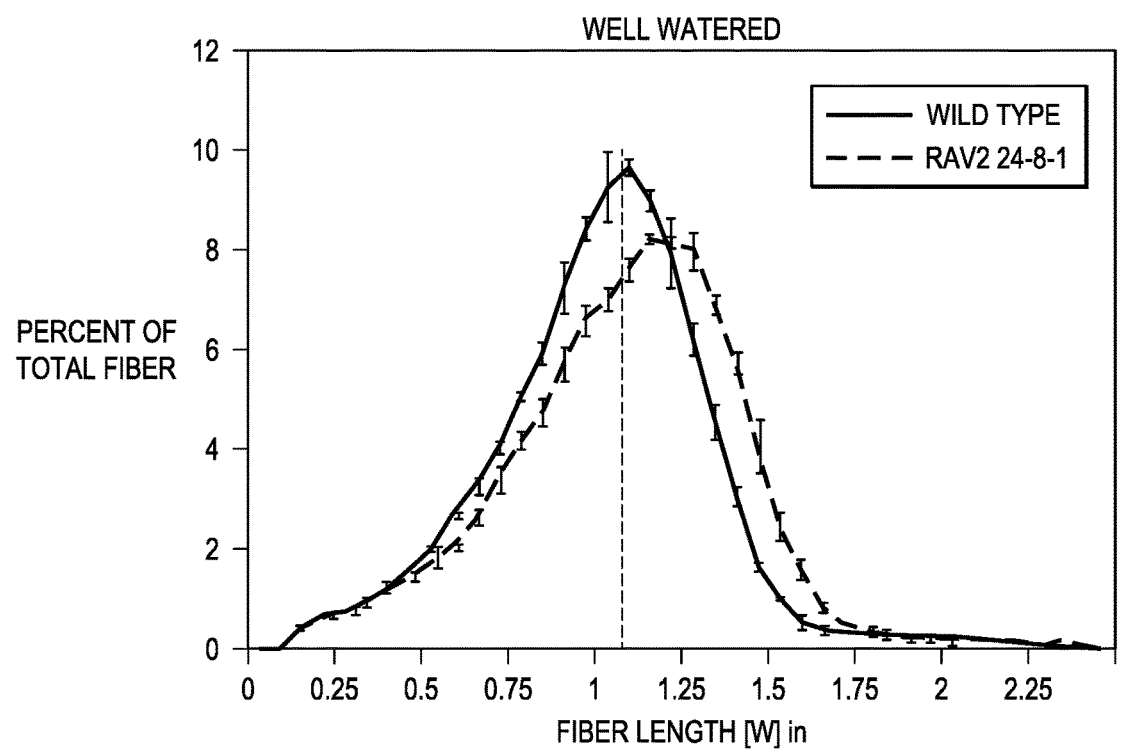

TRANSCRIPTION FACTORS AND METHOD FOR INCREASED FIBER LENGTH OF COTTON

TECHNICAL FIELD OF THE INVENTION

The present invention relates in general to the field of improved cotton (*Gossypium* spp), and more particularly, to compositions and methods for increasing the length of cotton fibers.

BACKGROUND OF THE INVENTION

Without limiting the scope of the invention, its background is described in connection with cotton fibers.

There is a longstanding problem of an inverse relationship between cotton fiber qualities versus high yields. To date, there is no evidence that the longstanding inverse relationship observed between fiber quality and yield can be broken, especially under drought stress, a pressing and growing problem in the face of climate change.

U.S. Pat. No. 8,541,665, issued to Jiang, et al., is entitled "Polynucleotides and polypeptides in plants." According to the inventors, the invention relates to plant transcription factor polypeptides, polynucleotides that encode them, homologs from a variety of plant species, and methods of using the polynucleotides and polypeptides to produce transgenic plants having advantageous properties compared to a reference plant. Sequence information related to these polynucleotides and polypeptides is said to be useful for bioinformatic search methods.

U.S. Pat. No. 8,492,618, issued to Bourland is entitled "Cotton cultivar UA-48." According to the inventor, the invention relates to the seeds of cotton cultivar UA-48, to the plants of cotton UA-48 and to methods for producing a cotton plant produced by crossing the cultivar UA-48 with itself or another cotton variety. The invention is also said to relate to hybrid cotton seeds and plants produced by crossing the cultivar UA-48 with another cotton cultivar.

U.S. Pat. No. 8,283,519, issued to Creelman, et al., is entitled "Plant transcriptional regulators of abiotic stress." According to the inventor, the invention relates to plant transcription factor polypeptides, polynucleotides that encode them, homologs from a variety of plant species, variants of naturally-occurring sequences, and methods of using the polynucleotides and polypeptides to produce transgenic plants having advantageous properties, including improved cold and other osmotic stress tolerance, as compared to wild-type or reference plants. The invention is also said to pertain to expression systems that may be used to regulate these transcription factor polynucleotides, providing constitutive, transient, inducible and tissue-specific regulation.

U.S. Pat. No. 7,446,241, issued to Rock, et al., is entitled "Transcription factors, DNA and methods for introduction of value-added seed traits and stress tolerance." This patent teaches that abscisic acid-(ABA) inducible gene expression in different plant tissues is enhanced synergistically by the co-expression of a B3-domain transcription factor and various bZIP-domain transcription factors, or a different B3-domain transcription factor. Using these transcription factors in novel formulations in plants confers value-added traits to transgenic plants, including, but not limited to, higher levels of heterologous gene expression, drought and salt tolerance, viability and productivity under stress, enhanced nutrient reserves and seed properties.

United States Patent Application No. 20110277190, filed by Abad is entitled "Transgenic Plants With Enhanced Agronomic Traits." This applicant states that the application relates to transgenic plant cells with recombinant DNA for expression of proteins that are useful for imparting enhanced agronomic trait(s) to transgenic crop plants. The invention is also said to provide transgenic plants and progeny seed comprising the transgenic plant cells where the plants are selected for having an enhanced trait selected from the group of traits consisting of enhanced water use efficiency, enhanced cold tolerance, increased yield, enhanced nitrogen use efficiency, enhanced seed protein and enhanced seed oil. It is also said to disclose methods for manufacturing transgenic seed and plants with enhanced traits.

SUMMARY OF THE INVENTION

In one embodiment, the present invention includes a seed of cotton cultivar recombinantly modified that overexpresses at least one of AtRAV1 or AtRAV2 or orthologs thereof to confer longer fibers to transgenic cotton plants grown under drought conditions. In another aspect, the parent cotton cultivar is Coker 312, UA-48, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala picker Siokra, stripper variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6, ORO BLANCO PIMA, AXTE1, NM2302, C6TE, NM B3080, C6TE, NM B3080, AXTE 1-57, TEX E364, S196, 1900-1, 12302-4, C6TE, B7378, ATE-11, NM49-2, C6TE or NM B3080. In another aspect, the plant further overexpresses AtABI5. In another aspect, the modifications further comprise delayed flowering. In another aspect, the AtRAV1 or AtRAV2 or orthologs thereof are from dicotyledonous plant selected from the group consisting of soybean, cotton, canola, and potato. In another aspect, the orthologs have a homology of 90%, 91%, 92%, 93%, 94%, 95%, 96%, 97%, 98%, 99% or greater sequence identity with the AtRAV1 and/or AtRAV2 genes of cotton plants.

In another embodiment, the present invention includes a cotton plant, or a part thereof, produced by growing the seed that is recombinantly modified to overexpress at least one of AtRAV1 or AtRAV2 or orthologs thereof to confer longer fibers to transgenic cotton plants grown under drought conditions.

In another embodiment, the present invention includes a tissue culture of cells produced from the plant that is recombinantly modified to overexpress at least one of AtRAV1 or AtRAV2 or orthologs thereof to confer longer fibers to transgenic cotton plants grown under drought conditions, wherein said cells of the tissue culture are produced from a plant part selected from the group consisting of leaves, pollen, embryos, cotyledons, hypocotyl, meristematic cells, roots, root tips, pistils, anthers, flowers, and stems.

In another embodiment, the present invention includes a protoplast produced from the plant that is recombinantly modified to overexpress at least one of AtRAV1 or AtRAV2 or orthologs thereof to confer longer fibers to transgenic cotton plants grown under drought conditions.

In another embodiment, the present invention includes a protoplast produced from the tissue culture that is recombinantly modified to overexpress at least one of AtRAV1 or AtRAV2 or orthologs thereof to confer longer fibers to transgenic cotton plants grown under drought conditions.

In another embodiment, the present invention includes a cotton plant regenerated from the tissue culture that is recombinantly modified to overexpress at least one of AtRAV1 or AtRAV2 or orthologs thereof to confer longer fibers to transgenic cotton plants grown under drought conditions, wherein the plant has all of the morphological and physiological characteristics of conferring longer fibers to transgenic cotton plants with a yield equivalent to cotton cultivar UA-48.

In another embodiment, the present invention includes a method for producing an $F_1$ hybrid cotton seed, wherein the method comprises crossing the plant, which is recombinantly modified to overexpress at least one of AtRAV1 or AtRAV2 or orthologs thereof to confer longer fibers to transgenic cotton plants grown under drought conditions, with a different cotton plant and harvesting the resultant $F_1$ hybrid cotton seed. In another embodiment, the present invention includes a hybrid cotton seed produced by the method.

In another embodiment, the present invention includes a hybrid cotton plant, or a part thereof, produced by growing said hybrid seed is recombinantly modified to overexpress at least one of AtRAV1 or AtRAV2 or orthologs thereof to confer longer fibers to transgenic cotton plants grown under drought conditions with a different cotton plant and harvesting the resultant $F_1$ hybrid cotton seed.

In another embodiment, the present invention includes a method of producing an insect resistant cotton plant, wherein the method comprises transforming the cotton plant that is recombinantly modified to overexpress at least one of AtRAV1 or AtRAV2 or orthologs thereof to confer longer fibers to transgenic cotton plants grown under drought conditions with a different cotton plant and harvesting the resultant $F_1$ hybrid cotton seed with a transgene that confers insect resistance. An insect resistant cotton plant that is recombinantly modified to overexpress at least one of AtRAV1 or AtRAV2 or orthologs thereof to confer longer fibers to transgenic cotton plants grown under drought conditions with a different cotton plant and harvesting the resultant $F_1$ hybrid cotton seed. In one aspect, the transgene encodes a *Bacillus thuringiensis* endotoxin.

In another embodiment, the present invention includes a method of producing a disease-resistant cotton plant, wherein the method comprises transforming the cotton plant that is recombinantly modified to overexpress at least one of AtRAV1 or AtRAV2 or orthologs thereof to confer longer fibers to transgenic cotton plants grown under drought conditions with a different cotton plant and harvesting the resultant $F_1$ hybrid cotton seed with a transgene that confers disease resistance. A disease-resistant cotton plant produced by the method described.

In another embodiment, the present invention includes a method of producing a cotton plant with longer fibers and delayed flowering to transgenic cotton plants under drought conditions, wherein the method comprises transforming the cotton plant that overexpresses at least one of AtRAV1 or AtRAV2 with a transgene that overexpresses AtRAV1 and AtRAV2 or orthologs thereof, wherein the transgenic cotton ovules produce longer lint of higher quality without significant reductions in yield.

In another embodiment, the present invention includes a cotton plant that overexpresses at least one of AtRAV1 or AtRAV2 or orthologs thereof produced by the described method. In one aspect, fiber obtained from the plant is spun into stronger and more uniform yarn that from the parent cultivar when both are grown under drought conditions.

In another embodiment, the present invention includes a method of introducing a desired trait into cotton cultivar Coker 312, wherein the method comprises: (a) crossing a Coker 312, wherein a representative sample of seed, with a plant of another cotton cultivar that overexpresses at least one of AtRAV1 or AtRAV2 or orthologs thereof to produce a desired trait to produce progeny plants wherein the desired trait is transgenic cotton ovules that produce longer lint of higher quality without significant reductions in yield; (b) selecting one or more progeny plants that have the desired trait; (c) backcrossing the selected progeny plants with the Coker 312 plant to produce backcross progeny plants; (d) selecting for backcross progeny plants that have the desired trait; and (e) repeating steps (c) and (d) two or more times in succession to produce selected third or higher backcross progeny plants that comprise the desired trait and all of the physiological and morphological characteristics of cotton cultivar Coker 312 that produce longer lint of higher quality without significant reductions in yield. In one aspect, the plant further overexpresses AtABI5.

BRIEF DESCRIPTION OF THE DRAWINGS

For a more complete understanding of the features and advantages of the present invention, reference is now made to the detailed description of the invention along with the accompanying figures and in which:

In FIG. 3 a single asterisk (*) suffix in genotype name indicates plants were sown by hand at low density (two plants per foot), resulting in two different control (w.t.) conditions. Double asterisks (**) above bars indicates significantly different (p<0.001) than wild type control; (*) indicates significantly different (p<0.05). Error bars are SEM (n=3 plots).

FIG. 5 shows the fiber lengths (stripper harvested) of select line AtRAV2$^{24-8-1}$ compared to conventional breeding elite variety 'UA48' and checks 'Arkot8712' and DP1044, subjected to deficit irrigation or dryland drought stress regimes in the field in 2012. Error bars are SEM, n=3 except DP1044 (n=1) and Coker312 (n=6). Asterisks (**) indicates significantly different than control, P<0.005; (*) indicates P<0.05. For AtRAV2 Well Watered, P=0.07.

FIGS. 6a-6c show the yarn quality parameters of spun fibers from field-grown AtRAV1 and AtRAV2 transgenics subjected to drought conditions. Note that the dryland Coker312 sample failed to spin (N/A), due to low quality fibers. FIG. 6a: work to break (grams force per cm). FIG. 6b shows uniformity (mass variation) measured as Coefficient of Variance. FIG. 6c shows imperfections/km length. Error bars are SEM, n=10. Three asterisks (*) indicates highly significantly different (P<0.00001) than Coker312; () indicates significantly different (P<0.001); (*) indicates P<0.05. In panel c: P=0.07 for RAV2$^{4-8-1}$, and P=0.11 for RAV1$^{13-7-2}$ for Well-Watered treatment samples.

FIGS. 7a-7c show seed cotton (in boll) yield data for 2013-2011 field trials (FIGS. 7a-7c, respectively) of AtRAV1 and AtRAV2 transgenics under deficit or dryland irrigation, with conventional breeding elite variety 'UA48' and checks 'Arkot8712' and DP1044. Error bars are SEM, n=3. Asterisks (*) indicates highly significantly different (p<0.00001) than Coker312; () indicates p<0.005; (*) indicates p<0.05.

FIG. 8a is an RNA blot assay of wild type, AtRAV1 and AtRAV2 transgenic cotton for G. hirsutum Flowering Locus T-Like (GhFTL) homologue as function of time (Days After Sowing, DAS). Band intensities were quantified and are presented as a normalized ratio (FTL/UBQ internal control) relative to the genotype at 24 DAS (set to unity). "DAS ratio" compares the relative normalized abundance of GhFTL over time. "RAV1 (and RAV2)/WT" refers to normalized signal ratio of FTL expression in transgenics compared to wild type at corresponding DAS. GhFTL relative expression was further quantified independently by two different q-RT-PCR primer pairs (normalized to GhHistone H3), and averaged results are shown in the panel below the RNA blot ratios. The Pearson correlation coefficient for DAS timecourse between blot quantification and q-RT-PCR was 0.97. FIG. 8b shows GhFTL expression in response to drought stress and recovery after watering. For transgenic lines, RAV1=13-7-2, RAV2=24-8-1, ABI5=13-4-1, RAV1×ABI5 (13-7-2×13-4-1), and RAV2×ABI5 (4-8-1×13-4-1). "Genotype/WT" in specified treatment refers to the ratio of normalized FTL signal in transgenic line compared to wild type for each specified treatment. "Drought/WW" refers to the ratio of signal in response to drought relative to well-watered control. "Rewater/Drt" refers to the signal ratio in individual line in response to re-watering relative to drought treatment. "Rewater/WW" refers to signal ratio after re-watering relative to respective well-watered plants.

FIG. 10c=MYB25; FIG. 10d=MYB25L), and GhRDL1 (FIG. 10e) involved in fiber cell initiation or elongation in AtRAV1 and AtRAV2 transgenics and control Coker312. Error bars are SEM for two biological (-3, 0, 3, 5, and 15 DPA) and three technical replicates. Asterisk (*) indicates significantly different (p</=0.05) than Wild Type; cross (†) indicates p<0.07. For RDL1 and RAV2L, normalized to 0 DPA=1.

FIG. 11 is a histogram of fiber length measurements for select AtRAV overexpression cotton line subjected to (a) deficit irrigation or (b) well-watered conditions in the field, compared to control Coker312.

DETAILED DESCRIPTION OF THE INVENTION

Figure 1A:
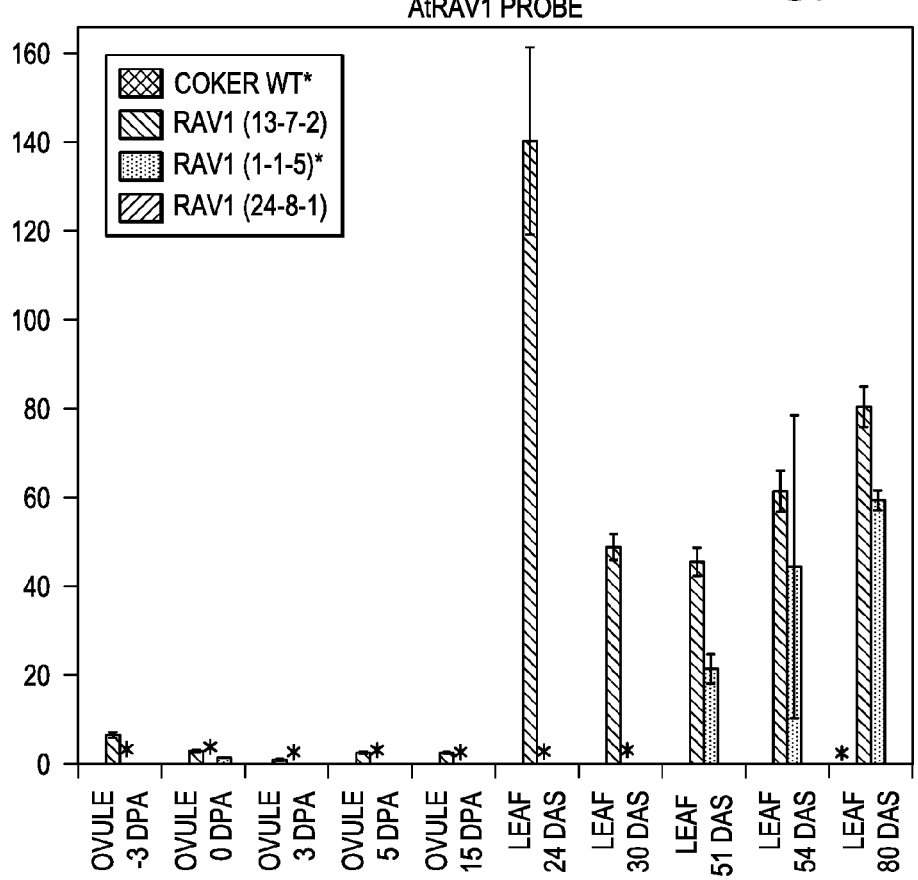
FIGS. 1a and 1b are Quantitative Real Time PCR (q-RT-PCR) of AtRAV1 (a) and AtRAV2 (b) overexpression in ovule and leaf tissues at various developmental stages for independent transformant events (line number in parentheses), normalized to 3 Days Post Anthesis (3 DPA=1) with RAV1$^{13\text{-}7\text{-}2}$ (FIG. 1a) or RAV2$^{24\text{-}8\text{-}1}$ (FIG. 1b). Asterisks (*) indicate "not analyzed." Error bars are SEM of three technical replicates.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Definitions

In the description and data that follow, a number of terms are used. In order to provide a clear and consistent understanding of the specification and claims, including the scope to be given such terms, the following definitions are provided:

Allele. Allele is any of one or more alternative forms of a gene, all of which relate to one trait or characteristic. In a diploid cell or organism, the two alleles of a given gene occupy corresponding loci on a pair of homologous chromosomes. In a tetraploid cell or organism, such as G. hirsutum or G. barbadense, which are allotetraploid, there may be four homeologous alleles.

Backcrossing. Backcrossing is a process in which a breeder repeatedly crosses hybrid progeny back to one of the parents, for example, a first generation hybrid F$_1$ with one of the parental genotypes of the F$_1$ hybrid.

Disease Resistance. As used herein, the term "disease resistance" is defined as the ability of plants to restrict the activities of a specified pest, such as an insect, fungus, virus, or bacterial.

Disease Tolerance. As used herein, the term "disease tolerance" is defined as the ability of plants to endure a specified pest (such as an insect, fungus, virus or bacteria) or an adverse environmental condition and still perform and produce in spite of this disorder.

Essentially all of the physiological and morphological characteristics. Essentially all of the physiological and morphological characteristics refers to a plant having essentially all of the physiological and morphological characteristics of the recurrent parent, except for the characteristics derived from the converted trait.

Elongation (E1). As used herein, the term "elongation" is defined as the measure of elasticity of a bundle of fibers as measured by High Volume Instrumentation (HVI).

Length. As used herein, the term "length" is defined as 2.5% span length in inches of fiber as measured by HVI.

Fiber Strength (T1). As used herein, the term "strength" is defined as the force required to break a bundle of fibers as measured in grams per millitex on the HVI.

Fruiting Nodes. As used herein, the term "fruiting nodes" is defined as the number of nodes on the main stem from which arise branches that bear fruit or bolls.

Gin Turnout. As used herein, the term "gin turnout" is defined as a fraction of lint in a machine harvested sample of seed cotton (lint, seed, and trash).

Homology. As used herein, the phrase "homology" or "homologous" refers to polynucleotide molecules that generally demonstrate a substantial percent sequence identity with the regulatory polynucleotides provided herein. Substantially homologous polynucleotide molecules include polynucleotide molecules that function in plants and plant cells to direct transcription and have at least about at least about 90% sequence identity, or even greater sequence identity, specifically including about 90%, 91%, 92%, 93%, 94%, 95%, 96%, 97%, 98%, 99% or greater sequence identity with the AtRAV1 and/or AtRAV2 genes from, e.g., cotton plants.

Lint/Boll. As used herein, the term "lint/boll" is the weight of lint per boll.

Lint Index. As used herein, the term "lint index" refers to the weight of lint per seed in milligrams.

Lint Percent. As used herein, the term "lint percent" is defined as the lint (fiber) fraction of seed cotton (lint and seed). Also known as lint turnout.

Maturity. As used herein, the term "maturity" is defined as the HVI machine rating which refers to the degree of development of thickening of the fiber cell wall relative to the perimeter or effective diameter of the fiber.

Micronaire. As used herein, the term "micronaire" is defined as a measure of the fineness of the fiber. Within a cotton cultivar, micronaire is also a measure of maturity. Micronaire differences are governed by changes in perimeter or in cell wall thickness, or by changes in both. Within a cultivar, cotton perimeter is fairly constant and maturity will cause a change in micronaire.

Consequently, micronaire has a high correlation with maturity within a variety of cotton. Maturity is the degree of development of cell wall thickness. Micronaire may not have a good correlation with maturity between varieties of cotton having different fiber perimeter. Micronaire values range from about 2.0 to 6.0.

Ortholog. As used herein, the term "ortholog" refers to a polynucleotide from a different species that encodes a similar protein that performs the same biological function. For example, genes that encode a certain nucleic acid binding protein from, for example, *Arabidopsis* and rice, are orthologs. Orthologs may also exhibit similar tissue expression patterns (for example, constitutive expression in plant cells or plant tissues). Often, orthologous nucleotide sequences are characterized by significant sequence similarity. A nucleotide sequence of an ortholog in one species (for example, *Arabidopsis*) can be used to isolate the nucleotide sequence of the ortholog in another species (for example, rice) using standard molecular biology techniques.

Plant Height. As used herein, the term "plant height" is defined as the average height in inches or centimeters of a group of plants.

Promoter. As used herein, the term "promoter" refers to a region of a regulatory polynucleotide required to properly initiate transcription. A "core" promoter typically has the transcription start site (TSS), a binding site for RNA polymerase, and general transcription factor binding sites. Core promoters can include promoters produced through the manipulation of known core promoters to produce artificial, chimeric, or hybrid promoters, and can be used in combination with other regulatory elements, such as cis-elements, enhancers, or introns, for example, by adding a heterologous regulatory element to an active core promoter with its own partial or complete regulatory elements. For use with the present invention constitutive promoter may be used, or regulated promoters may be used depending on the tissues or timing of the expression required.

Regulatory elements. As used herein, the terms "regulatory element" refers to polynucleotide molecules having regulatory activity on the transcription of an operably linked transcribable polynucleotide. The terms is used to describe polynucleotide molecule sequences or regions containing one or more elements such as core promoter regions, cis-elements, leaders or untranslated regions (UTRs), enhancers, introns, and transcription termination regions, all of which have regulatory activity and may play a role in the overall expression of nucleic acid molecules in living cells. The "regulatory elements" determine if, when, and at what level a particular polynucleotide is transcribed. The regulatory elements may interact with regulatory proteins or other proteins or be involved in nucleotide interactions, for example, to provide proper folding of a regulatory polynucleotide.

Seed/boll. As used herein, the term "seed/boll" refers to the number of seeds per boll.

Seedcotton/boll. As used herein, the term "seedcotton/boll" refers to the weight of seedcotton per boll.

Seed cotton yield. As used herein, the term "Seed cotton yield" is defined as the measure of the quantity of fiber and seed produced on a given unit of land. Presented below in pounds of lint plus seed per acre.

Single Trait Converted (Introgression). Single trait converted (conversion) plant refers to plants which are developed by a plant breeding technique called backcrossing or via genetic engineering wherein essentially all of the desired morphological and physiological characteristics of a variety are recovered in addition to the single trait transferred into the variety via the backcrossing technique or via genetic engineering.

Vegetative Nodes. As used herein, the term "vegetative nodes" is defined as the number of nodes from the cotyledonary node to the first fruiting branch on the main stem of the plant.

When the term "cotton plant" is used in the context of the present invention, this also includes any single gene conversions of that variety. The term "single gene converted plant" as used herein refers to those cotton plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental cotton plant which contributes the gene for the desired characteristic is termed the "nonrecurrent" or "donor parent". This terminology refers to the fact that the nonrecurrent parent is used one time in the backcross protocol and therefore does not recur. The parental cotton plant to which the gene or genes from the nonrecurrent parent are transferred is known as the recurrent parent as it is used for several rounds in the backcrossing protocol (Poehlman & Sleper [1994]; Fehr [1987], relevant portions incorporated herein by reference). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a cotton plant is obtained wherein essentially all of the desired morphological and physiological characteristics of the recurrent parent are recovered in the converted plant, in addition to the single transferred gene from the nonrecurrent parent, as determined at the 5% significance level when grown in the same environmental conditions.

The selection of a suitable recurrent parent is an important step for a successful backcrossing procedure. The goal of a backcross protocol is to alter, substitute, or add a single trait or characteristic to the original variety. In general, a single gene of the recurrent variety is modified, substituted by crossing in (adding) the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait, for example a single gene locus or cassette of transgenes integrated as a single genetic locus, to the plant. The exact backcrossing protocol will depend on the characteristic or trait being altered to determine an appropriate testing protocol. Although backcrossing methods are simplified when the characteristic being transferred is a dominant allele such as an engineered transgene, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic. Examples of these traits include but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus. Several of these single gene traits are described in U.S. Pat. Nos. 5,959,185; 5,973,234; and 5,977,445, the disclosures of which are specifically hereby incorporated by reference.

Further reproduction of the variety can occur by tissue culture and regeneration. Tissue culture of various tissues of cotton and regeneration of plants therefrom is well known and widely published. For example, reference may be had to Komatsuda, T., et al., Crop Sci., 31:333-337 (1991); Stephens, P. A., et al., Theor. Appl. Genet., 82:633-635 (1991); Komatsuda, T., et al., Plant Cell, Tissue and Organ Culture, 28:103-113 (1992); Dhir, S., et al. Plant Cell Rep., 11:285-289 (1992); Pandey, P., et al., Japan J. Breed., 42:1-5 (1992); and Shetty, K., et al., Plant Science, 81:245-251 (1992); as well as U.S. Pat. No. 5,024,944 issued Jun. 18, 1991 to Collins, et al., and U.S. Pat. No. 5,008,200 issued Apr. 16, 1991 to Ranch, et al., relevant portions of each incorporated herein by reference. Thus, another aspect of this invention is to provide cells, which upon growth and differentiation, produce cotton plants having the physiological and morphological characteristics of cotton cultivar that overexpresses AtRAV1 and/or AtRAV2.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185; 5,973,234; and 5,977,445, described certain techniques, relevant portions of each incorporated herein by reference.

This invention also is directed to methods for producing a cotton plant by crossing a first parent cotton plant with a second parent cotton plant wherein the first or second parent cotton plant is a cotton plant of the cultivar wherein the transgenic cotton ovules produce longer lint of higher quality without significant reductions in yield. Further, both first and second parent cotton plants can come from the cotton cultivar that overexpresses AtRAV1 and/or AtRAV2. Additionally, the first or second parent cotton plants can be either *Gossypium hirsutum* or *Gossypium barbadense*, or any other cotton plant. Thus, any such methods using the cotton cultivar that overexpresses AtRAV1 and/or AtRAV2 are part of this invention: selfing, backcrosses, hybrid production, crosses to populations, and the like. All plants produced using cotton cultivars that overexpresses AtRAV1 and/or AtRAV2 as a parent are within the scope of this invention, including those developed from varieties derived from cotton cultivar that overexpresses AtRAV1 and/or AtRAV2. Advantageously, the cotton cultivar could be used in crosses with other, different, cotton plants to produce first generation ($F_1$) cotton hybrid seeds and plants with superior characteristics. The other, different, cotton plants may be *Gossypium hirsutum* or *Gossypium barbadense* or another cotton cultivar. The cultivar of the invention can also be used for transformation where exogenous genes are introduced and expressed by the cultivar of the invention. Genetic variants created either through traditional breeding methods using a cultivar that overexpresses AtRAV1 and/or AtRAV2 or through transformation of vectors designed to overexpress AtRAV1 and/or AtRAV2 in specific tissues or in response to internal or external cues by any of a number of protocols known to those of skill in the art are intended to be within the scope of this invention.

The following describes breeding methods that may be used with a cultivar that overexpresses AtRAV1 and/or AtRAV2 in the development of further cotton plants. One such embodiment is a method for developing an overexpresser of AtRAV1 and/or AtRAV2 progeny cotton plant in a cotton plant breeding program comprising: obtaining the cotton plant, or a part thereof, of a cultivar that overexpresses AtRAV1 and/or AtRAV2, utilizing said plant or plant part as a source of breeding material, and selecting a progeny plant that overexpresses AtRAV1 and/or AtRAV2 with molecular markers in common with an overexpresser of AtRAV1 and/or AtRAV2 and/or with morphological and/or physiological characteristics selected from the characteristics listed in Tables 1 or 2. Breeding steps that may be used in the cotton plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of cultivar that overexpresses AtRAV1 and/or AtRAV2 progeny cotton plants, comprising crossing the cultivar that overexpresses AtRAV1 and/or AtRAV2 with another cotton plant, thereby producing a population of cotton plants, which, on average, derive 50% of their alleles from cultivar that overexpresses AtRAV1 and/or AtRAV2. The other cotton plant may be Gossypium hirsutum or Gossypium barbadense or any other cotton plant. A plant of this population may be selected and repeatedly selfed or sibbed with a cotton cultivar resulting from these successive filial generations. One embodiment of this invention is the cotton cultivar produced by this method and that has obtained at least 50% of its alleles from the cultivar that overexpresses AtRAV1 and/or AtRAV2.

One of ordinary skill in the art of plant breeding would know how to evaluate the traits of two plant varieties to determine if there is no significant difference between the two traits expressed by those varieties. For example, see Fehr and Walt, Principles of Cultivar Development, pp. 261-286 (1987). Thus, the invention includes cotton a cultivar that overexpresses AtRAV1 and/or AtRAV2 progeny cotton plants comprising, wherein the transgenic cotton ovules produce longer lint of higher quality without significant reductions in yield, so that said progeny cotton plant is not significantly different for said traits than a cotton cultivar that overexpresses AtRAV1 and/or AtRAV2 as determined at the 5% significance level when grown in the same environment. Using techniques described herein, molecular markers may be used to identify said progeny plant as a progeny plant that overexpresses AtRAV1 and/or AtRAV2. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of a cultivar that overexpresses AtRAV1 and/or AtRAV2 may also be characterized through their filial relationship with a cotton cultivar that overexpresses AtRAV1 and/or AtRAV2, as for example, being within a certain number of breeding crosses of cotton cultivar that overexpresses AtRAV1 and/or AtRAV2. A breeding cross is a cross made to introduce new genes into the progeny, and is distinguished from a cross, such as a self or a sib cross, made to select among existing genetic alleles. The lower the number of breeding crosses in the pedigree, the closer the relationship between cotton cultivar that overexpresses AtRAV1 and/or AtRAV2 and its progeny. For example, progeny produced by the methods described herein may be within 1, 2, 3, 4 or 5 breeding crosses of cotton cultivar that overexpresses AtRAV1 and/or AtRAV2.

As used herein, the term "plant" includes plant cells, plant protoplasts, plant cell tissue cultures from which cotton plants can be regenerated, plant calli, plant clumps, and plant cells that are intact in plants or parts of plants, such as embryos, pollen, ovules, flowers, leaves, roots, root tips, anthers, pistils, and the like.

There is a longstanding problem of an inverse relationship between cotton fiber qualities versus high yields. To better understand drought stress signaling and adaptation in cotton (Gossypium hirsutum) fiber development, the present inventors expressed the Arabidopsis transcription factors RELATED_TO_ABA-INSENSITIVE3/VIVIPAROUS1/(RAV1) (Genbank Accession No. NM_101197.3) and AtRAV2 (Genbank Accession No. NM_105558.2), which encode APETALA2-Basic3 domain proteins shown to repress transcription of FLOWERING_LOCUS_T (FT) and to promote stomatal opening cell-autonomously. In three years of field trials, the inventors show that AtRAV1 and AtRAV2-overexpressing cotton had ~5% significantly longer fibers with only marginal decreases in yields under well-watered or drought stress conditions that resulted in 40-60% yield penalties and 3-7% fiber length penalties in control or empty vector plants. The longer transgenic fibers from drought-stressed transgenics could be spun into yarn which was measurably stronger and more uniform than that from well-watered control fibers. The transgenic AtRAV1 and AtRAV2 lines flowered later and retained bolls at higher nodes, which correlated with repression of endogenous GhFT-Like (FTL) transcript accumulation. Elevated expression early in development of ovules was observed for GhRAV2L, GhMYB25-Like (MYB25L) involved in fiber initiation, and GhMYB2 and GhMYB25 involved in fiber elongation. Altered expression of RAVs controlling critical nodes in developmental and environmental signaling hierarchies has the potential for phenotypic modification of crops.

Seed epidermal cells of cotton are the most important source of spinnable fiber (Arpat et al. 2004). Cotton fibers share many similarities with leaf trichomes for cell fate determination (Guan et al. 2014) and are a good model system for understanding plant cellular processes such as differentiation and elongation, carbon partitioning to cellulose sinks, and signaling between maternal and embryonic tissues. Fiber cells initiate three days before anthesis and undergo rapid elongation at approximately 3-18 days post anthesis (DPA) (Kim & Triplett 2001). Negative correlations exist between cotton fiber fineness and strength, and for in-boll yields versus fiber length (Culp & Harrell 1975), representing longstanding bottlenecks for breeders which, in addition to a narrow germplasm base and allopolyploidy, pose challenges potentially addressed by genetic engineering. Fiber quality is a key trait because immature or coarse fibers caused by stress results in poor yarn spinning performance and marketability. Sustainable cotton production is the ultimate challenge facing farmers drawing on the southern Ogallala Aquifer, a non-renewable resource where 90% of groundwater used in the southern High Plains produces one-third of all cotton in the U.S. (Braxton-Little 2009).

Basic3 (B3) domain transcription factors (TFs) are unique to plants. The cognates of the family, maize Viviparous1 (VP1) (McCarty et al. 1991) and Arabidopsis orthologue ABSCISIC ACID-INSENSITIVE3 (ABI3) (Giraudat et al. 1992), physically and functionally interact with basic-leucine-zipper TFs of the ABI5 clade (Finkelstein et al. 2005; Hobo et al. 1999) in hierarchical control of TFs controlling seed and seedling growth (Lumba et al. 2014). In Arabidopsis there are over 100 B3-class TFs, with two homologues of the RELATED TO ABA-INSENSITIVE3/VIPAROUS1 (RAV) clade defining the eudicot-specific Group I APETALA2-Basic3 (AP2-B3) family (Wang et al. 2012d). RAVs bind as monomers to bipartite sequence motifs that contain consensus elements for both the AP2 and B3 domains (Kagaya et al. 1999). RAVs contain a R/KLFGV conserved motif that functions as a repression domain (Ikeda & Ohme-Takagi 2009). AtRAV2-Like (RAV2L) and RAV1 physically interact with TOPLESS (TPR) corepressors that facilitate recruitment of histone deacetylases and methyltransferases (Causier et al. 2012). AtRAV2L has been shown to be an integrator of internal (brassinosteroid, auxin) and external (blue light) signals in hypocotyl physiology (Choi et al. 2013). RAV2 is required for induction of many genes involved in stress and defense pathways in different species (Endres et al. 2010; Li et al. 2011). RAVs have also been described as ethylene response DNA-binding factors and are induced by numerous stimuli (Chen et al. 2009; Kagaya & Hattori 2009). Previous characterization of RAV functions in brassinosteroid response (Hu et al. 2004; Je et al. 2010), reactive oxygen species scavenging (Lee et al. 2010), suppression of RNA silencing by viruses (Endres et al. 2010), control of flowering time (Castillejo & Pelaz 2008; Lu et al. 2014; Mutasa-Gottgens et al. 2012; Osnato et al. 2012; Sgamma et al. 2014), sylleptic tree branching (Moreno-Cortes et al. 2012), cytokinin signaling (Zhao et al. 2012), senescence (Woo et al. 2010; Zhao et al. 2008), and salt tolerance (Fu et al. 2014; Min et al. 2014) support the function of RAVs as nodes in crosstalk networks integrating external and internal signals (Matias-Hernandez et al. 2014).

Drought is the most important environmental stress affecting agriculture. Plants growing in environments subjected to abiotic stresses do not meet their genetic potential and suffer yield penalties (Boyer 1982). Stresses tend to induce early flowering through an elaborate network of floral signaling pathways (Riboni et al. 2013). In *Arabidopsis* the RAV2 and RAV2L genes (also named TEMPRANILLO2 [TEM2] and TEM1, respectively) are important modulators of flowering time via direct repression of the "florigen" component FLOWERING LOCUS T (FT; AT1G65480) (Castillejo & Pelaz 2008) a small protein that moves from leaves to apical meristems. Ectopic expression of AtFT in photoperiodic cotton increases determinate plant growth, affects sympodial growth to promote compact architecture, and overcomes photoperiodism (McGarry & Ayre 2012; McGarry et al. 2013). AtRAV2/TEM2 and AtRAV2L/TEM1 bind GIGANTEA (GI) to effect AtFT repression (Sawa & Kay 2011). AtFT is regulated positively by CONSTANS (CO) (the output of the photoperiod pathway), negatively by FLOWERING LOCUS C (FLC) (which integrates the vernalization pathway), and by myriad developmental programs (Deng et al. 2011) including an ABA-dependent drought escape pathway (Riboni et al. 2013) and other autonomous and light-quality pathways (Matsoukas et al. 2012). AtFT is also regulated epigenetically by histone methylation and deacetylation of chromatin (Gu et al. 2013; Jeong et al. 2009; Yang et al. 2010).

Altering the expression of regulatory genes has the potential for phenotypic modification to address global challenges such as climate change and sustainability. Although many genes are expressed during fiber development and associate with quantitative traits (Ding et al. 2014; Gilbert et al. 2014; Li et al. 2013; Liu et al. 2012; Naoumkina et al. 2014; Nigam et al. 2014; Thyssen et al. 2014; Wan et al. 2014; Wang et al. 2014a), little is known of the molecular mechanisms underlying cotton fiber initiation and elongation, and a role for the plant stress hormone abscisic acid (ABA) in the process has not been established other than by association (Gilbert et al. 2013; Yoo & Wendel 2014). Other than altered expression under greenhouse growth conditions of assimilate enzymes Sucrose Synthase (Jiang et al. 2012; Xu et al. 2012) and vacuolar Invertase (Wang et al. 2014b), or alteration of tissue-specific brassinosteroid, auxin, ethylene, gibberellin, and jasmonic acid biosynthesis, transport, or responses (Bai et al. 2014; Deng et al. 2012; Hao et al. 2012; Luo et al. 2007; Shi et al. 2006; Walford et al. 2012; Wang et al. 2013a; Yang et al. 2014; Zhang et al. 2011), there have been few reports on improving cotton fiber traits by altering expression of candidate signaling genes: GhWRINKLED1 (WRI), an AP2/EREB class TF (Qu et al. 2012); a Fasciclin-Like Arabinogalactan protein gene GhFLA1 (Huang et al. 2013a); WIDELY EXPRESSED LIN-11-Is11-MEC3-Like (GhWLIM1a), an actin remodeler/zinc finger TF influencing polyphenolic deposition during fiber maturation (Han et al. 2013; Tan et al. 2013); calcium sensor GhCaM7 (Tang et al. 2014); a peptide hormone gene GhPSK (Han et al. 2014); and Response to Drought 22-Like-1 (GhRDL1), which is transactivated by GhMYB2 (Wang et al. 2004) and interacts with expansin to control fiber wall loosening (Xu et al. 2013). The present inventors conducted three years of field trials to determine whether AtRAV1 or AtRAV2 overexpression in transgenic cotton can impact fiber initiation and elongation without compromising yields, and further characterized GhFT-Like (GhFTL) expression as a potential molecular mechanism underlying delayed flowering and improved drought-stress response traits of these lines.

Plant Materials. The transgenic lines in Coker312 genetic background (USDA Germplasm Resources Information Network #529278; PVP #007200100) were those generated previously (Mittal et al. 2014) from hypocotyl explants via *Agrobacterium tumefaciens* GV3101-mediated transformation and selection on kanamycin (Bayley et al. 1992). Briefly, pUNI51 full-length cDNA donor clones were recombined with pKYLX-pro35S:myc9::loxP binary acceptor vector (ABRC stock CD3-677)(Guo & Ecker 2003) using Cre recombinase (Jia et al. 2009a). Four independent RAV1, eight RAV2, three RAV2L, and two ABI5 transgenic events were generated and carried forward to the $T_4$ generation. $F_1$ plants from RAV×ABI5 crosses (FIG. 2, Table 2) were genotyped by PCR to verify stacked transgenes for phenotypic characterization. Homozygous transgenic plants from these lines and one kanamycin-selected non-effector transgenic (KSNT, a regenerant line 40-8-1-1 from RAV2L studies that either subsequently lost the effector DNA or was a false positive for $Kan^r$) were subjected to reverse transcriptase PCR (RT-PCR) to validate the effector transgene expression and high-expression lines were selected for further analysis (Mittal et al. 2014). A detailed expression profile of the CaMV 35S promoter in cotton showed activity in all cell and tissue types including floral parts and elongating ovule fiber (Sunilkumar et al. 2002).

Deficit irrigation treatments. Field trials were conducted at the TTU New Deal Farm south plot with subsurface drip irrigation under USDA-APHIS Notification Nos. 11-097-106n, 12-077-101n, and 13-093-105n. Mechanized sowing (4.5 seeds per foot, at least 8 foot long subplots) was carried out in a randomized block design with a zone subjected to Deficit Irrigation (DI) (¼ acre-inches water/day until flowering stage (~day 42 after sowing [DAS]), a Well-Watered (WW) control treatment zone (¼ acre-inches water/day until cutout stage ~90 DAS), and a dryland treatment (no subsurface water after stand establishment ~25 DAS). All lines tested in the field were homozygous (confirmed by PCR sampling) and were planted in paired rows with commercial genotypes (Arkot8712, DeltaPine/DP1044) as needed to minimize border effects. There were eight rows of 140 feet for each watering treatment zone, giving an overall plot of ~0.5 acre. For greenhouse studies, potting mix:field soil:

sand were mixed in 3:1:1 volume proportions and watering was withheld starting on 24 DAS. Measurements commenced on 7 days after withholding water and continued until 5 days after re-watering (10 days in total). Greenhouse plants were not watered until more than 80% of wild-type control plants did not show evening recovery from afternoon wilt. Several cycles of this treatment were repeated until 90 DAS. Tissue for GhFTL expression was collected from six greenhouse plants of each line for WW non-stressed condition (24 DAS), drought treatment (11 days of no watering; 35 DAS) and recovery (overnight recovery from drought stress after re-watering).

Fiber and seed analysis. Fiber was hand-harvested at three different node positions representing three developmental stages for fiber analysis (nodes 6-9; nodes 10-12; nodes 13 and above) and processed with a table-top 20-saw gin. For boll mapping, five plants of each genotype and water treatments having 'normal' monopod/sympod architecture were chosen. Yield in 2011 was measured by hand-harvesting representative one meter lengths of all subplot rows and weighing the lint plus seed. In 2012 and 2013, field trial yields were by weighing "burr cotton" from 40 foot- and 35 foot-long rows, respectively, harvested with a John Deere7455 two-row stripper fitted with a custom weigh system (Rusty's Weigh, Lubbock, Tex.). Fiber parameters were measured by Advanced Fiber Information System (AFIS) at the TTU Fiber and Biopolymer Research Institute. Yarn imperfections were calculated as number of places per km with a diameter greater than that of the adjoining segments (+50%) and extending for 6 mm; thin places were 50% smaller in diameter than the average diameter of the yarn. Seed protein and oil percentages were measured by combustion and petroleum ether extraction, respectively, by Eurofins Scientific (Des Moines, Iowa).

Quantitative Real Time-PCR (qRT-PCR). Total RNA was extracted using Spectrum Plant RNA Mini Kit (Sigma-Aldrich, St. Louis, Mo.). Sigma on-column DNaseI digestion was used to remove DNA contamination. Two micrograms of RNA was reverse transcribed by M-MLV reverse transcriptase (Promega) with Anchored Oligo-dT (Thermo-Scientific, Surrey, UK). 0.5 μL of cDNA template was used for a 25 μL PCR reaction. Gene-specific primers, see Table below for AtRAV1 ((Genbank Accession No. NM_101197.3/AT1G13260), AtRAV2 ((Genbank Accession No. NM_105558.2/AT1G68840), AtRAV2L (NCBI GenBank locus: AT1G25560), GhFTL (NCBI GenBank locus: HM631972), GhRAV-L/GhZM3-RAV2-Like (European Nucleotide Archive: JQ837701), GhMYB2 (NCBI GenBank locus: AY115507), GhMYB25(NCBI GenBank locus: AF336283/AY464054), GhMYB25L (NCBI GenBank HM134083.1/AY464066), and GhRDL1 (European Nucleotide Archive: AY072821.1) (Xu et al. 2013) were used to amplify cDNAs. Polyubiquitin genes (GhUBI7 (NCBI GenBank DQ116441.1)(Shi et al. 2006; Xu et al. 2013) or GhHistone3 (NCBI GenBank locus: AF024716) (Wang et al. 2004) were used as internal controls in q-RT-PCRs performed using Absolute SYBR Green Fluorescein (Thermo-Scientific) mixed with ROX Passive dye (Bio-Rad, Hercules, Calif.) on an Applied Biosystems AB7500 instrument. Statistical analyses of three technical and two biological replicates were by paired Student's t-tests (equal variance assumed; technical replicates calculated as independent variables) of ranges of normalized fold-change between wild type versus transgenic. Biological replicates vis-à-vis technical replicates were assessed directly (FIG. 10) and indirectly (FIG. 8a, FIG. 9) across the variables of tissue type (leaves, ovules), time, and genotype by q-RT-PCR on numerous endogenous genes and transgenes. Error bars represent root mean squares of standard errors of replicate internal control $deltaC_Ts$ and test $deltaC_Ts$ across two biological replicates. Oligonucleotide primers (Table 3) were designed using Primer3 design (frodo.wi.mit.edu/) and/or 'Perlprimer' (perlprimer.sourceforge.net/) and synthesized commercially (Sigma-Aldrich).

RNA blot hybridization assay. Ten micrograms of RNA was resolved on 1.2% denaturing agarose gel and blotted onto Hybond-N+ (GE Healthcare, Piscataway, N.J.). Ambion Millenium Marker (GE Healthcare) was included to estimate transcript sizes. PCR products were gel-purified and used as template for random-primed synthesis (Takara, Shiga, Japan) of radioactive probes with $[\alpha^{32}P]$-dCTP (PerkinElmer, Waltham, Mass.). PerfectHyb Plus hybridization buffer (Sigma) was used according to the manufacturer's instructions. Autoradiography was with storage phosphor screen (GE Healthcare) scanned with Storm 860 PhosphorImager. Ethidium bromide-stained RNA samples were quantified from gel images using ImageJ (imagej.nih.gov/ij/download). The RNA blot band intensity was quantified using ImageQuant TL software (v2003). The ratio of ImageQuant to ImageJ values gave normalized transcript quantities for relative comparisons.

Figure 1B:
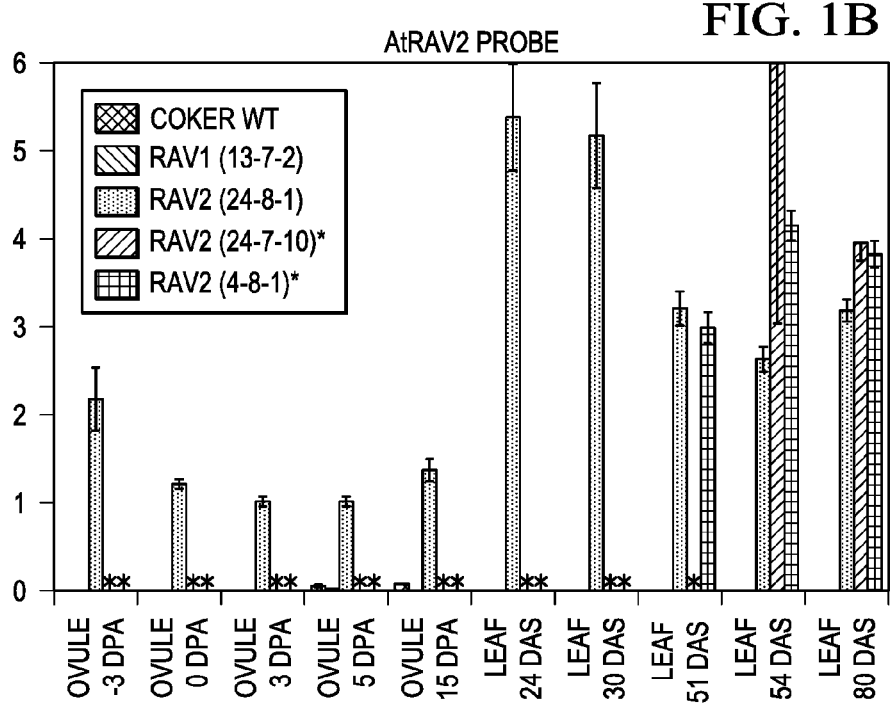

AtRAV1, AtRAV2 and AtRAV1/2×AtABI5 stacked double transgenic over-expressors have delayed flowering in well-watered and deficit irrigation conditions. The repression of AtFT by AtRAV2/TEM2 and AtRAV2L/TEM1 (Castillejo & Pelaz 2008) is consistent with others' results (Hu et al. 2004) in transgenic *Arabidopsis* demonstrating that overexpression of AtRAV1 and AtRAV2 delays flowering, and that tem1/rav2l mutants have a shorter juvenile vegetative phase (Sgamma et al. 2014). The inventors showed previously by RNA blot hybridization overexpression of AtRAV1, AtRAV2, AtRAV2L, and AtABI5 in leaves of transgenic cotton, and drought-inducible expression of endogenous GhRAV2-Like (GhRAV2L) (Mittal et al. 2014). The transgenics were quantified by qRT-PCR the degree of AtRAV1, AtRAV2, and AtRAV2L (data not shown) overexpression in leaves and developing ovules of independent transgenic lines, and the main results are shown in FIGS. 1a and 1b. Expression of AtRAV1 and AtRAV2 was higher in leaves than in ovules, and there was no cross-amplification of endogenous GhRAV2L by any AtRAV primers or between AtRAVs (FIG. 1a, 1b). Normalized expression levels were generally on par between AtRAVs and GhRAV2L (data not shown).

Figure 2A:
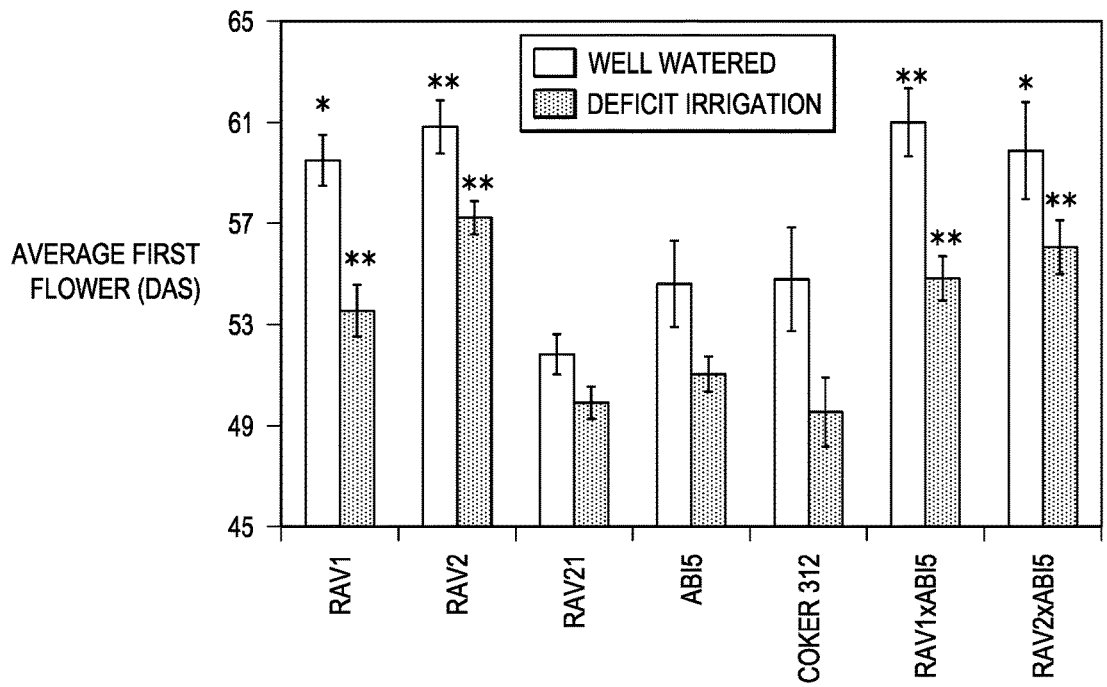
FIGS. 2a and 2b show the delayed flowering time under greenhouse conditions in AtRAV1, AtRAV2, or AtRAV1/2× ABI5 stacked transgenic cotton lines under well-watered vs. deficit irrigation (FIG. 2a) or well-watered conditions for select transgenic lines (FIG. 2b). For panel a, data for individual lines of respective transgenes were pooled (four AtRAV1, eight AtRAV2, three AtRAV2L, two AtABI5 and four stacked double transgenic AtRAVP 2×AtABI5 lines). Error bars are SEM, n=10-29 for panel a; n=6-8 for panel b except Coker312 (n=13). Asterisks (*) indicates highly significantly different (P<0.00001) than Coker312; () indicates P<0.005; (*) indicates P<0.05.
Figure 2B:
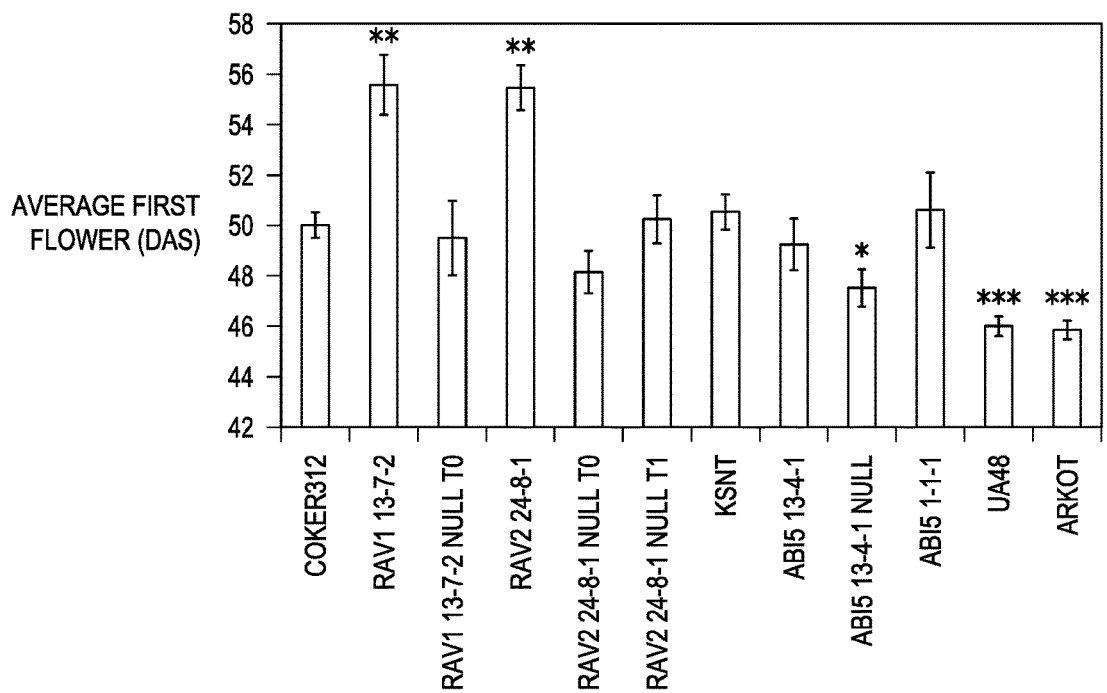

Overexpression of AtRAV1 and AtRAV2 delayed flowering in cotton, while contrary to the working hypothesis overexpression of AtRAV2L/TEM1 did not. FIGS. 2a and 2b show the results of two independent studies in the greenhouse for time of first flower (days after sowing, DAS) of transgenic lines grown under well-watered (FIG. 2b) or deficit watering conditions (FIG. 2a). Repeated imposed drought stress accelerated flowering time by four to six days in both control Coker312 and transgenic lines. Overexpression of AtRAV1 or AtRAV2 alone or stacked with an AtABI5-overexpression line resulted in delayed flowering by four to seven days under both watering regimes (FIG. 2a), whereas the high fiber quality check line UA48 (Bourland & Jones 2012) and its reference control Arkot8712 (Bourland et al. 2005) flowered two days earlier under well-watered conditions than Coker312 or a kanamycin-sensitive non-transgene control (KSNT) or siblings (null for T-DNA) from segregating transgenic stocks (FIG. 2b).

Flowering time in AtRAV1 and AtRAV2 transgenic cotton lines was also significantly delayed in field trials. Flowering in the field was delayed by~10-12 days, effectively extending the "cutout" stage defined as five or fewer nodes present above white flower, an economically important physiological adaptation to environmental conditions that marks the transition of sink strength efficiency from vegetative growth to boll development. Late flowering in all AtRAV1 and AtRAV2 transgenic cotton lines suggests a "less-stressed" phenotype recalcitrant to "drought escape" flowering response (Riboni et al. 2013), supported by marker gene and photo-assimilation studies (Mittal et al. 2014). The AtRAV1 and AtRAV2 transgenic cotton also showed extended flowering durations in the greenhouse and field (data not shown).

Figure 3:
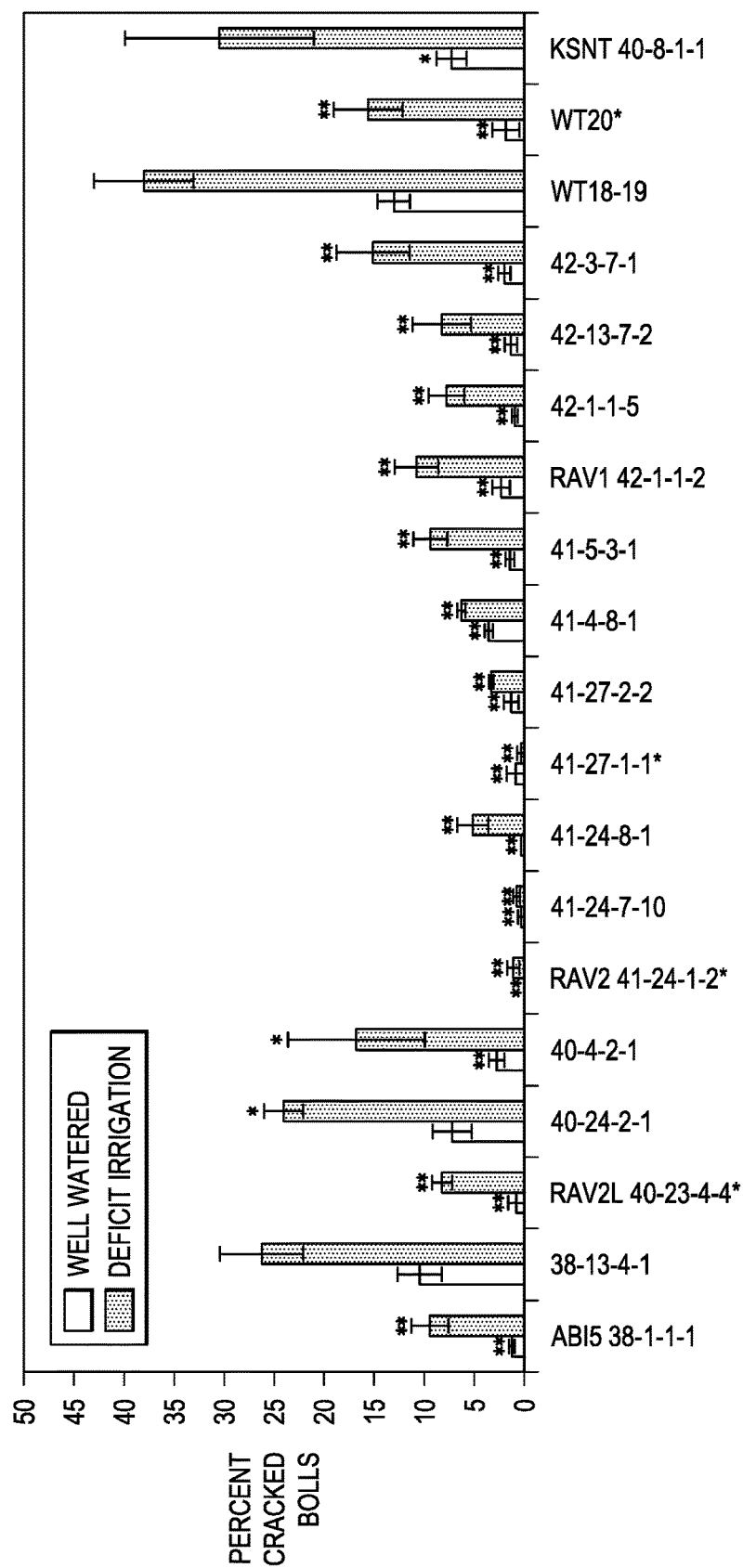
FIG. 3 shows late boll cracking in transgenic lines 99 days after sowing (DAS) under well watered (WW) and deficit irrigation (DI) treatments in the field.

AtRAV1 and AtRAV2 transgenics show delayed boll cracking. The observed delayed flowering time altered the effective maturation time manifested as delayed senescence and late boll cracking (FIG. 3). Cracked bolls were counted starting at 90 DAS until all bolls cracked open. Imposed drought stress accelerated boll maturation (cracking) in all genotypes, and there was a clear effect of lower plant density on delayed boll cracking regardless of genotype (FIG. 3, asterisked [*] lines). All the independent AtRAV1 and AtRAV2 lines showed delayed boll cracking in both well-watered and drought conditions. Interestingly, AtABI5 and AtRAV2L lines, which did not show significant differences in flowering time from wild type (FIG. 2a), nonetheless cracked their bolls later than wild type (FIG. 3).

Figure 4A:
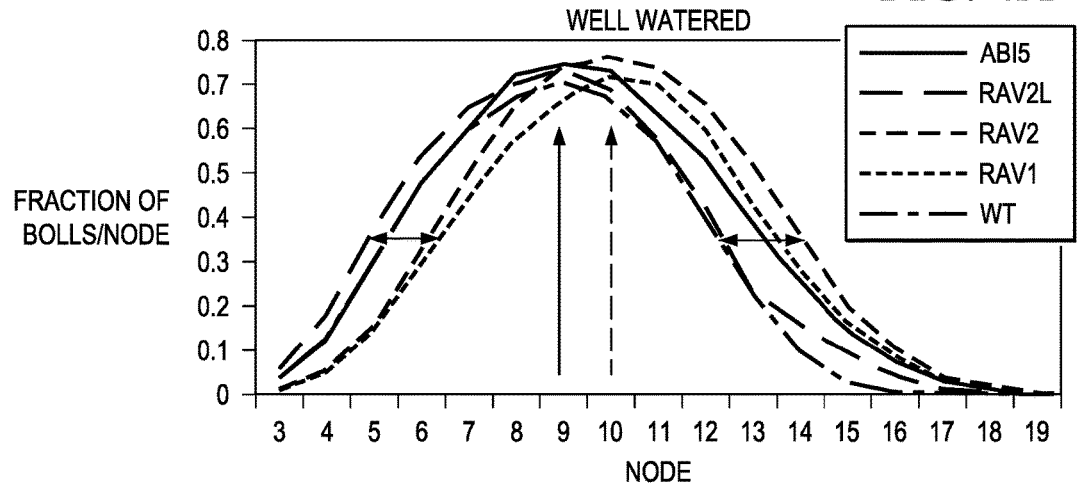
FIGS. 4a and 4b show the boll retention at individual node positions in transgenics compared to wild type under well-watered (FIG. 4a) and deficit irrigation conditions (FIG. 4b). Fraction of bolls retained under well-watered conditions was greater than for deficit irrigation treatment (black vertical arrow). AtRAV1 and AtRAV2 plants had node maxima and area under curves shifted >one node higher (red arrows) compared to wild type (WT).
Figure 4B:
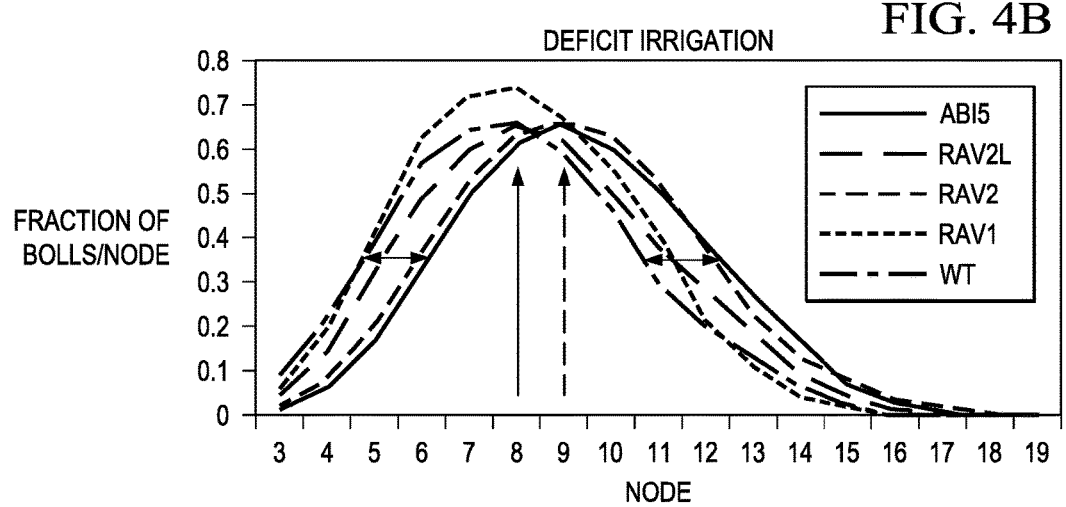

Late flowering in AtRAV1 and AtRAV2 is associated with boll retention at higher nodes. End-of-season plant boll mapping (Pettigrew 2004) was performed on the field-grown cotton plots to determine which node positions were bearing relative percentages of fruit. FIGS. 4a and 4b show the average fraction of bolls retained by each transgene-specific cotton genotype (i.e. a pool of all the individual lines for a particular transgene). AtRAV1 and AtRAV2 cotton lines showed a shift in node positions retaining bolls, with maxima at node position 10 compared to node 9 in wild type under well-watered conditions. This result suggests that a larger percentage of lint in AtRAV1 and AtRAV2 transgenics came from higher node positions. Indeed, the higher node positions of AtRAV1/2 cotton had more significant results in terms of fiber length (see below). AtABI5 and AtRAV2L genotypes showed very similar results as for wild type, underscoring the clear effect of flowering time delays in AtRAV1 and AtRAV2 overexpression lines that shift boll node maxima. Concordant with results for accelerated flowering time effects of drought stress, deficit irrigation treatment had a clear effect of lowering the position of boll retention, with control Coker312, AtRAV2L and AtABI5 cotton showing boll retention maxima at node position 8, whereas AtRAV1 and AtRAV2 lines had boll retention maxima at node position 9. Taken together, late flowering, boll retention at higher nodes, and late boll cracking under deficit irrigation supports prior results of marker gene expression, photosynthetic assimilation, and water use efficiency (Mittal et al. 2014) showing a less stressed phenotype, manifest as lack of drought escape flowering for transgenic AtRAV1 and AtRAV2 cotton.

Drought stress reduces yield much more than it reduces fiber length, demonstrating fiber is a very strong sink for assimilate during boll development. The inventors previously showed that AtABI5 and AtRAV transgenic cotton lines are resistant to imposed drought stress under field and greenhouse conditions, associated with absorption through larger root systems and greater leaf areas (Mittal et al. 2014). In order to assess the impacts of drought stress on fiber quality and in-boll "seed cotton" yield, fiber parameters of lint from hand- and stripper-harvested field plots were measured. Table 1 shows the results of three years of drought stress field trials for fiber length and yield of control Coker312. 2011 was the driest and hottest year on record in the southern high plains of the U.S., and the severe environmental conditions resulted in a 44% yield penalty for deficit irrigation treatment (10.5 acre inches of water by first flowering ~42 DAS) compared to well-watered control (which received daily irrigation until cutout ~90 DAS). The yield in 2011 well-watered plots was on a par with "dryland" (no irrigation from 25 DAS) yields in 2013, whereas 2011 deficit treatment (no water after 42 DAS) yields were lower than for the 2012 dryland treatment (Table 1). In each year there were substantial yield penalties ranging from 15% to >40% for three years of deficit treatments and 34% versus ~62% for dryland treatments in 2012 and 2013, respectively (showing relative size of plants for three watering regimes at harvest in 2012). Remarkably, the impacts of imposed droughts on fiber length were substantially less—only a few percent length penalty across all drought treatments, or on average >ten-fold less than yield penalties (Table 1). This result clearly demonstrates the very strong nature of the ovule as a sink for assimilate during fiber elongation and boll filling, even under severe drought stresses that decimated yields.

TABLE 1

Effect of drought stress on Coker312 seed cotton yields and fiber length in the field from 2011-2013.

| Year Water Treatment | Average Fiber Length, AFIS (by weight; inches) ± s.e.m. | | Seed Cotton Yield (lb./acre) ± s.e.m. | % Yield Penalty | % Fiber Length Penalty | Ratio of Yield/Length Penalties |
|---|---|---|---|---|---|---|
| | Low Nodes 6-9 | High Nodes 10-12 | | | | |
| 2011[§] (n = 9) | | | | | | |
| Full | 1.04 ± 0.012 | 0.97 ± 0.011 | 2550 ± 150 | — | — | — |
| Deficit | 0.98 ± 0.011 | 0.96 ± 0.016 | 1420 ± 160 | 44.1 | 3.5 | 12.6 |
| 2012 (n = 3) | | | | | | |
| Full | 1.04 ± 0.009 | 1.02 ± 0.006 | 4470[¶] ± 210 | — | — | — |
| Deficit | 1.03 ± 0.010 | 1.01 ± 0.003 | 3650[¶] ± 210 | 20.4 | 1.0 | 20.4 |
| Dryland | 0.95 ± 0.015 | 0.95 ± 0.009 | 1720[¶] ± 100 | 61.6 | 7.8 | 7.9 |
| 2013[†] (n = 3) | | | | | | |
| Full | | 0.99 ± 0.015 | 3780 ± 190 | — | — | — |
| Deficit | | 0.97 ± 0.006 | 3200 ± 240 | 15.5 | 2.0 | 7.7 |
| Dryland | | 0.95 ± 0.016 | 2470 ± 120 | 34.8 | 4.0 | 8.6 |
| | | | | | | Avg 11.4 |

[§]all hand harvested; yields extrapolated from 1 meter subplot samples
[¶]n = 6, machine harvested
[†]fiber measurements the average of three hand- and six machine-harvested samples AtRAV1 and AtRAV2 transgenic lines produce longer fibers under water deficit conditions in the field, resulting in better spinning properties and yarn strength. Given the seed-specific expression of the cognate B3-domain (VP1) and basic-leucine-zipper (ABI5) TFs (Brocard et al. 2002; McCarty et al. 1991) and extended boll maturation period in RAV1/2 transgenics (see above), it was possible that AtRAV and AtABI5 transgenics might have altered fiber qualities. Gin turnouts (percent fiber by weight, ranging from 36-40%) were increased in deficit irrigated (~2%) and dryland plots (~5%) and were on par with Coker312 in the transgenics (data not shown). Deficit irrigation increased total seed protein and decreased crude seed oil percentages, and seed protein was generally higher in the transgenics (data not shown). Average fiber lengths at two node ranges (6-9 and 10-12) were measured in field studies under full irrigation, deficit irrigation, or dryland field conditions and the results shown in Table 2 as relative percentage change of fiber lengths compared to Coker312. Remarkably, none of the transgenic lines had shorter fiber lengths than controls for upper nodes in 2011, or any boll positions in 2012; in these two years there were strong sustained drought and heat stresses.

TABLE 2

Three years of field trial results for fiber length of transgenic lines relative to control Coker312 as a function of node position and in response to drought stress.

| | Full Irrigation | | | | Deficit Irrigation | | | | Dryland | | | |
|---|---|---|---|---|---|---|---|---|---|---|---|---|
| | Low nodes 6-9 | | High nodes 10-12 | | Low nodes 6-9 | | High nodes 10-12 | | Low nodes 6-9 | | High nodes 10-12 | |
| Year/Genotype | Length (w), [in] | % Δ from control | Length (w), [in] | % Δ from control | Length (w), [in] | % Δ from control | Length (w), [in] | % Δ from control | Length (w), [in] | % Δ from control | Length (w), [in] | % Δ from control |
| 2011 | | | | | | | | | | | | |
| Coker312 control | 1.03 | — | 0.95 | — | 0.97 | — | 0.94 | — | | | | |
| Coker312 low density planting* | 1.07 | — | 0.99 | — | 1.00 | — | 1.01 | — | | | | |
| KSNT pseudo-control | 1.06 | 3.4 | 0.99 | 3.8 | 1.00 | 3.1 | 0.95 | 0.9 | | | | |
| ABI5$^{1-1-1}$ | 1.05 | 1.8 | 1.02 | 6.6 | 1.01 | 3.4 | 0.98 | 3.7 | | | | |
| ABI5$^{13-4-1}$ | 1.03 | −0.2 | 0.97 | 1.4 | 0.96 | −1.0 | 0.95 | 0.9 | | | | |
| RAV1$^{1-1-2}$ | 1.05 | 2.1 | 1.02 | 6.6 | 1.03 | 5.8 | 0.98 | 3.7 | | | | |
| RAV1$^{1-1-5}$ | 1.09 | 5.7 | 1.07 | 11.9 | 0.99 | 2.0 | 0.98 | 4.1 | | | | |
| RAV1$^{13-7-2}$ | 1.08 | 5.4 | 1.02 | 6.6 | 1.04 | 7.2 | 1.04 | 10.4 | | | | |
| RAV1$^{3-7-1}$ | 1.06 | 2.8 | 1.04 | 8.7 | 1.04 | 6.8 | 1.01 | 6.9 | | | | |
| RAV2$^{24-1-2}$* | 1.03 | −3.7 | 1.04 | 5.0 | 1.01 | 0.7 | 1.01 | 0.3 | | | | |
| RAV2$^{24-7-10}$ | 1.06 | 3.1 | 1.05 | 9.8 | 1.01 | 3.4 | 1.01 | 7.3 | | | | |
| RAV2$^{24-8-1}$ | 1.10 | 7.0 | 1.05 | 9.8 | 1.04 | 6.8 | 1.07 | 13.6 | | | | |
| RAV2$^{27-1-1}$* | 1.05 | −2.2 | 1.01 | 2.0 | 1.04 | 3.7 | 1.01 | 0.3 | | | | |
| RAV2$^{27-2-2}$ | 1.07 | 4.0 | 1.01 | 6.3 | 0.99 | 2.0 | 1.02 | 8.3 | | | | |
| RAV2$^{4-8-1}$ | 1.07 | 4.0 | 1.05 | 10.1 | 1.03 | 6.2 | 1.01 | 7.3 | | | | |
| RAV2$^{5-3-1}$ | 1.04 | 0.8 | 0.99 | 3.5 | 0.97 | −0.7 | 0.96 | 2.3 | | | | |
| RAV2L$^{23-4-4}$* | 1.06 | −0.9 | 1.07 | 8.4 | 1.01 | 0.7 | 1.02 | 1.3 | | | | |
| RAV2L$^{24-2-1}$ | 1.02 | −1.1 | 1.00 | 5.2 | 0.99 | 1.7 | 0.99 | 4.8 | | | | |
| RAV2L$^{4-2-1}$ | 1.06 | 3.4 | 1.05 | 10.1 | 1.00 | 3.1 | 0.95 | 0.5 | | | | |
| RAV1, RAV2 avg | | 2.21 | | 7.43 | | 3.53 | | 5.08 | | | | |
| 2012¶ | | | | | | | | | | | | |
| Coker312 control | 1.04 | — | 1.02 | — | 1.03 | — | 1.01 | — | 0.95 | — | 0.95 | — |
| KSNT control | 1.06 | 1.9 | 1.04 | 1.6 | 1.01 | −1.9 | 1.01 | −0.7 | 0.96 | 1.4 | 1.00 | 5.3 |
| Coker312 control. 1§ | 0.98 | — | N.D. | — | 0.98 | — | N.D. | — | 0.92 | — | N.D. | — |
| ABI5$^{13-4-1}$§ | 0.96 | −2.2 | N.D. | — | 0.96^ | −2.0 | N.D. | — | 0.92 | 0.4 | N.D. | — |
| ABI5$^{1-1-1}$§ | 0.94 | −3.9 | N.D. | — | 0.98 | 0.2 | N.D. | — | 0.94^ | 1.6 | N.D. | — |
| Arkot(UA 48 ctrl)§ | 0.95 | — | N.D. | — | 0.94 | — | N.D. | — | 0.90 | — | N.D. | — |
| UA48§ | 1.07 | 12.2 | N.D. | — | 1.05 | 11.7 | N.D. | — | 1.04 | 15.6 | N.D. | — |
| RAV1$^{13-7-2}$ | 1.09 | 4.8 | 1.05 | 2.6 | 1.06 | 3.2 | 1.04 | 3.0 | 0.99 | 3.9 | 1.00 | 6.0 |
| RAV1$^{3-7-1}$ | 1.10 | 6.1 | 1.08 | 5.9 | 1.04 | 1.3 | 1.05 | 3.3 | 0.97 | 2.5 | 0.99 | 4.9 |
| RAV2$^{24-7-10}$ | 1.08 | 4.2 | 1.07 | 4.9 | 1.07 | 3.9 | 1.06 | 4.1 | 1.00 | 5.3 | 1.01 | 6.7 |
| RAV2$^{24-8-1}$ | 1.13 | 9.0 | 1.09 | 6.5 | 1.07 | 4.2 | 1.08 | 6.3 | 1.02 | 7.0 | 1.03 | 8.5 |
| RAV2$^{4-8-1}$ | 1.12 | 7.7 | 1.06 | 3.6 | 1.08 | 4.9 | 1.06 | 4.3 | 0.99 | 4.2 | 1.00 | 6.0 |
| RAV1, RAV2 avg | | 7.33 | | 3.92 | | 4.87 | | 3.50 | | 3.82 | | 5.35 |

TABLE 2-continued

Three years of field trial results for fiber length of transgenic lines relative to control Coker312 as a function of node position and in response to drought stress.

| 2013[†] | Length (w), [in] | % Δ from control | Length (w), [in] | % Δ from control | Length (w), [in] | % Δ from control |
|---|---|---|---|---|---|---|
| Coker312 control[¶] | 1.03 | — | 0.973 | — | 1.01 | — |
| ABI5[13-4-1¶] | 1.01 | −1.3 | 1.00 | 2.7 | 1.01 | 0.7 |
| RAV1[13-7-2¶] | 1.02 | −1.0 | 0.97 | −0.3 | 1.03 | 2.6 |
| RAV2[24-8-1¶] | 1.03 | 0.6 | 1.02 | 4.4 | 1.07 | 6.0 |
| ABI5[13-4-1] × RAV1[13-7-2¶] | 1.05 | 1.9 | 1.02 | 4.4 | 1.03 | 2.3 |
| ABI5[13-4-1] × RAV2[24-8-1¶] | 1.05 | 1.9 | 1.07 | 10.3 | <u>1.08</u> | 7.6 |
| RAV1[13-7-2] × RAV2[24-8-1¶] | 1.00 | −2.3 | 1.00 | 2.7 | 1.08 | 7.0 |
| Coker312 control2[§] | 1.00 | — | 0.96 | — | 0.93 | — |
| KSNT control[§] | 0.96 | −3.3 | 0.96 | −0.7 | 0.93 | 0 |
| ABI5[13-4-1,2§] | 0.96 | −4.0 | 0.97 | 0.7 | 0.97 | 3.6 |
| RAV1[13-7-2§] | 0.95 | −4.3 | 0.96 | −0.3 | 0.97 | 3.9 |
| RAV2[24-8-1§] | 0.98 | −1.3 | 0.97 | 0.7 | <u>1.00</u> | 7.5 |
| RAV2[4-8-1§] | 0.97 | −2.3 | 0.96 | −0.7 | 0.97 | 3.6 |
| Dryland RAV avg | | | | | | 5.06 |
| Total RAV avg, 3 yrs | | | | | | 4.73 |

For statistical significance analysis, a two-tailed Student's t-test was applied with unequal variance assumed. Fiber lengths in bold and underlined are highly significant (P < 0.006); bold numbers are significant (P < 0.05), and underlined numbers are marginally significant (P < 0.10). Results are the average of three biological replicates.
*indicates hand planted lines at low density of two plants per foot row
N.D. not determined.
[†]all bolls harvested together per plant; samples blended from one to several plants
[¶]indicates hand harvested samples (n = 3)
[§]indicates machine harvested samples (n = 6 for Coker312.1; n = 3 for all others except ^: n = 2)

In well-watered (Full Irrigation) plots in 2011 and 2012, ~4-7% significantly longer (P<0.05) fibers were observed in two AtRAV1 lines (13-7-2; 1-1-5) and two AtRAV2 lines (4-8-1 and 24-8-1) at node positions 6-9 corresponding to the early period of boll set and maturation (Table 2). Drought effects would have been mitigated in these bolls because the deficit treatment (water withheld after 42 DAS) was initiated at first flowering. Furthermore, these lines showed ~4-13% longer fibers compared to wild type under deficit and dryland irrigation conditions in 2012 and 2013. Most compelling was the finding that fiber lengths of bolls at node positions 10-12, which corresponds to the mid-phase of growth and strong drought effects in 2011 and 2012 field studies, were significantly increased ~6% to 13% under both well-watered and drought conditions for those lines observed to have positive effects at lower nodes, and for another two independent AtRAV2 lines (24-7-10 and 27-2-2). Statistical analysis of all three years' average fiber lengths measured across all treatments (well-watered and deficit in 2011; well-watered, deficit, and dryland in 2012, 2013; hand- and machine-harvested) showed the fibers of AtRAV1[13-7-2], AtRAV2[4-8-1], and AtRAV2[24-8-1] events were significantly longer than controls (P=0.001, <0.00001, <0.0001, respectively; one-sided paired Student's t test, equal variance assumed). Taken together, these data conclusively establish that AtRAV1 and AtRAV2 overexpression resulted in reproducible and in some cases double digit percent increases in upper boll fiber lengths under the hottest and driest field conditions on record (2011), and single digit percentage increases in relatively less-stressed (2013) field conditions (Table 2). Significantly longer fiber lengths for a select AtRAV2 line (24-8-1) were on a par with the 'gold standard' of fiber length quality reported for an elite cultivar 'UA48' (Bourland & Jones 2012) relative to its parental breeding stock 'Arkot8712' (Table 2; FIG. 5).

The traditional description of a high quality fiber 'package' in the textile industry is "long, strong, and fine," when the use is to spin yarns for high-value products. Therefore, ~500 g of select AtRAV1 and AtRAV2 fibers from the 2011 harvest were subjected to a novel protocol for ring spinning (Gregory et al. 2012). The protocol mimics fine-count (Ne30 or "English" count=19.685 Tex [g/km]) textile production at the industrial scale, using state-of-the-art equipment for the processes of blending, cleaning, carding, drawing, roving, and ring spinning. FIG. 5 shows that fibers of select AtRAV1 and AtRAV2 lines made significantly stronger, more elastic (data not shown), more uniform yarn with fewer imperfections than yarn spun from control, well-watered Coker312 samples. Significantly, the drought-stressed fiber from Coker312 control failed to spin yarn in the protocol because of low quality, whereas the yarns from the transgenic fiber samples subjected to drought stress were significantly better than non-stressed Coker312 control (FIG. 5).

Figure 7C:
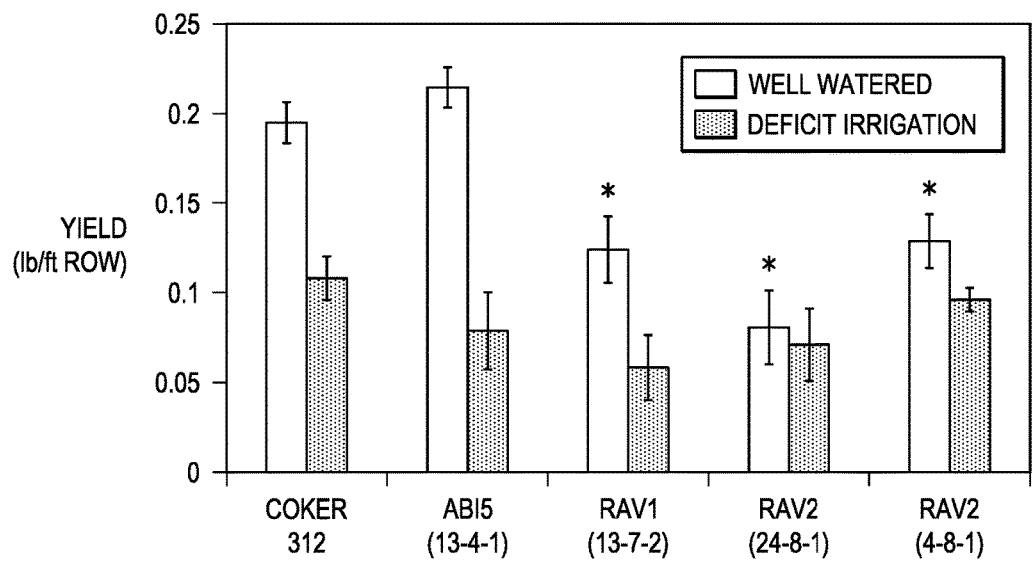

Field-grown transgenic AtRAV1 and AtRAV2 cotton yields. It has long been known by cotton breeders and producers that there exists a negative correlation between high fiber strength and length versus high lint production (Culp & Harrell 1975). For AtRAV1 and AtRAV2 over-expressing lines that consistently produced longer fiber in the greenhouse and field, the inventors compiled three years of yield data from machine-harvested paired row subplots in 2013 and 2012 and from hand-harvested one meter subplots in 2011. FIG. 7a shows that in the largest study samples (2013) there were no significant differences in yields for those AtRAV1 and AtRAV2 lines chosen for study, although seed cotton (in-boll) yields were slightly lower than controls in well-watered and drought treatments. Similar results were obtained in the prior two years' field trials (FIGS. 7b, 7c), when some AtRAV1 and AtRAV2 yields were significantly lower than control lines, but still on par with the gold standard elite cultivar UA48 that produced relatively long staple under all irrigation treatments (Table 2).

Figure 9:
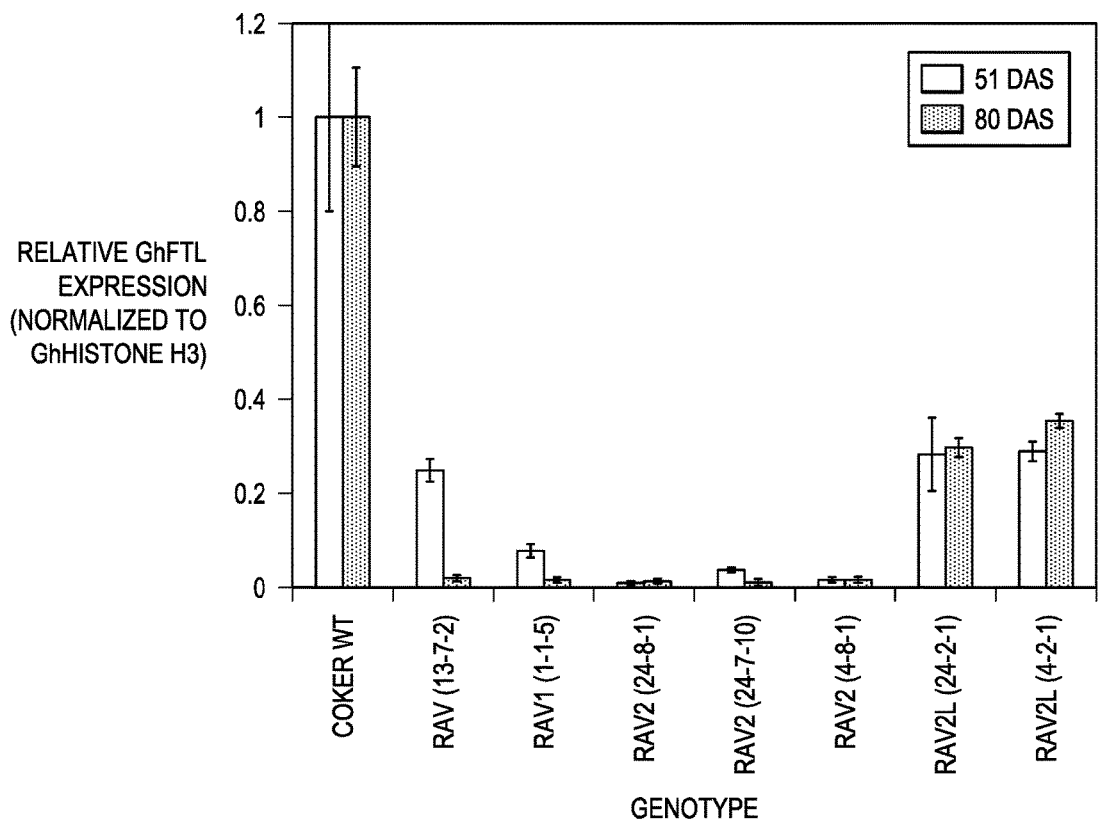
FIG. 9 shows quantitative Real Time PCR (q-RT-PCR) assay results for GhFTL expression in leaves of greenhouse-grown independent transgenic lines at onset of flowering (51 DAS for Coker WT) and full bloom (80 DAS). Error bars are SEM (n=3 technical replicates).
Figure 8A:
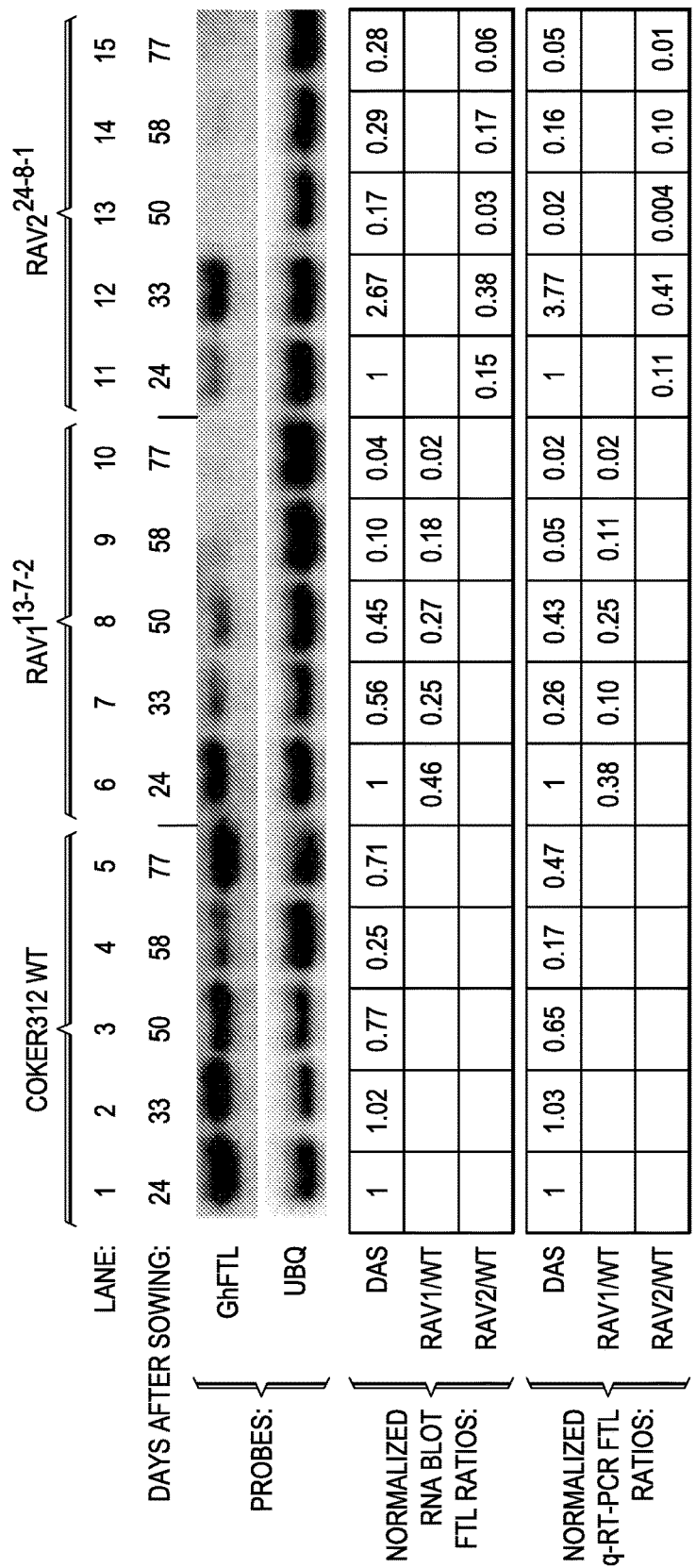
FIGS. 8a and 8b show RNA blot assays of various cotton genotypes subjected to different conditions.

Characterization of transgenic cotton lines for markers of flowering time and ovule development. An FT-Like homolog has been reported for cotton (NCBI GenBank locus: HM631972, GhFTL)(Laurie et al. 2011) and a related pair of cotton expressed sequence tags (ES826802/DW506935) are highly homologous (~74-78% identical) to AtFT and TWIN SISTER OF FT (TSF; AT4G20370) (Ando et al. 2013), which act redundantly in *Arabidopsis* to promote flowering (Yamaguchi et al. 2005). In order to test the hypothesized mechanism of late flowering in transgenic cotton lines, the expression of GhFTL was probed by RNA blot at various time points starting from 24 DAS under well-watered conditions until 77 DAS. The 24 DAS time point marked squaring initiation in Coker312, whereas squaring initiation in AtRAV1 and AtRAV2 transgenic lines was at ~33 DAS (data not shown). The 50 DAS time point marked flowering in control plants whereas 58 DAS marked the beginning of flowering in AtRAV1 and AtRAV2 lines. FIG. 8a shows results of an RNA blot result demonstrating that GhFTL transcript was highly expressed in Coker312 at 24 DAS and 33 DAS (lanes 1, 2) and declined to ~80% of maximum fold at flowering (50 DAS; lane 3). GhFTL expression further reduced to ~25% at 58 DAS (lane 4) and later increased to ~70% of maximum at full bloom (77 lower at all the stages studied compared to wild type (lanes 6-15), consistent with the mechanism of RAV2 repression of FT described for *Arabidopsis* (Castillejo & Pelaz 2008). The quantification of the RNA blots was confirmed by qRT-PCR of an independent repeat study, where normalized GhFTL ratios gave a correlation coefficient of 0.97 between normalized RNA blot band intensities and qRT-PCRs across genotypes and the time series (FIG. 8a). FIG. 9 shows similar down regulation of GhFTL for independent transformant AtRAV1$^{1\text{-}1\text{-}5}$ and two other independent AtRAV2 lines, but not for two reference AtRAV2L transformant lines, confirming the functional effects of AtRAV1 and AtRAV2 overexpression and the observed lack of late-flowering (FIGS. 2a, 2b) or boll retention phenotypes (FIGS. 4a, 4b) for AtRAV2L lines and segregating non-transgenic sibs.

Figure 8B:
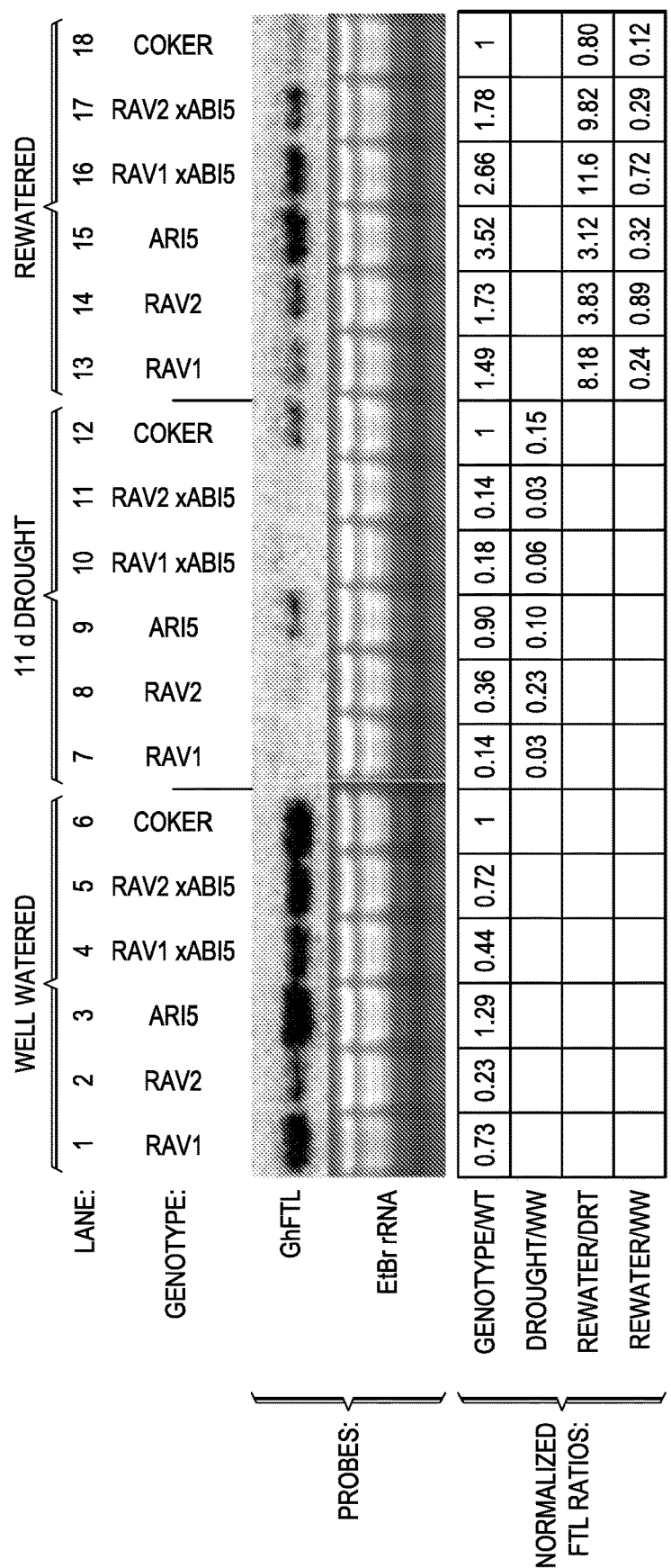

GhFTL transcript is repressed by drought stress and is up-regulated during drought recovery in AtRAV1, AtRAV2, and stacked AtRAV×AtABI5 transgenics. AtRAV1 and AtRAV2 over-expression reduced GhFTL expression during the flowering transition (FIG. 8a). RAV×ABI5 stacked transgenic lines have previously been shown to act in synergy (especially RAV1×ABI5) for phenotypic characters in terms of improved 'stress free' phenotypes (average longer internodes, bigger lateral root systems, delayed flowering) and better yield characters (more fruits, lower reduction in photosynthesis in response to drought)(Mittal et al. 2014). Consistent with prior results, under well-watered conditions GhFTL expression was ~25-70% of wild type levels in AtRAV1 and AtRAV2 and RAV×ABI5 stacked lines (FIG. 8b; lanes 1-5 compared to lane 6), whereas in the AtABI5 line GhFTL was elevated ~50%. In response to imposed drought stress GhFTL expression was reduced to ~20% of unstressed level in wild type and further reduced in AtRAV1 and AtRAV2 and RAV×ABI5 stacked transgenic lines (FIG. 8b, lanes 7-11 compared to lane 12). All the transgenics had 3- to ~11-fold increases in GhFTL transcript abundance after overnight recovery from drought stress, but not wild type (FIG. 8b, lanes 13-17 compared to lane 18) such that after drought recovery the transgenics had 1.5 to 3.7-fold higher levels GhFTL than did wild type. Drought stress results in ~10 fold up regulation of endogenous GhRAV2L (Mittal et al. 2014), which drops to below initial levels after rewatering, suggesting a molecular mechanism for the increased control of gas exchange in response to drought as well as increased expression of ABA marker genes for antioxidant and osmolyte biosynthesis (Mittal et al. 2014). The observed rapid down- and up regulation of GhFTL during drought stress and recovery, respectively, the magnitude of which is strictly correlated with AtRAV1 and AtRAV2 over-expression (FIG. 8b), is likely the consequence of repression of GhFTL by AtRAVs.

Figure 10A:
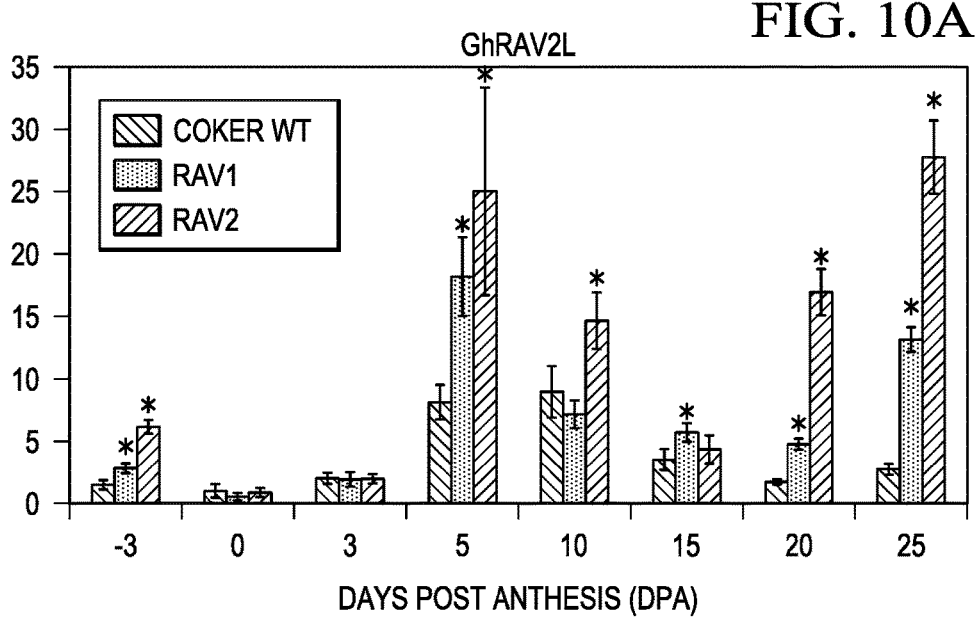
FIGS. 10a to 10e show quantitative Real Time PCR (q-RT-PCR) assay results for endogenous GhRAV2L (FIG. 10a), select GhMYB genes (FIG. 10b=MYB2.
Figure 10B:
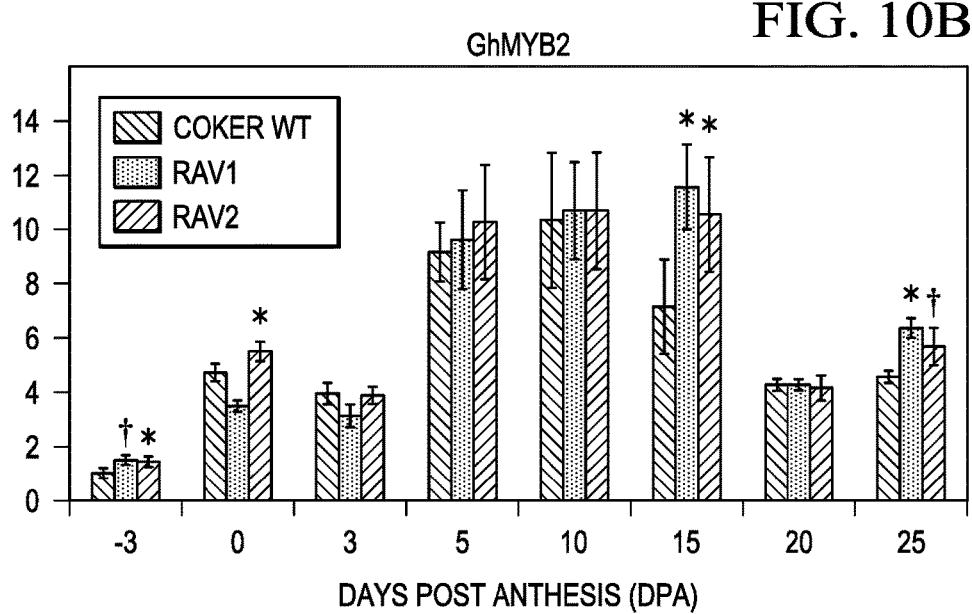
Figure 10C:
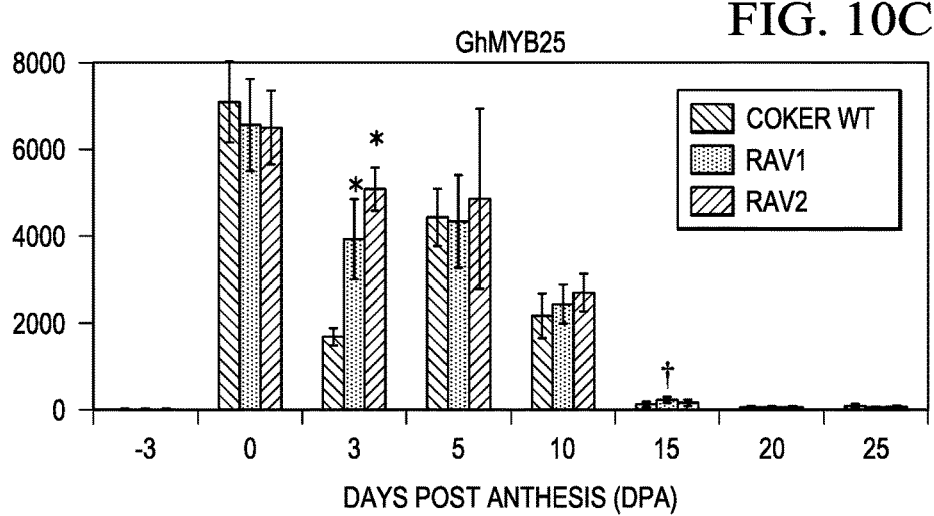
Figure 10D:
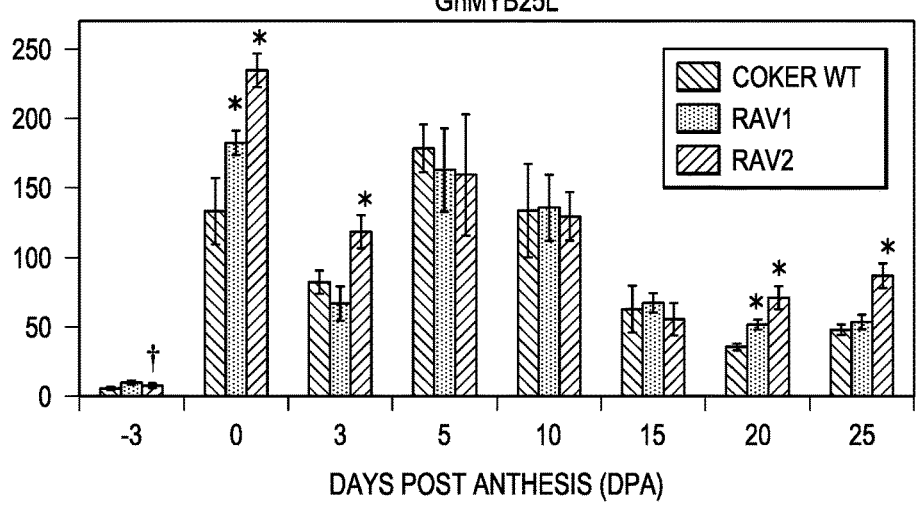
Figure 10E:
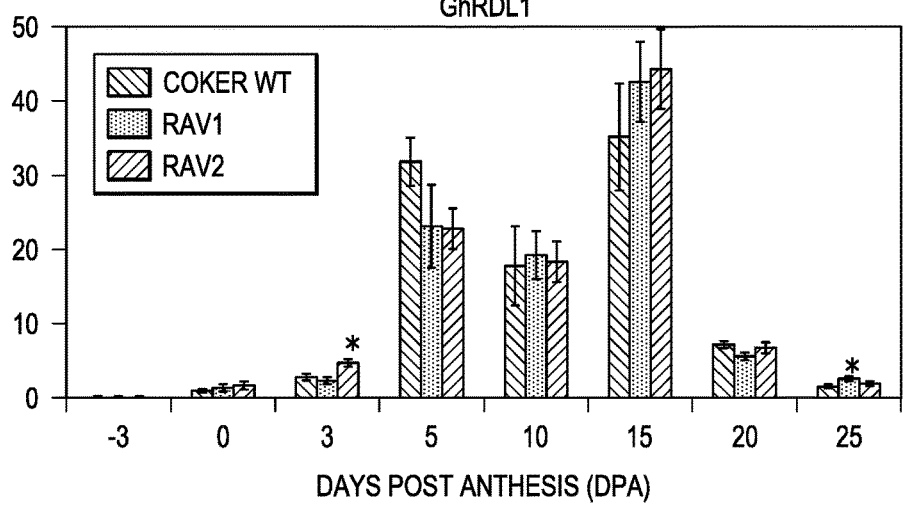

Characterization of GhRAV2L, and fiber initiation and elongation effectors GhMYB25-Like, GhMYB2, and GhMYB25 have elevated expression in developing ovules of AtRAV1 and AtRAV2 transgenics. Several RAV2-Like homolog expressed sequence tags (JQ837701, GhRAV2L/ZM3RAV) have been described for cotton (Wang et al. 2012a). In the *G. raimondii* reference D genome for cotton (Wang et al. 2012b) there are three RAV homologues, as in *Arabidopsis* (Gorai.008G185900/RAV2-Like, Gorai.005G-138100/RAV1-Like, and Gorai.013G080000/TEM1/RAV2L-Like), suggesting orthologous functions for these genes in allotetraploid *G. hirsutum* and diploid A genome *G. arboreum* (Li et al. 2014). The inventorspreviously showed endogenous GhRAV2L mRNA is elevated in AtRAV1- and AtRAV2 over-expressing lines during drought stress recovery, suggesting a functional interaction between the ectopically expressed AtRAVs and the endogenous GhRAV2L associated with ABA responses and reduced stress marker gene expression (Mittal et al. 2014). The inventors assayed by qRT-PCR for GhRAV2L expression in developing ovules as well as for three MYB effectors (GhMYB25L, GhMYB2, and GhMYB25) of fiber initiation (Walford et al. 2011) and/or elongation (Cedroni et al. 2003; Machado et al. 2009; Wu et al. 2006). Epidermal cells of ovules that initiate fibers within three days post-anthesis (0-3 DPA) become lint fibers, whereas fiber elongation proceeds until 25 DPA with secondary cellulose deposition from 15 to 50 DPA and fiber cell dehydration and maturation after 45 DPA (Basra & Saha 1999). FIG. 10a shows qRT-PCR evidence using gene-specific primers (Table 3; data not shown) that GhRAV2L is expressed three days before anthesis and at higher levels from five to 15 DPA, the time when fiber elongation is maximal. Similar to results for leaves during drought recovery (Mittal et al. 2014), endogenous GhRAV2L expression was elevated two- to threefold in AtRAV1 and AtRAV2 over-expression lines three days before anthesis and during fiber elongation (5 DPA) and secondary wall biosynthesis (FIG. 10a, 20-25 DPA).

TABLE 3

List of primers used in this study. "F" is forward and "R" reverse

| Primer name | 5'-Sequence-3' | SEQ ID |
|---|---|---|
| N-Hist_3_F | GAAGCCTCATCGATACCGTC | 1 |
| N-Hist_3_R2 | GCAAAGGTTGGTGTCTTCAAA | 2 |
| AtRAV1-F | CGAGGTCGATTTCTTGAATTCTCA | 3 |
| AtRAV1-R | TCCGTTACCATTACGACGCC | 4 |
| AtRAV2-F | ATCTTTCTCCGCCACCACCG | 5 |
| AtRAV2-R | TCTCGGGATCCAACACGACG | 6 |
| AtRAV2L-F | TCCAAAGCCGACAACGACGA | 7 |
| AtRAV2L-R | ACTCGGTCTCGACGCCGTTC | 8 |
| AtABI5-F | CCAAACCCGAACCAAAACCA | 9 |
| AtABI5-R | CTTGACCCGGGAATGAAGGA | 10 |
| Gh_HM631972_FTL_qRT_203_F | TGGTGGATCCTGATGCTCCAAG | 11 |
| Gh_HM631972_FTL_qRT_337_R | TTGGTCGTGGGCTCTCATAGCA | 12 |
| Gh_HM631972_FTL_qRT_316_F | TGCTATGAGAGCCCACGACCAA | 13 |
| Gh_HM631972_FTL_qRT_459_R | CCCGAGGTTGTAAAGCTCAGCA | 14 |
| Gh_HM631972_FTL_Nrth_101_F | GGGATGTTAGCAATGGTGTTGAGC | 15 |
| Gh_HM631972_FTL_Nrth_467_R1 | ACCGGCAACCCGAGGTTGTAAA | 16 |
| Gh_HM631972_FTL_Nrth_504_R2 | TCCACTCTCCCTCTGGCAGTTAAA | 17 |
| Gh_DQ116441_UBQ7_Nrth_48_F | GGTCGAGTCTTCGGACACCATT | 18 |
| Gh_DQ116441_UBQ7_Nrth_439_R | TGAGCCCACACTTACCGCAATA | 19 |
| Gh_AY115507_Myb2_qRT_119_F | CGGCAAGAGTTGCAGGTTGAGA | 20 |
| Gh_AY115507_Myb2_qRT_254_R | CCCAGCAATCAAAGACCACCTG | 21 |
| Gh_AF336283_Myb25_qRT_529_F | AGCAACCACTTCACTGCCGTTG | 22 |
| Gh_AF336283_Myb25_qRT_631_R | TGAATAACCCGCAGACGACACC | 23 |
| Gr_HM134083-MYB25like_qRT_791_F | TGGAGAAATCGAGCCAAGTTGC | 24 |
| Gr_HM134083-MYB25like_qRT_907_R | CCGCCCTGTATGAGCCTTGAAA | 25 |
| Gh_AY072821_RDL_qRT_542_F | GCCAGCGATTGAAGGAGAGGAA | 26 |
| Gh_AY072821_RDL_qRT_670_R | TGCATTGGGGTTTGTTTTTCCA | 27 |
| Gh_ZM3RAV_JQ837701_qRT_411_F | GCCTAAGGTGCCAAAACCATCC | 28 |
| Gh_ZM3RAV_JQ837701_qRT_549_R | GCATTCCAAGGCTGAAATCGTG | 29 |

The D genome allele of GhMYB2 is targeted preferentially by microRNA828 (miR828; orthologue to *Arabidopsis* AT4G27765) (Guan et al. 2014) and transactivates the ABA-inducible promoter of GhRDL1 (Wang et al. 2004), whereas GhMYB25 physically interacts with homeodomain leucine-zipper GhHD-1 orthologue Meristem Layer1 in *G. barbadense* (Zhang et al. 2010b). The inventors assayed, by qRT-PCR, the expression of these select MYBs and RDL1 in developing ovules and found that in AtRAV1- and AtRAV2 overexpressing lines these MYB effectors, but not RDL1, were at various time points up-regulated relative to control during and/or after their respective normal developmental windows (FIG. 10b-10e)(Guan et al. 2014; Machado et al. 2009; Walford et al. 2011), analogous to the result for endogenous GhRAV2L expression in the transgenics at −3, 5, and 20-25 DPA (FIG. 10a). Specifically, GhMYB25L and GhMYB25 were significantly elevated at zero and three DPA, respectively (FIG. 10d, 10c), which are the developmental windows when these genes are maximally expressed, after which time they decrease (Machado et al. 2009; Walford et al. 2011). Because GhRAV2L expression was elevated in the transgenics at −3 DPA, 5 DPA, and after (FIG. 10a), which precedes observed wild type Coker312 and AtRAV1 and AtRAV2 transgenic line expression of GhMYB25 and GhMYB25L, taken together these results suggest that GhRAV2L, and by inference AtRAV1 and AtRAV2, may function in a hierarchy with these MYBs. The observed longer fibers in AtRAV1 and AtRAV2 over-expressing lines may be the consequence of elevated and/or prolonged GhMYB25L, GhMYB25, and GhMYB2 expression during ovule development and fiber elongation/maturation stages.

Figure 6B:
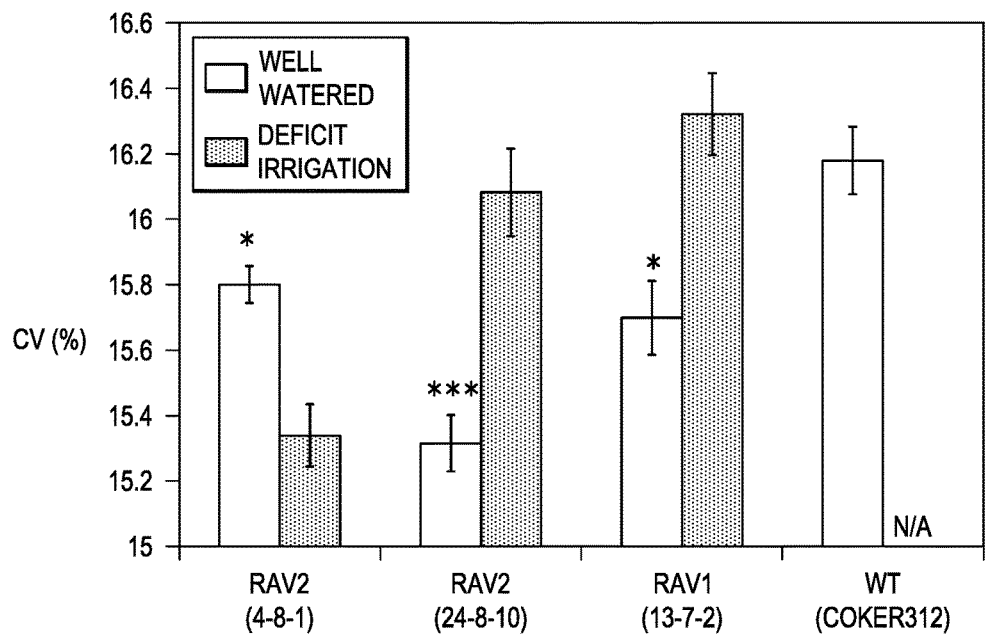
Figure 6C:
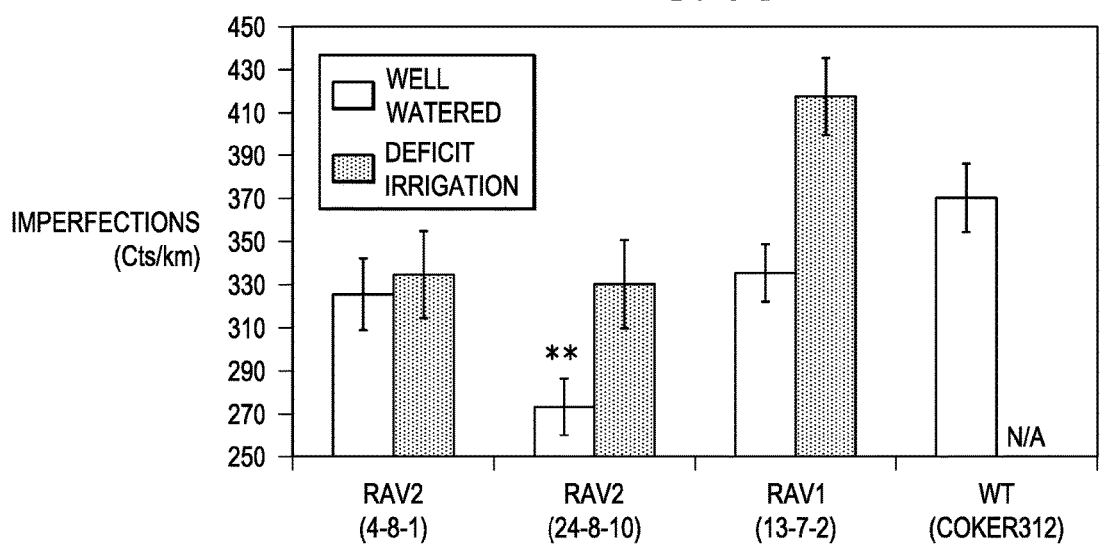

The transgenic cotton lines expressing AtRAV1, AtRAV2, AtRAV2L and AtABI5 further characterized in this study were previously shown to exhibit multiple drought resistance and improved biomass traits (Mittal et al. 2014). Long staple is the most coveted agronomic trait for cotton and the focus of most breeding programs, yet these results (Table 1) show cotton is naturally adapted to maximize fiber length under environmental stress at a high cost of low yields. AtRAV1 and AtRAV2 transgenic cotton lines and the stacked RAV×ABI5 lines are delayed in flowering time (FIG. 2a, 2b) which is associated with GhFTL repression (FIG. 8a), yet these lines have extended flowering durations (data not shown). Delays in boll cracking (FIG. 3) and leaf senescence (data not shown) have the effect of extending the boll-filling period, which impacted fiber and seed quality positively. Extended flowering duration and boll filling can be an important trait for cotton growing under dryland conditions, whereby plants can exploit late season precipitation for production and maturation of additional bolls. In regions like the arid U.S. southwest, where irrigation is essential and growing seasons are long, there is opportunity for a second fruiting cycle, a 'top crop' (Unruh & Silvertooth 1997). Extended flowering duration and boll filling in AtRAV1 and AtRAV2 transgenic lines affords a practical advantage for such climatic regions of cotton production. Despite the short growing season and extreme drought conditions in west Texas that routinely results in penalties for yield and fiber quality, even when substantial irrigation is applied (Table 1), the AtRAV1 and AtRAV2 lines generate fruit at higher node positions (FIG. 3) analogous to a 'top crop' and produce longer staple, especially at these higher nodes subjected to greater environmental stresses (Table 2). AtRAV1 and AtRAV2 lines produced longer fiber under well-watered and deficit irrigation conditions over three years of field trials (Table 2) that translated to improved yarn properties (FIG. 6a-6c).

Three recent reports showed transgenic cotton lines with greater assimilate sink strength had increased seed set, leaf areas, and fiber lengths in the greenhouse by ~12% at 20 DPA (Xu et al. 2012), and by ~5-7% at maturity with mild improvement in strength (Abdurakhmonov et al. 2014; Jiang et al. 2012). The average ~5% fiber length increases the inventors observed over three years for independently validated AtRAV1 and AtRAV2 lines especially under drought stress in the field is on par with increases reported for *Sucrose Synthase* over-expressors in the greenhouse. AtRAV1 and AtRAV2 effects on repression of GhFTL (FIG. 8a, 8b) was associated with an apparent increased vegetative growth phase correlated with elongation of fibers, possibly due to greater photoassimilate being transported into the developing ovules when imposed drought stresses resulted in huge yield penalties but only modest fiber length penalties (Table 1), a compelling argument for elongating fibers as the strongest assimilate sink in cotton.

Based on the FT links to stomatal opening (Ando et al. 2013; Kinoshita et al. 2011) and ABA and stress adaptation processes revealed by the results shown herein for AtRAV1 and AtRAV2 cotton (Mittal et al. 2014), the inventors offer a possible mechanism, which is not a limitation of the present invention, that repression of GhFTL may explain the increased plant size, fiber length, and yield observed for transgenic cotton over-expressing a truncated motif of FLOWERING CONTROL A (FCA, part of the autonomous flowering pathway wherein loss of function fca mutants have delayed flowering)(Sun et al. 2012).

Xu et al. (2012) speculated that the mechanisms of increased biomass in sucrose synthase overexpressing cotton plants could be either by altered hexose signaling, especially in leaves where osmolality is not a significant factor for leaf expansion, or by osmotic effects in single-celled fiber trichomes. The inventors have demonstrated previously (Mittal et al. 2014) increased leaf area, internode lengths, and dry biomass, especially root biomass (another strong sink for assimilate), without significant yield penalties in the field for AtRAV1- and AtRAV2 overexpressing cotton lines further characterized here. These results are consistent with the notion that altered signaling pathways including hexose signaling mediated directly or indirectly by AtRAV1 and AtRAV2 could enhance vegetative and fruit phenotypes in these transgenic cotton lines. Evidence consistent with this is that RAV proteins can bind to the promoter and drive expression of elongation Initiation Factor (eIF5A). Yeast and transgenic poplar that express eIF5A display elevated protein content, and an improved tolerance to abiotic stresses (Wang et al. 2012c). Other findings consistent with this view is that separate isoforms of eIF5A facilitate the translation of mRNAs encoding proteins involved in senescence, a process regulated by RAVs, sugar-, and abiotic signaling pathways (Belda-Palazón et al. 2014; Parkash et al. 2014; Wingler & Roitsch 2008; Woo et al. 2010; Zhao et al. 2008).

Figure 12:
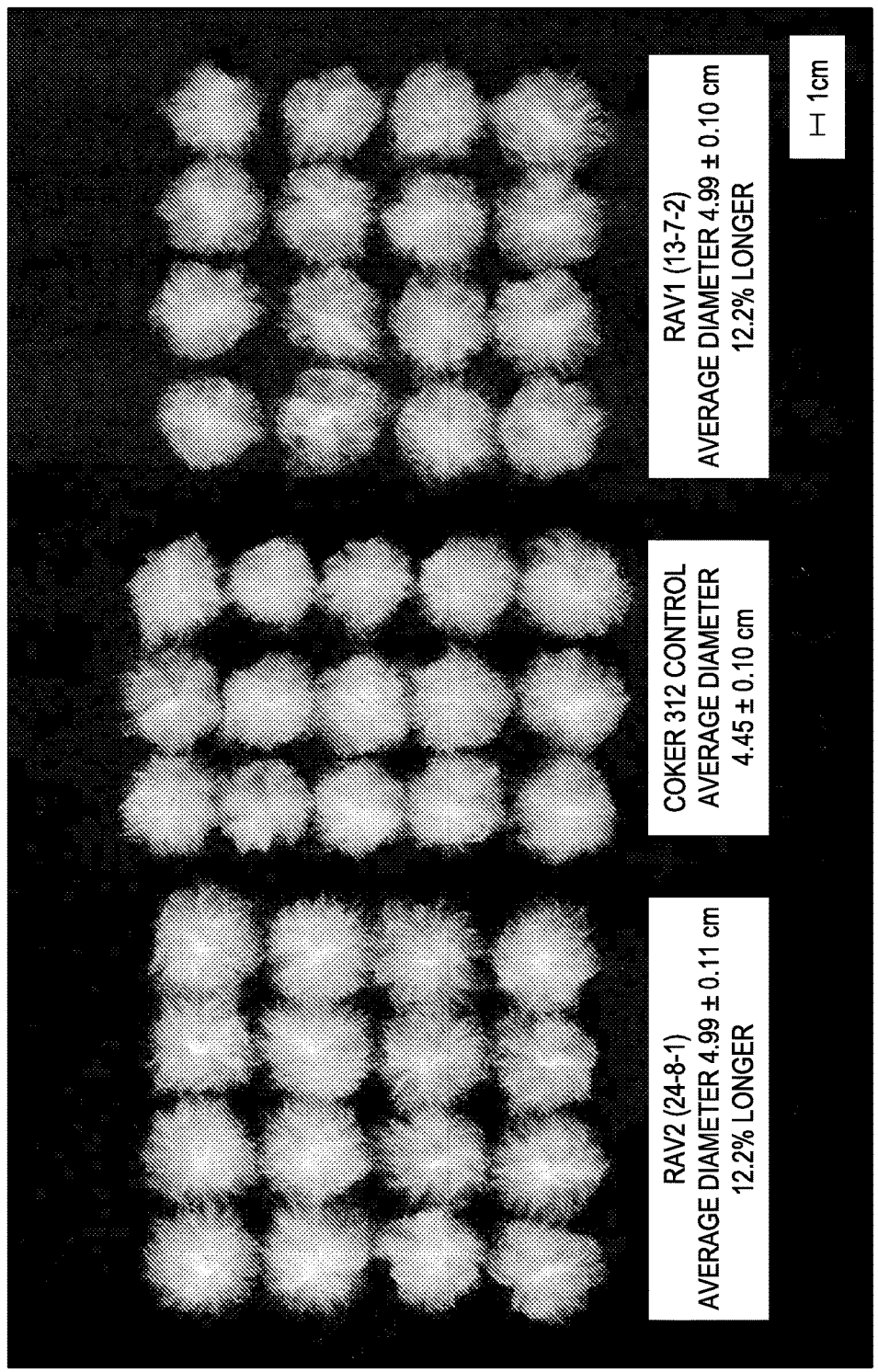
FIG. 12 shows four representative individual seeds with drawn out fibers from different bolls harvested from four greenhouse-grown AtRAV2 and AtRAV1 cotton plants compared to five seeds from three Coker312 control plants. Transgenic seeds with fibers drawn out had significantly different diameters than Coker312 control (p<10-9; two-sided Student's t-test, unequal variance assumed. n=16-30).

Fiber lengths for AtRAV overexpressor lines compare favorably with a leading conventional cultivar 'UA48' (FIG. 5) and the observed increases come without appreciable reductions in yield (FIG. 7a-7c). FIG. 11 shows AFIS histograms of fiber lengths from 2012 field trial samples which clearly demonstrate dryland conditions reduced average fiber lengths by ~$3/32^{nds}$ of an inch, and that the AtRAV2 line had longer fibers (by ~$1/8^{th}$-inch on average) than control Coker312, such that the dryland-grown transgenic line had longer fibers than well-watered Coker312. FIG. 12 shows representative individual seeds with drawn out fibers from different bolls harvested from greenhouse-grown AtRAV2 and AtRAV1 plants compared to Coker312 control. The quality of fiber from AtRAV transgenics translated to a real-world textile application where poor quality fiber (drought-stressed Coker312; FIG. 6a-6c) completely failed to perform. Introgression of select AtRAV1 and AtRAV2 transgenic events into elite germplasms could substantially improve fiber quality and hence farm gate value. Two real-world measures of the issues impacted by these findings are that: (i) despite the ~50% longer fibers produced by 'sea island'/Pima cotton cultivars (*G. barbadense*) compared to 'upland' *G. hirsutum* lint, Pima accounts for only ~1.3% of cotton harvested in the U.S. because of low yields. (ii) Net costs of drought penalties, and value-added worth potential of AtRAV transgenics, can be estimated from typical spot premiums paid for lint with $2/32^{nd}$ inch (~6%) longer staple, which are on the order of ~four U.S. cents a pound (www.ams.usda.gov/mnreports/cnddsq.pdf), with west Texas typically contributing ~3 million bales (500 pounds/bale) toward the ~120 million bales produced annually worldwide.

It is plausible that the dynamic drought recovery of GhFTL expression in the AtRAV1 and AtRAV2 transgenics (>2-fold increased over control; FIG. 8b, lanes 13-17 vs. lane 18) may account for why AtRAV1, AtRAV2 and RAV×ABI5 stacked transgenics flower earlier (but still later than wild type) in response to imposed drought (FIG. 2a, 2b). Taken together with the finding that FT and its close homologue TSF function cell-autonomously in guard cells to regulate stomatal opening (Ando et al. 2013; Kinoshita et al. 2011), these results showing GhFTL down regulation in AtRAV1- and AtRAV2 cotton under well-watered and drought stress conditions, yet elevated expression during drought recovery (FIG. 8a, 8b), suggest the 'less-stressed' phenotype is by AtRAV repression of GhFTL or GhTFS-Like. This model is further corroborated by the drought-, salt-, and ABA induction of a Zea mays RAV1 homologue, and that overexpression of ZmRAV1 in Arabidopsis confers salt- and osmotic stress tolerance and longer roots (Min et al. 2014), similar to the inventors' prior demonstration in maize protoplasts and transgenic cotton that RAVs are positive effectors of ABA responses (Mittal et al. 2014). Also consistent with this interpretation is the recent finding that Arabidopsis rav2l/tem1 knockout mutant is less sensitive to sucrose inhibition of root growth (Lu et al. 2014). However, a recent report claimed that Arabidopsis RAV1 functions in stress response in an ABA-independent matter, despite overexpressor lines accumulating higher salt-induced levels of ABA in seeds and drought-response marker genes while exhibiting decreased root growth repression and stomatal closure (Fu et al. 2014), consistent with these prior results (Mittal et al. 2014) for AtRAV1 and AtRAV2 overexpression in drought-stressed cotton. Again, by way of explanation and in no way a limitation of the present invention, the inventors suggest an alternative interpretation of others' results for Arabidopsis: improved photoassimilation and root and shoot sink strengths associated with enhanced expression of endogenous RAVs and genes for antioxidant (GST) and osmolyte biosynthesis (PSC5) result in a 'less stressed' phenotype (Mittal et al. 2014). This possible model is generally consistent with a recent report demonstrating AtRAV1 represses ABI3, ABI4, and ABI5 in seedlings by binding to those promoters and is subject to SnRK2 phosphorylation to positively modulate ABA responses (Feng et al. 2014). ABA is associated with increases in catalase, $H_2O_2$, and mitogen-activated protein kinase6 expression during cotton fiber development (Luo et al. 2011) and elongation (Kim et al. 2013; Nigam et al. 2014; Padmalatha et al. 2012). Recent transcriptome analyses resulted in the proposition that domestication of G. hirsutum resulted in a shift or reallocation of resources from stress-related pathways in wild cottons (inversely correlated with MYB2, MYB25, MYB25L, MYB109, and GhHD-1 expression, but not GhRDL1) to prolonged growth in domesticated varieties (Yoo & Wendel 2014). These results showing a functional link between exogenous RAV transgenes and endogenous GhRAV2L expression and stress pathways (Mittal et al. 2014) and these key MYB effectors (but not RDL1)(FIG. 10) whose temporal expression correlates with longer fibers especially under drought stress (FIG. 5, 6a-6c) without appreciable yield penalties (FIG. 7a-7c) support the stress-to-assimilate-pathways shift hypothesis, where stress-related gene expression marks an inhibition of fiber elongation (Yoo & Wendel 2014). The present invention can be used to further establish molecular mechanisms of ABA homeostasis by RAVs and conservation of functions between species.

MYB TFs are associated with fiber cell development (Cedroni et al. 2003; Loguerico et al. 1999; Pu et al. 2008; Wang et al. 2004), where it has been shown that GhMYB2 is expressed at low levels in outer integuments and fibers of ovules at 0 DPA, lower at 3 DPA, followed by strong up-regulation at 5-10 DPA (Guan et al. 2014; Huang et al. 2013b). GhMYB25 is expressed maximally at 0 DPA and drops ~40% at 2 DPA and >90% at 5 DPA (Machado et al. 2009). GhMYB25L is expressed in developing ovules at -2 DPA, with much increased expression at -1 DPA ovules and in elongating fibers until 3 DPA, when expression drops to ~25% from 4 DPA until 10 DPA (Walford et al. 2011). GhMYB25L is a key effector of fiber initiation acting upstream of GhHD-1 (Bedon et al. 2014; Walford et al. 2012). Longer lint fiber in AtRAV1 and AtRAV2 overexpressing cotton lines is possibly a direct or indirect consequence of increased expression of known MYB effectors of fiber initiation and elongation in ovules because in multiple independent lines of AtRAV1 and AtRAV2 (FIG. 1a, 1b, FIG. 9) GhRAV2L was significantly elevated (FIG. 10a, 10b) prior to or when significantly elevated effector MYB, but not GhRDL1, expressions were observed. Quantification of fiber initials in these transgenics may provide supportive evidence for this mechanism.

Regarding molecular mechanisms underlying fiber qualities, it is intriguing that miR828 negatively regulates expression of GhMYB2 early (0-3 DPA) in fiber development (Guan et al. 2014) and is predicted to target GhMYB109, which also functions in fiber elongation (Pu et al. 2008) and both genes are differentially expressed between wild and domesticated cottons (Yoo & Wendel 2014). At pre-anthesis stage (-3 DPA) the inventors observed AtRAV1 and AtRAV2 transgenic ovules had higher MYB2 expression in addition to significantly elevated expression in AtRAV2 at 0 DPA, and significantly higher MYB2 expression in both transgenic lines at 15 DPA (FIG. 10b), the time when fiber secondary wall synthesis occurs. WLIM1 translocates to the nucleus in response to the oxidative burst that occurs during the transition from elongation to secondary wall synthesis in developing fibers (Potikha et al. 1999; Zhang et al. 2010a) to transactivate Phe ammonia lyase-box genes involved in phenylpropanoid and lignin biosynthesis that build up the secondary cell wall (Han et al. 2013). The inventors have shown that miR828 is deeply conserved in dicots and gymnosperms where target MYBs are effectors of fruit development and polyphenolic synthesis (Rock 2013) and participate in an auto-regulatory loop (Luo et al. 2012) to amplify post-transcriptional gene silencing of developmental or biotic stress pathways (Kallman et al. 2013; Velten et al. 2012). The functional significance of these post-transcriptional processes in cotton fiber (Guan et al. 2014) and fruit development in other species (Rock 2013) remain to be established. Based on these expression data (FIG. 10a, 10b), it is possible, but not a limitation of the present invention, that GhRAV2L and AtRAVs might function as negative regulators of GhMIR828 and/or other miRNAs such as GhMIR156 (Liu et al. 2014c) or GhMIR397, which is expressed in fiber initials and targets laccases involved in lignin biosynthesis (Wang et al. 2012e). Likewise, drought stress (Li et al. 2008), ABA responses (Jia & Rock 2013; Jia et al. 2009b), seed maturation (Reyes & Chua 2007), and flowering time (Hu et al. 2014; Kim & Ahn 2014; Spanudakis & Jackson 2014) are processes subject to miRNA regulation which may contribute to the observed phenotypes of AtRAV1 and AtRAV2 over-expressing cotton for vegetative stress adaptation, biomass accumulation, and delayed flowering and boll maturation. Evidence consistent with this model is that RAV2 is required for suppression of RNA silencing by unrelated plant viral proteins potyvirus HC-Pro and carmovirus P38 (Endres et al. 2010), and FT is subject to miRNA regulation in Brachypodium (Wu et al. 2013).

Bioinformatic mining and imputation to crops of established RAV interactions with TOPLESS/TPR and other (e.g. ABA) processes using systems biology databases (Arabidopsis Interactome Mapping Consortium 2011; Bassel et al. 2012; Causier et al. 2012; Choi et al. 2013; Geisler-Lee et al.

2007; Lee et al. 2014; Lumba et al. 2014; Szklarczyk et al. 2011; Van Landeghem et al. 2013) can provide new predictions about the mechanisms of RAV regulation (e.g. by epigenetic chromatin remodeling) and facilitate the identification of further regulatory factors functioning in fiber development and other quantitative traits. For example, TOPLESS epigenetically mediates the inhibitory action of brassinosteroids on ABA responses via ABI3 histone deacetylation during early seedling development (Ryu et al. 2014). Crosstalk between brassinosteroid and ABA signaling has recently been shown to involve glycogen synthase kinase 3 (GSK3)-like activation of SnRK2s (Cai et al. 2014). GhHD-1, which physically interacts with GhMYB25 (Walford et al. 2012), is a member of a class of TFs whose functions are increasingly recognized as aligning morphogenesis and environmental responses by modulating phytohormone-signaling networks (Brandt et al. 2014). FLOWERING BASIC-HELIX-LOOP-HELIX3 (FBH3), which positively regulates expression of photoperiodic flowering gene CO (Ito et al. 2012) and activates stomatal opening (Takahashi et al. 2013), was among 84 phosphopeptides identified as possible substrates of SRK2D/E/I protein kinases involved in ABA signaling (Yoshida et al. 2014), miRNA and epigenetic regulation, and flowering time (Wang et al. 2013b). Other relationships to consider in this context are that FT mRNA stability is modulated non cell autonomously by the WEREWOLF MYB which functions in root trichome patterning (Seo et al. 2011). MYB56 is a novel target of a CULLIN3 (CUL3)-based E3 ligase acting at the promoter of FT (Chen et al. 2014) which is subject to natural allelic variation (Liu et al. 2014a), whereas ectopic expression in phloem of MYB30, a positive regulator of the pathogen-induced hypersensitive response and of brassinosteroid and ABA signaling, accelerates flowering by elevating expression of FT (Liu et al. 2014b). By manipulating FT expression it may be possible to alter the transition from vegetative meristems to flowers for enhanced synchronized maturation, focused application of inputs, and homogeneous fiber quality and other agronomic traits. It is possible that similar mechanisms operate to control cell expansion and patterning in different tissue types (e.g. roots and fibers) impacted by AtRAV1 and AtRAV2 overexpression, and underlie the extremely longer fibers produced by *G. barbadense* (Fang et al. 2014). The subject transgenic lines can also be used as a powerful tool to examine the molecular and physiological mechanisms of environmental stress adaptation and developmental pathways important for agronomic traits like root and fruit biomass.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Abdurakhmonov I. Y., Buriev Z. T., Saha S., Jenkins J. N., Abdukarimov A., Pepper A. E. (2014) Phytochrome RNAi enhances major fibre quality and agronomic traits of the cotton *Gossypium hirsutum* L. Nature Communications 5, e3062.

Ando E., Ohnishi M., Wang Y., Matsushita T., Watanabe A., Hayashi Y., Kinoshita T. (2013) TWIN SISTER OF FT, GIGANTEA, and CONSTANS have a positive but indirect effect on blue light-induced stomatal opening in *Arabidopsis*. Plant Physiology 162, 1529-1538.

*Arabidopsis* Interactome Mapping Consortium (2011) Evidence for network evolution in an *Arabidopsis* interactome map. Science 333, 601-607.

Arpat A., Waugh M., Sullivan J., Gonzales M., Frisch D., Main D., Wilkins T. (2004) Functional genomics of cell elongation in developing cotton fibers. Plant Molecular Biology 54, 911-929.

Bai W.-Q., Xiao Y.-H., Zhao J., Song S.-Q., Hu L., Zeng J.-Y., Pei Y. (2014) Gibberellin overproduction promotes sucrose synthase expression and secondary cell wall deposition in cotton fibers. PLoS ONE 9, e96537.

Basra A. S. & Saha S. (1999) Growth regulation of cotton fibers. In: Cotton Fibers: Developmental Biology, Quality Improvement, and Textile Processing (ed A. S. Basra), pp. 47-58. Haworth Press, New York.

Bassel G. W., Gaudinier A., Brady S. M., Hennig L., Rhee S. Y. & De Smet I. (2012) Systems analysis of plant functional, transcriptional, physical interaction, and metabolic networks. Plant Cell 24, 3859-3875.

Bayley C., Trolinder N., Ray C., Morgan M., Quisenberry J. E. & Ow D. W. (1992) Engineering 2,4-D resistance into cotton. Theoretical and Applied Genetics 83, 645-649.

Bedon F., Ziolkowski L., Walford S. A., Dennis E. S. & Llewellyn D. J. (2014) Members of the MYBMIXTA-like transcription factors may orchestrate the initiation of fibre development in cotton seeds. Frontiers in Plant Science 5, e179. doi: 110.3389/fpls.2014.00179.

Belda-Palazón B., Nohales M. A., Rambla J. L., Aceña J. L., Delgado O., Fustero S., Ferrando A. (2014) Biochemical quantitation of the eIF5A hypusination in *Arabidopsis thaliana* uncovers ABA-dependent regulation. Frontiers in Plant Science 5, e202.

Bourland F. M., Johnson J. T. & Jones D. C. (2005) Registration of Arkot 8712 germplasm line of cotton. Crop Science 45, 1173-1174.

Bourland F. M. & Jones D. C. (2012) Registration of 'UA48' cotton cultivar. Journal of Plant Registrations 6, 15-18.

Boyer J. S. (1982) Plant productivity and environment. Science 218, 443-448.

Brandt R., Cabedo M., Xie Y. & Wenkel S. (2014) Homeodomain leucine-zipper proteins and their role in synchronizing growth and development with the environment. Journal of Integrative Plant Biology 56, 518-526.

Braxton-Little J. (2009) Saving the Ogallala Aquifer. Scientific American 19, 32-39.

Brocard I. M., Lynch T. J. & Finkelstein R. R. (2002) Regulation and role of the *Arabidopsis* Abscisic Acid-Insensitive 5 gene in abscisic acid, sugar, and stress response. Plant Physiology 129, 1533-1543.

Cai Z., Liu J., Wang H., Yang C., Chen Y., Li Y., Wang X. (2014) GSK3-like kinases positively modulate abscisic acid signaling through phosphorylating subgroup III SnRK2s in *Arabidopsis*. Proceedings of the National Academy of Sciences, U.S.A. 111, 9651-9656.

Castillejo C. & Pelaz S. (2008) The balance between CONSTANS and TEMPRANILLO activities determines FT expression to trigger flowering. Current Biology 18, 1338-1343.

Causier B., Ashworth M., Guo W. & Davies B. (2012) The TOPLESS interactome: a framework for gene repression in *Arabidopsis*. Plant Physiology 158, 423-438.

Cedroni M. L., Cronn R. C., Adams K. L., Wilkins T. A. & Wendel J. F. (2003) Evolution and expression of MYB genes in diploid and polyploid cotton. Plant Molecular Biology 51, 313-325.

Chen L., Bernhardt A., Lee J. & Hellmann H. (2015) Identification of *Arabidopsis* MYB56 as a novel substrate for CRL3BPM E3 ligases. Molecular Plant, 8, 242-250.

Chen X., Wang Z., Wang X., Dong J., Ren J. & Gao H. (2009) Isolation and characterization of GoRAV, a novel gene encoding a RAV-type protein in *Galegae orientalis*. Genes and Genetic Systems 84, 101-109.

Choi D., Choi J., Kang B., Lee S., Cho Y.-h., Hwang I. & Hwang D. (2013) iNID: an analytical framework for identifying network models for interplays among developmental signaling in *Arabidopsis*. Molecular Plant 7, 792-813.

Culp T. W. & Harrell D. C. (1975) Influence of lint percentage, boll size, and seed size on lint yield of upland cotton with high fiber strength. Crop Science 15, 741-746.

Deng F., Tu L., Tan J., Li Y., Nie Y. & Zhang X. (2012) GbPDF1 is involved in cotton fiber initiation via the core cis-element HDZIP2ATATHB2. Plant Physiology 158, 890-904.

Deng W., Ying H., Helliwell C. A., Taylor J. M., Peacock W. J. & Dennis E. S. (2011) FLOWERING LOCUS C (FLC) regulates development pathways throughout the life cycle of *Arabidopsis*. Proceedings of the National Academy of Sciences, U.S.A. 108, 6680-6685.

Ding M., Jiang Y., Cao Y., Lin L., He S., Zhou W. & Rong J. (2014) Gene expression profile analysis of Ligon lintless-1 (Li1) mutant reveals important genes and pathways in cotton leaf and fiber development. Gene 535, 273-285.

Endres M. W., Gregory B. D., Gao Z. H., Foreman A. W., Mlotshwa S., Ge X., Vance V. (2010) Two plant viral suppressors of silencing require the ethylene-inducible host transcription factor RAV2 to block RNA silencing. PLoS Pathogens 6, 12.

Fang L., Tian R., Li X., Chen J., Wang S., Wang P. & Zhang T. (2014) Cotton fiber elongation network revealed by expression profiling of longer fiber lines introgressed with different *Gossypium barbadense* chromosome segments. BMC Genomics 15, 838.

Feng C.-Z., Chen Y., Wang C., Kong Y.-H., Wu W.-H. & Chen Y.-F. (2014) *Arabidopsis* RAV1 transcription factor, phosphorylated by SnRK2 kinases, regulates the expression of ABI3, ABI4, and ABI5 during seed germination and early seedling development. Plant Journal 80, 654-668.

Finkelstein R., Gampala S. S. L., Lynch T. J., Thomas T. L. & Rock C. D. (2005) Redundant and distinct functions of the ABA response loci ABA-INSENSITIVE(ABI)5 and ABRE-BINDING FACTOR (ABF)3. Plant Molecular Biology 59, 253-267.

Fu M., Kang H. K., Son S.-H., Kim S.-K. & Nam K. H. (2014) A subset of RAV transcription factors modulates drought and salt stress responses ABA-independently in *Arabidopsis*. Plant and Cell Physiology 55, 1892-1904.

Geisler-Lee J., O'Toole N., Ammar R., Provart N. J., Millar A. H. & Geisler M. (2007) A predicted interactome for *Arabidopsis*. Plant Physiology 145, 317-329.

Gilbert M. K., Bland J. M., Shockey J. M., Cao H., Hinchliffe D. J., Fang D. D. & Naoumkina M. (2013) A transcript profiling approach reveals an abscisic acid-specific glycosyltransferase (UGT73C14) induced in developing fiber of Ligon lintless-2 mutant of cotton (*Gossypium hirsutum* L.). PLoS ONE 8, e75268.

Gilbert M. K., Kim H. J., Tang Y., Naoumkina M. & Fang D. D. (2014) Comparative transcriptome analysis of short fiber mutants Ligon-Lintless 1 And 2 reveals common mechanisms pertinent to fiber elongation in cotton (*Gossypium hirsutum* L.). PLoS ONE 9, e95554.

Giraudat J., Hauge B. M., Valon C., Smalle J., Parcy F. & Goodman H. M. (1992) Isolation of the *Arabidopsis* ABI3 gene by positional cloning. Plant Cell 4, 1251-1261.

Gregory K., Ng E. H., Smith W., Hequet E. & Hague S. (2012) Fiber and yarn performance of upland cotton with improved fiber bundle strength. Crop Science 52, 1061-1067.

Gu X., Wang Y. & He Y. (2013) Photoperiodic regulation of flowering time through periodic histone deacetylation of the florigen gene FT. PLoS Biology 11, e1001649.

Guan X., Pang M., Nah G., Shi X., Ye W., Stelly D. M. & Chen Z. J. (2014) miR828 and miR858 regulate homoeologous MYB2 gene functions in *Arabidopsis* trichome and cotton fibre development. Nature Communications 5, 3050.

Guo H. & Ecker J. R. (2003) Plant responses to ethylene gas are mediated by SCFEBF1/EBF2-dependent proteolysis of EIN3 transcription factor. Cell 115, 667-677.

Han J., Tan J., Tu L. & Zhang X. (2014) A peptide hormone gene, GhPSK promotes fibre elongation and contributes to longer and finer cotton fibre. Plant Biotechnology Journal 12, 861-871.

Han L.-B., Li Y.-B., Wang H.-Y., Wu X.-M., Li C.-L., Luo M., Xia G.-X. (2013) The dual functions of WLIM1a in cell elongation and secondary wall formation in developing cotton fibers. Plant Cell 25, 4421-4438.

Hao J., Tu L., Hu H., Tan J., Deng F., Tang W., Zhang X. (2012) GbTCP, a cotton TCP transcription factor, confers fibre elongation and root hair development by a complex regulating system. Journal of Experimental Botany 63, 6267-6281.

Hobo T., Kowyama Y. & Hattori T. (1999) A bZIP factor, TRAB1, interacts with VP1 and mediates abscisic acid-induced transcription. Proceedings of the National Academy of Sciences, U.S.A. 96, 15348-15353.

Hu J.-Y., Zhou Y., He F., Dong X., Liu L.-Y., Coupland G., de Meaux J. (2014) miR824-regulated AGAMOUS-LIKE16 contributes to flowering time repression in *Arabidopsis*. Plant Cell 26, 2024-2037.

Hu Y. X., Wang Y. H., Liu X. F. & Li J. Y. (2004) *Arabidopsis* RAV1 is down-regulated by brassinosteroid and may act as a negative regulator during plant development. Cell Research 14, 8-15.

Huang G.-Q., Gong S.-Y., Xu W.-L., Li W., Li P., Zhang C.-J., Li X.-B. (2013a) A fasciclin-like arabinogalactan protein, GhFLA1, is involved in fiber initiation and elongation of cotton. Plant Physiology 161, 1278-1290.

Huang Y., Liu X., Tang K. & Zuo K. (2013b) Functional analysis of the seed coat-specific gene GbMYB2 from cotton. Plant Physiology and Biochemistry 73, 16-22.

Ikeda M. & Ohme-Takagi M. (2009) A novel group of transcriptional repressors in *Arabidopsis*. Plant and Cell Physiology 50, 970-975.

Ito S., Song Y. H., Josephson-Day A. R., Miller R. J., Breton G., Olmstead R. G. & Imaizumi T. (2012) FLOWERING BHLH transcriptional activators control expression of the photoperiodic flowering regulator CONSTANS in *Arabidopsis*. Proceedings of the National Academy of Sciences, U.S.A. 109, 3582-3587.

Je B. I., Piao H. L., Park S. J., Park S. H., Kim C. M., Xuan Y. H., Han C.-d. (2010) RAV-Likel maintains brassinosteroid homeostasis via the coordinated activation of BRI1 and biosynthetic genes in rice. Plant Cell 22, 1777-1791.

Jeong J.-H., Song H.-R., Ko J.-H., Jeong Y.-M., Kwon Y. E., Seol J. H., Noh Y.-S. (2009) Repression of FLOWERING_LOCUS_T chromatin by functionally redundant histone H3 lysine 4 demethylases in *Arabidopsis*. PLoS ONE 4, e8033.

Jia F., Gampala S. L., Mittal A., Luo Q. & Rock C. (2009a) Cre-lox univector acceptor vectors for functional screening in protoplasts: analysis of *Arabidopsis* donor cDNAs encoding ABSCISIC ACID INSENSITIVE'-like protein phosphatases. Plant Molecular Biology 70, 693-708.

Jia F. & Rock C. D. (2013) Jacalin lectin At5g28520 is regulated by ABA and miR846. Plant Signaling & Behavior 8, e24563.

Jia X., Wang W.-X., Ren L., Chen Q.-J., Mendu V., Willcut B., Tang G. (2009b) Differential and dynamic regulation of miR398 in response to ABA and salt stress in *Populus tremula* and *Arabidopsis thaliana*. Plant Molecular Biology 71, 51-59.

Jiang Y., Guo W., Zhu H., Ruan Y.-L. & Zhang T. (2012) Overexpression of GhSusA1 increases plant biomass and improves cotton fiber yield and quality. Plant Biotechnology Journal 10, 301-312.

Kagaya Y. & Hattori T. (2009) *Arabidopsis* transcription factors, RAV1 and RAV2, are regulated by touch-related stimuli in a dose-dependent and biphasic manner. Genes and Genetic Systems 84, 95-99.

Kagaya Y., Ohmiya K. & Hattori T. (1999) RAV1, a novel DNA-binding protein, binds to bipartite recognition sequence through two distinct DNA-binding domains uniquely found in higher plants. Nucleic Acids Research 27, 470-478.

Källman T., Chen J., Gyllenstrand N. & Lagercrantz U. (2013) A significant fraction of 21 nt sRNA originates from phased degradation of resistance genes in several perennial species. Plant Physiology 162, 741-754.

Kim H., Tang Y., Moon H., Delhom C. & Fang D. (2013) Functional analyses of cotton (*Gossypium hirsutum* L.) immature fiber (im) mutant infer that fiber cell wall development is associated with stress responses. BMC Genomics 14, 889.

Kim H. J. & Triplett B. A. (2001) Cotton fiber growth in planta and in vitro. Models for plant cell elongation and cell wall biogenesis. Plant Physiology 127, 1361-1366.

Kim W. & Ahn J. H. (2014) MicroRNA-target interactions: important signaling modules regulating flowering time in diverse plant species. Critical Reviews in Plant Sciences 33, 470-485.

Kinoshita T., Ono N., Hayashi Y., Morimoto S., Nakamura S., Soda M., Shimazaki K.-i. (2011) FLOWERING LOCUS T regulates stomatal opening. Current Biology 21, 1232-1238.

Laurie R. E., Diwadkar P., Jaudal M., Zhang L., Hecht V., Wen J., Macknight R. C. (2011) The Medicago FLOWERING LOCUS T homolog, MtFTa1, is a key regulator of flowering time. Plant Physiology 156, 2207-2224.

Lee S., Choi D., Hwang I. & Hwang B. (2010) The pepper oxidoreductase CaOXR1 interacts with the transcription factor CaRAV1 and is required for salt and osmotic stress tolerance. Plant Molecular Biology 73, 409-424.

Lee T., Yang S., Kim E., Ko Y., Hwang S., Shin J., Lee I. (2014) AraNet v2: an improved database of co-functional gene networks for the study of *Arabidopsis thaliana* and 27 other nonmodel plant species. Nucleic Acids Research, 43, D996-D1002.

Li C.-W., Su R.-C., Cheng C.-P., Sanjaya, You S.-J., Hsieh T.-H., Chan M.-T. (2011) Tomato RAV transcription factor is a pivotal modulator involved in the AP2/EREBP-mediated defense pathway. Plant Physiology 156, 213-227.

Li F., Fan G., Wang K., Sun F., Yuan Y., Song G., Yu S. (2014) Genome sequence of the cultivated cotton *Gossypium arboreum*. Nature Genetics 46, 567-572.

Li W.-X., Oono Y., Zhu J., He X.-J., Wu J.-M., Iida K., Zhu J.-K. (2008) The *Arabidopsis* NFYA5 transcription factor is regulated transcriptionally and posttranscriptionally to promote drought resistance. Plant Cell 20, 2238-2251.

Li X., Yuan D., Zhang J., Lin Z. & Zhang X. (2013) Genetic mapping and characteristics of genes specifically or preferentially expressed during fiber development in cotton. PLoS ONE 8, e54444.

Liu K., Sun J., Yao L. & Yuan Y. (2012) Transcriptome analysis reveals critical genes and key pathways for early cotton fiber elongation in Ligon lintless-1 mutant. Genomics 100, 42-50.

Liu L., Adrian J., Pankin A., Hu J., Dong X., von Korff M. & Turck F. (2014a) Induced and natural variation of promoter length modulates the photoperiodic response of FLOWERING LOCUS T. Nature Communications 5, e4558. doi:4510.1038/ncomms5558.

Liu L., Zhang J., Adrian J., Gissot L., Coupland G., Yu D. & Turck F. (2014b) Elevated levels of MYB30 in the phloem accelerate flowering in *Arabidopsis* through the regulation of FLOWERING LOCUS T. PLoS ONE 9, e89799.

Liu N., Tu L., Tang W., Gao W., Lindsey K. & Zhang X. (2014c) Small RNA and degradome profiling reveals a role for miRNAs and their targets in the developing fibers of *Gossypium barbadense*. Plant Journal 80, 331-344.

Loguerico L. L., Zhang J. Q. & Wilkins T. A. (1999) Differential regulation of six novel MYB-domain genes defines two distinct expression patterns in allotetraploid cotton (*Gossypium hirsutum* L.). Molecular and General Genetics 261, 660-671.

Lu Q., Zhao L., Li D., Hao D., Zhan Y. & Li W. (2014) A GmRAV ortholog is involved in photoperiod and sucrose control of flowering time in soybean. PLoS ONE 9, e89145.

Lumba S., Toh S., Handfield L.-F., Swan M., Liu R., Youn J.-Y., McCourt P. (2014) A mesoscale abscisic acid hormone interactome reveals a dynamic signaling landscape in *Arabidopsis*. Developmental Cell 29, 360-372.

Luo J., Zhao L.-L., Gong S.-Y., Sun X., Li P., Qin L.-X., Li X.-B. (2011) A cotton mitogen-activated protein kinase (GhMPK6) is involved in ABA-induced CAT1 expression and H2O2 production. Journal of Genetics and Genomics 38, 557-565.

Luo M., Xiao Y., Li X., Lu X., Deng W., Li D., Pei Y. (2007) GhDET2, a steroid 5α-reductase, plays an important role in cotton fiber cell initiation and elongation. Plant Journal 51, 419-430.

Luo Q.-J., Mittal A., Jia F. & Rock C. D. (2012) An autoregulatory feedback loop involving PAP1 and TAS4 in response to sugars in *Arabidopsis*. Plant Molecular Biology 80, 117-129.

Machado A., Wu Y., Yang Y., Llewellyn D. J. & Dennis E. S. (2009) The MYB transcription factor GhMYB25 regulates early fibre and trichome development. Plant Journal 59, 52-62.

Matias-Hernandez L., Aguilar-Jaramillo A. E., Marin-Gonzalez E., Suarez-Lopez P. & Pelaz S. (2014) RAV genes: regulation of floral induction and beyond. Annals of Botany 114, 1459-1470.

Matsoukas I. G., Massiah A. J. & Thomas B. (2012) Florigenic and antiflorigenic signaling in plants. Plant and Cell Physiology 53, 1827-1842.

McCarty D. R., Hattori T., Carson C. B., Vasil V., Lazar M. & Vasil I. K. (1991) The Viviparous-1 developmental gene of maize encodes a novel transcriptional activator. Cell 66, 895-905.

McGarry R. C. & Ayre B. G. (2012) Geminivirus-mediated delivery of florigen promotes determinate growth in aerial organs and uncouples flowering from photoperiod in cotton. PLoS ONE 7, e36746.

McGarry R. C., Prewitt S. & Ayre B. G. (2013) Overexpression of FT in cotton affects architecture but not floral organogenesis. Plant Signaling & Behavior 8, e23602.

Min H., Zheng J. & Wang J. (2014) Maize ZmRAV1 contributes to salt and osmotic stress tolerance in transgenic *Arabidopsis*. Journal of Plant Biology 57, 28-42.

Mittal A., Gampala S. S. L., Ritchie G. L., Payton P., Burke J. J. & Rock C. D. (2014) Related to ABA-Insensitive3 (ABI3)/Viviparous1 and AtABI5 transcription factor coexpression in cotton enhances drought stress adaptation. Plant Biotechnology Journal 12, 578-589.

Moreno-Cortês A., Hernández-Verdeja T., Sânchez-Jiménez P., González-Melendi P., Aragoncillo C. & Allona I. (2012) CsRAV1 induces sylleptic branching in hybrid poplar. New Phytologist 194, 83-90.

Mutasa-Gottgens E., Joshi A., Holmes H., Hedden P. & Gottgens B. (2012) A new RNASeq-based reference transcriptome for sugar beet and its application in transcriptome-scale analysis of vernalization and gibberellin responses. BMC Genomics 13, 99.

Naoumkina M., Thyssen G., Fang D. D., Hinchliffe D. J., Florane C., Yeater K. M., Udall J. A. (2014) The Li2 mutation results in reduced subgenome expression bias in elongating fibers of allotetraploid cotton (*Gossypium hirsutum* L.). PLoS ONE 9, e90830.

Nigam D., Kavita P., Tripathi R. K., Ranjan A., Goel R., Asif M., Sawant S. V. (2014) Transcriptome dynamics during fibre development in contrasting genotypes of *Gossypium hirsutum* L. Plant Biotechnology Journal 12, 204-218.

Osnato M., Castillejo C., Matias-Hernández L. & Pelaz S. (2012) TEMPRANILLO genes link photoperiod and gibberellin pathways to control flowering in *Arabidopsis*. Nature Communications 3, 808.

Padmalatha K., Dhandapani G., Kanakachari M., Kumar S., Dass A., Patil D., Kumar P. (2012) Genome-wide transcriptomic analysis of cotton under drought stress reveal significant down-regulation of genes and pathways involved in fibre elongation and up-regulation of defense responsive genes. Plant Molecular Biology 78, 223-246.

Parkash J., Vaidya T., Kirti S. & Dutt S. (2014) Translation initiation factor 5A in Picrorhiza is up-regulated during leaf senescence and in response to abscisic acid. Gene 542, 1-7.

Pettigrew W. T. (2004) Moisture deficit effects on cotton lint yield, yield components, and boll distribution. Agronomy Journal 96, 377-383.

Potikha T. S., Collins C. C., Johnson D. I., Delmer D. P. & Levine A. (1999) The involvement of hydrogen peroxide in the differentiation of secondary walls in cotton fibers. Plant Physiology 119, 849-858.

Pu L., Li Q., Fan X., Yang W. & Xue Y. (2008) The R2R3 MYB transcription factor GhMYB109 is required for cotton fiber development. Genetics 180, 811-820.

Qu J., Ye J., Geng Y.-F., Sun Y.-W., Gao S.-Q., Zhang B.-P., Chua N.-H. (2012) Dissecting functions of KATANIN and WRINKLED1 in cotton fiber development by virus-induced gene silencing. Plant Physiology 160, 738-748.

Reyes J. L. & Chua N. H. (2007) ABA induction of miR159 controls transcript levels of two MYB factors during *Arabidopsis* seed germination. Plant Journal 49, 592-606.

Riboni M., Galbiati M., Tonelli C. & Conti L. (2013) GIGANTEA enables drought escape response via abscisic acid-dependent activation of the Florigens and SUPPRESSOR OF OVEREXPRESSION OF CONSTANS. Plant Physiology 162, 1706-1719.

Rock C. D. (2013) Trans-acting small interfering RNA4: key to nutraceutical synthesis in grape development? Trends in Plant Science 18, 601-610.

Ryu H., Cho H., Bae W. & Hwang I. (2014) Control of early seedling development by BES1/TPL/HDA19-mediated epigenetic regulation of ABI3. Nature Communications 5, e4138. doi:4110.1038/ncomms5138.

Sawa M. & Kay S. A. (2011) GIGANTEA directly activates Flowering Locus T in *Arabidopsis thaliana*. Proceedings of the National Academy of Sciences, U.S.A. 108, 11698-11703.

Seo E., Yu J., Ryu K. H., Lee M. M. & Lee I. (2011) WEREWOLF, a regulator of root hair pattern formation, controls flowering time through the regulation of FT mRNA stability. Plant Physiology 156, 1867-1877.

Sgamma T., Jackson A., Muleo R., Thomas B. & Massiah A. (2014) TEMPRANILLO is a regulator of juvenility in plants. Scientific Reports 4, e3704. DOI: 3710.1038/srep03704.

Shi Y.-H., Zhu S.-W., Mao X.-Z., Feng J.-X., Qin Y.-M., Zhang L., Zhu Y.-X. (2006) Transcriptome profiling, molecular biological, and physiological studies reveal a major role for ethylene in cotton fiber cell elongation. Plant Cell 18, 651-664.

Spanudakis E. & Jackson S. (2014) The role of microRNAs in the control of flowering time. Journal of Experimental Botany 65, 365-380.

Sun F., Liu C., Zhang C., Qi W., Zhang X., Wu Z., Yang J. (2012) A conserved RNA recognition motif (RRM) domain of *Brassica napus* FCA improves cotton fiber quality and yield by regulating cell size. Molecular Breeding 30, 93-101.

Sunilkumar G., Mohr L., Lopata-Finch E., Emani C. & Rathore K. (2002) Developmental and tissue-specific expression of CaMV 35S promoter in cotton as revealed by GFP. Plant Molecular Biology 50, 463-479.

Szklarczyk D., Franceschini A., Kuhn M., Simonovic M., Roth A., Minguez P., Mering C. v. (2011) The STRING database in 2011: functional interaction networks of proteins, globally integrated and scored. Nucleic Acids Research 39, D561-D568.

Takahashi Y., Ebisu Y., Kinoshita T., Doi M., Okuma E., Murata Y. & Shimazaki K.-i. (2013) bHLH transcription factors that facilitate K+ uptake during stomatal opening are repressed by abscisic acid through phosphorylation. Science Signaling 6, ra48.

Tan J., Tu L., Deng F., Hu H., Nie Y. & Zhang X. (2013) A genetic and metabolic analysis revealed that cotton fiber cell development was retarded by flavonoid naringenin. Plant Physiology 162, 86-95.

Tang W., Tu L., Yang X., Tan J., Deng F., Hao J., Zhang X. (2014) The calcium sensor GhCaM7 promotes cotton fiber elongation by modulating reactive oxygen species (ROS) production. New Phytologist 202, 509-520.

Thyssen G. N., Song X., Naoumkina M., Kim H.-J. & Fang D. D. (2014) Independent replication of mitochondrial genes supports the transcriptional program in developing fiber cells of cotton (*Gossypium hirsutum* L.). Gene 544, 41-48.

Unruh B. L. & Silvertooth J. C. (1997) Planting and irrigation termination timing effects on the yield of upland and pima cotton. Journal of Production Agriculture 10, 74-79.

Van Landeghem S., De Bodt S., Drebert Z. J., Inzé D. & Van de Peer Y. (2013) The potential of text mining in data integration and network biology for plant research: a case study on *Arabidopsis*. Plant Cell 25, 794-807.

Velten J., Cakir C., Youn E., Chen J. & Cazzonelli C. I. (2012) Transgene silencing and transgene-derived siRNA production in tobacco plants homozygous for an introduced AtMYB90 construct. PLoS ONE 7, e30141.

Walford S.-A., Wu Y., Llewellyn D. J. & Dennis E. S. (2011) GhMYB25-like: a key factor in early cotton fibre development. Plant Journal 65, 785-797.

Walford S.-A., Wu Y., Llewellyn D. J. & Dennis E. S. (2012) Epidermal cell differentiation in cotton mediated by the homeodomain leucine zipper gene, GhHD-1. Plant Journal 71, 464-478.

Wan Q., Zhang H., Ye W., Wu H. & Zhang T. (2014) Genome-wide transcriptome profiling revealed cotton fuzz fiber development having a similar molecular model as *Arabidopsis* trichome. PLoS ONE 9, e97313.

Wang C., Lv Y., Xu W., Zhang T. & Guo W. (2014a) Aberrant phenotype and transcriptome expression during fiber cell wall thickening caused by the mutation of the Im gene in immature fiber (im) mutant in *Gossypium hirsutum* L. BMC Genomics 15, 94.

Wang G., Zhu Q., Meng Q. & Wu C. (2012a) Transcript profiling during salt stress of young cotton (*Gossypium hirsutum*) seedlings via Solexa sequencing. Acta Physiologiae Plantarum 34, 107-115.

Wang K., Wang Z., Li F., Ye W., Wang J., Song G., Yu S. (2012b) The draft genome of a diploid cotton *Gossypium raimondii*. Nature Genetics 44, 1098-1103.

Wang L., Cook A., Patrick J. W., Chen X.-Y. & Ruan Y.-L. (2014b) Silencing the vacuolar invertase gene GhVIN1 blocks cotton fiber initiation from the ovule epidermis, probably by suppressing a cohort of regulatory genes via sugar signaling. Plant Journal 78, 686-696.

Wang L., Xu C., Wang C. & Wang Y. (2012c) Characterization of a eukaryotic translation initiation factor 5A homolog from *Tamarix androssowii* involved in plant abiotic stress tolerance. BMC Plant Biology 12, 118.

Wang M.-Y., Zhao P.-M., Cheng H.-Q., Han L.-B., Wu X.-M., Gao P., Xia G.-X. (2013a) The cotton transcription factor TCP14 functions in auxin-mediated epidermal cell differentiation and elongation. Plant Physiology 162, 1669-1680.

Wang P., Xue L., Batelli G., Lee S., Hou Y.-J., Van Oosten M. J., Zhu J.-K. (2013b) Quantitative phosphoproteomics identifies SnRK2 protein kinase substrates and reveals the effectors of abscisic acid action. Proceedings of the National Academy of Sciences, U.S.A. 110, 11205-11210.

Wang S., Wang J.-W., Yu N., Li C.-H., Luo B., Gou J.-Y., Chen X.-Y. (2004) Control of plant trichome development by a cotton fiber MYB gene. Plant Cell 16, 2323-2334.

Wang Y., Deng D., Zhang R., Wang S., Bian Y. & Yin Z. (2012d) Systematic analysis of plant-specific B3 domain-containing proteins based on the genome resources of 11 sequenced species. Molecular Biology Reports 39, 6267-6282.

Wang Z.-M., Xue W., Dong C.-J., Jin L.-G., Bian S.-M., Wang C., Liu J.-Y. (2012e) A comparative miRNAome analysis reveals seven fiber initiation-related and 36 novel miRNAs in developing cotton ovules. Molecular Plant 5, 889-900.

Wingler A. & Roitsch T. (2008) Metabolic regulation of leaf senescence: interactions of sugar signaling with biotic and abiotic stress responses. Plant Biology 10, 50-62.

Woo H. R., Kim J. H., Kim J., Kim J., Lee U., Song I.-J., Lim P. O. (2010) The RAV1 transcription factor positively regulates leaf senescence in *Arabidopsis*. Journal of Experimental Botany 61, 3947-3957.

Wu L., Liu D., Wu J., Zhang R., Qin Z., Liu D., Mao L. (2013) Regulation of FLOWERING LOCUS T by a microRNA in Brachypodium distachyon. Plant Cell 25, 4363-4377.

Wu Y., Machado A. C., White R. G., Llewellyn D. J. & Dennis E. S. (2006) Expression profiling identifies genes expressed early during lint fibre initiation in cotton. Plant and Cell Physiology 47, 107-127.

Xu B., Gou J.-Y., Li F.-G., Shangguan X.-X., Zhao B., Yang C.-Q., Chen X.-Y. (2013) A cotton BURP domain protein interacts with α-expansin and their co-expression promotes plant growth and fruit production. Molecular Plant 6, 945-958.

Xu S.-M., Brill E., Llewellyn D. J., Furbank R. T. & Ruan Y.-L. (2012) Overexpression of a potato sucrose synthase gene in cotton accelerates leaf expansion, reduces seed abortion, and enhances fiber production. Molecular Plant 5, 430-441.

Yamaguchi A., Kobayashi Y., Goto K., Abe M. & Araki T. (2005) TWIN SISTER OF FT (TSF) acts as a floral pathway integrator redundantly with FT. Plant and Cell Physiology 46, 1175-1189.

Yang W., Jiang D., Jiang J. & He Y. (2010) A plant-specific histone H3 lysine 4 demethylase represses the floral transition in *Arabidopsis*. Plant Journal 62, 663-673.

Yang Z., Zhang C., Yang X., Liu K., Wu Z., Zhang X., Li F. (2014) PAG1, a cotton brassinosteroid catabolism gene, modulates fiber elongation. New Phytologist 203, 437-448.

Yoo M.-J. & Wendel J. F. (2014) Comparative evolutionary and developmental dynamics of the cotton (*Gossypium hirsutum*) fiber transcriptome. PLoS Genetics 10, e1004073.

Yoshida T., Fujita Y., Maruyama K., Mogami J., Todaka D., Shinozaki K. & Yamaguchi-Shinozaki K. (2015) Four *Arabidopsis* AREB/ABF transcription factors function predominantly in gene expression downstream of SnRK2 kinases in abscisic acid signalling in response to osmotic stress. Plant, Cell & Environment, 38, 35-49.

Zhang D., Zhang T. & Guo W. (2010a) Effect of H2O2 on fiber initiation using fiber retardation initiation mutants in cotton (*Gossypium hirsutum*). Journal of Plant Physiology 167, 393-399.

Zhang F., Zuo K., Zhang J., Liu X., Zhang L., Sun X. & Tang K. (2010b) An L1 box binding protein, GbML1, interacts with GbMYB25 to control cotton fibre development. Journal of Experimental Botany 61, 3599-3613.

Zhang M., Zheng X., Song S., Zeng Q., Hou L., Li D., Pei Y. (2011) Spatiotemporal manipulation of auxin biosynthesis in cotton ovule epidermal cells enhances fiber yield and quality. Nature Biotechnology 29, 453-458.

Zhao L., Hao D., Chen L., Lu Q., Zhang Y., Li Y., Li W. (2012) Roles for a soybean RAV-like orthologue in shoot regeneration and photoperiodicity inferred from transgenic plants. Journal of Experimental Botany 63, 3257-3270.

Zhao L., Luo Q., Yang C., Han Y. & Li W. (2008) A RAV-like transcription factor controls photosynthesis and senescence in soybean. Planta 227, 1389-1399.

The invention claimed is:

1. A seed of a cotton cultivar recombinantly modified by transformation with and overexpression of at least one of AtRAV1 or AtRAV2 or orthologs thereof, wherein the cotton cultivar has longer fibers compared to non-transgenic parent cotton plants grown under drought conditions.

2. The seed of claim 1, wherein the parent cotton cultivar is Coker 312, UA-48, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala Cl, Acala Royale, Acala Maxxa, Acala Prema, Acala B638, Acala B1810, Acala B2724, Acala B4894, Acala B5002, non Acala picker Siokra, stripper variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6, ORO BLANCO PIMA, AXTE1, NM2302, C6TE, NM B3080, C6TE, NM B3080, AXTE 1-57, TEX E364, S196, 1900-1, 12302-4, C6TE, B7378, ATE-11, NM49-2, C6TE or NM B3080.

3. The seed of claim 1, wherein the plant further overexpresses AtABI5.

4. The seed of claim 1, wherein the modifications further comprise delayed flowering.

5. The seed of claim 1, wherein the AtRAV1 or AtRAV2 orthologs are from a dicotyledonous plant selected from the group consisting of soybean, cotton, canola, and potato.

6. A cotton plant, or a part thereof, produced by growing the seed of claim 1.

7. A tissue culture of cells produced from the plant of claim 6, wherein said cells of the tissue culture are produced from a plant part selected from the group consisting of leaves, pollen, embryos, cotyledons, hypocotyl, meristematic cells, roots, root tips, pistils, anthers, flowers, and stems.

8. A protoplast produced from the plant of claim 6.

9. A protoplast produced from the tissue culture of claim 7.

10. A cotton plant regenerated from the tissue culture of claim 7, wherein the plant has all of the morphological and physiological characteristics of conferring longer fibers to transgenic cotton plants with a yield equivalent to cotton cultivar UA-48.

11. A method for producing an $F_1$ hybrid cotton seed, wherein the method comprises crossing the plant of claim 6 with a different cotton plant and harvesting the resultant $F_1$ hybrid cotton seed.

12. A hybrid cotton seed produced by the method of claim 11.

13. A hybrid cotton plant, or a part thereof, produced by growing said hybrid seed of claim 12.

14. A method of producing an insect resistant cotton plant, wherein the method comprises transforming the cotton plant of claim 6 with a transgene that confers insect resistance.

15. An insect resistant cotton plant produced by the method of claim 14.

16. The cotton plant of claim 15, wherein the transgene encodes a *Bacillus thuringiensis* endotoxin.

17. A method of producing a disease resistant cotton plant, wherein the method comprises transforming the cotton plant of claim 6 with a transgene that confers disease resistance.

18. A disease resistant cotton plant produced by the method of claim 17.

19. A method of producing a cotton plant with longer fibers and delayed flowering to transgenic cotton plants under drought conditions, wherein the method comprises recombinantly modifying a cotton cultivar by transformation with and overexpression of at least one of AtRAV1 or AtRAV2 or orthologs thereof, wherein the cotton plant has longer fibers compared to non-transgenic parent cotton plants grown under drought conditions, wherein the transgenic cotton ovules produce longer lint of higher quality without significant reductions in yield.

20. A cotton plant that overexpresses at least one of AtRAV1 or AtRAV2 or orthologs thereof produced by the method of claim 19.

21. The cotton plant of claim 20, wherein a fiber obtained from the plant is stronger and more uniform that from the parent cultivar when both are grown under drought conditions.

22. A method of introducing a desired trait into a cotton cultivar, wherein the method comprises:
(a) crossing a first cultivar with a plant of another cotton cultivar that overexpresses at least one of AtRAV1 or AtRAV2 or orthologs thereof to produce a desired trait to produce progeny plants wherein the desired trait is transgenic cotton ovules that produce longer lint of higher quality without significant reductions in yield;
(b) selecting one or more progeny plants that have the desired trait;
(c) backcrossing the selected progeny plants with the first cultivar to produce backcross progeny plants;
(d) selecting for backcross progeny plants that have the desired trait; and
(e) repeating steps (c) and (d) two or more times in succession to produce selected third or higher backcross progeny plants that comprise the desired trait and all of the physiological and morphological characteristics of the first cultivar that produce longer lint of higher quality without significant reductions in yield.

23. The cotton plant of claim 22, wherein the plant further overexpresses AtABI5.

* * * * *

SEQUENCE LISTING

<160> NUMBER OF SEQ ID NOS: 29

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
gaagcctcat cgataccgtc                                              20

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
gcaaaggttg gtgtcttcaa a                                            21

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
cgaggtcgat ttcttgaatt ctca                                         24

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
tccgttacca ttacgacgcc                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
atctttctcc gccaccaccg                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
tctcgggatc caacacgacg                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
tccaaagccg acaacgacga                                              20

<210> SEQ ID NO 8
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 8
actcggtctc gacgccgttc                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
ccaaacccga accaaaacca                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
cttgacccgg gaatgaagga                                              20

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
tggtggatcc tgatgctcca ag                                           22

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
ttggtcgtgg gctctcatag ca                                           22

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
tgctatgaga gcccacgacc aa                                           22

<210> SEQ ID NO 14
<211> LENGTH: 22
<212> TYPE: DNA
<213> ORGANISM: Artificial Sequence
<220> FEATURE:
<223> OTHER INFORMATION: Synthetic primer

<400> SEQUENCE: 14
cccgaggttg taaagctcag ca                                           22
```

```
<210> SEQ ID NO 15
<211> LENGTH: 24
<212> TYPE: DNA
<213> ORGANISM: Artificial Sequence
<220> FEATURE:
<223> OTHER INFORMATION: Synthetic primer

<400> SEQUENCE: 15
gggatgttag caatggtgtt gagc                                              24

<210> SEQ ID NO 16
<211> LENGTH: 22
<212> TYPE: DNA
<213> ORGANISM: Artificial Sequence
<220> FEATURE:
<223> OTHER INFORMATION: Synthetic primer

<400> SEQUENCE: 16
accggcaacc cgaggttgta aa                                                22

<210> SEQ ID NO 17
<211> LENGTH: 24
<212> TYPE: DNA
<213> ORGANISM: Artificial Sequence
<220> FEATURE:
<223> OTHER INFORMATION: Synthetic primer

<400> SEQUENCE: 17
tccactctcc ctctggcagt taaa                                              24

<210> SEQ ID NO 18
<211> LENGTH: 22
<212> TYPE: DNA
<213> ORGANISM: Artificial Sequence
<220> FEATURE:
<223> OTHER INFORMATION: Synthetic primer

<400> SEQUENCE: 18
ggtcgagtct tcggacacca tt                                                22

<210> SEQ ID NO 19
<211> LENGTH: 22
<212> TYPE: DNA
<213> ORGANISM: Artificial Sequence
<220> FEATURE:
<223> OTHER INFORMATION: Synthetic primer

<400> SEQUENCE: 19
tgagcccaca cttaccgcaa ta                                                22

<210> SEQ ID NO 20
<211> LENGTH: 22
<212> TYPE: DNA
<213> ORGANISM: Artificial Sequence
<220> FEATURE:
<223> OTHER INFORMATION: Synthetic primer

<400> SEQUENCE: 20
cggcaagagt tgcaggttga ga                                                22

<210> SEQ ID NO 21
<211> LENGTH: 22
<212> TYPE: DNA
<213> ORGANISM: Artificial Sequence
<220> FEATURE:
<223> OTHER INFORMATION: Synthetic primer
```

```
<400> SEQUENCE: 21
cccagcaatc aaagaccacc tg                                          22

<210> SEQ ID NO 22
<211> LENGTH: 22
<212> TYPE: DNA
<213> ORGANISM: Artificial Sequence
<220> FEATURE:
<223> OTHER INFORMATION: Synthetic primer

<400> SEQUENCE: 22
agcaaccact tcactgccgt tg                                          22

<210> SEQ ID NO 23
<211> LENGTH: 22
<212> TYPE: DNA
<213> ORGANISM: Artificial Sequence
<220> FEATURE:
<223> OTHER INFORMATION: Synthetic primer

<400> SEQUENCE: 23
tgaataaccc gcagacgaca cc                                          22

<210> SEQ ID NO 24
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
tggagaaatc gagccaagtt gc                                          22

<210> SEQ ID NO 25
<211> LENGTH: 22
<212> TYPE: DNA
<213> ORGANISM: Artificial Sequence
<220> FEATURE:
<223> OTHER INFORMATION: Synthetic primer

<400> SEQUENCE: 25
ccgccctgta tgagccttga aa                                          22

<210> SEQ ID NO 26
<211> LENGTH: 22
<212> TYPE: DNA
<213> ORGANISM: Artificial Sequence
<220> FEATURE:
<223> OTHER INFORMATION: Synthetic primer

<400> SEQUENCE: 26
gccagcgatt gaaggagagg aa                                          22

<210> SEQ ID NO 27
<211> LENGTH: 22
<212> TYPE: DNA
<213> ORGANISM: Artificial Sequence
<220> FEATURE:
<223> OTHER INFORMATION: Synthetic primer

<400> SEQUENCE: 27
tgcattgggg tttgttttc ca                                           22

<210> SEQ ID NO 28
```

```
<211> LENGTH: 22
<212> TYPE: DNA
<213> ORGANISM: Artificial Sequence
<220> FEATURE:
<223> OTHER INFORMATION: Synthetic primer

<400> SEQUENCE: 28
gcctaaggtg ccaaaaccat cc                                              22

<210> SEQ ID NO 29
<211> LENGTH: 22
<212> TYPE: DNA
<213> ORGANISM: Artificial Sequence
<220> FEATURE:
<223> OTHER INFORMATION: Synthetic primer

<400> SEQUENCE: 29
gcattccaag gctgaaatcg tg                                              22
```